US008058506B2

(12) United States Patent
Klimyuk et al.

(10) Patent No.: US 8,058,506 B2
(45) Date of Patent: Nov. 15, 2011

(54) SITE-TARGETED TRANSFORMATION USING AMPLIFICATION VECTORS

(75) Inventors: Victor Klimyuk, Halle/Saale (DE); Yuri Gleba, Halle/Saale (DE); Sylvestre Marillonnet, Halle/Saale (DE)

(73) Assignee: Icon Genetics GmbH (DE)

( * ) Notice: Subject to any disclaimer, the term of this patent is extended or adjusted under 35 U.S.C. 154(b) by 760 days.

(21) Appl. No.: 10/473,508

(22) PCT Filed: Mar. 22, 2002

(86) PCT No.: PCT/EP02/03266
§ 371 (c)(1),
(2), (4) Date: May 14, 2004

(87) PCT Pub. No.: WO02/077246
PCT Pub. Date: Oct. 3, 2002

(65) Prior Publication Data
US 2005/0066384 A1  Mar. 24, 2005

(30) Foreign Application Priority Data
Mar. 23, 2001  (DE) ................... 101 14 209

(51) Int. Cl.
C12N 15/82 (2006.01)
C12N 15/09 (2006.01)
C12N 15/00 (2006.01)
C12N 15/63 (2006.01)
C07H 21/04 (2006.01)
A01H 5/00 (2006.01)
A01H 5/10 (2006.01)

(52) U.S. Cl. ........ 800/278; 800/280; 800/288; 800/295; 435/320.1; 435/440; 435/468; 435/469; 536/23.1; 536/23.2; 536/23.7; 536/24.1

(58) Field of Classification Search .................... None
See application file for complete search history.

(56) References Cited

U.S. PATENT DOCUMENTS

| | | | |
|---|---|---|---|
| 5,139,812 A | 8/1992 | Lebacq | |
| 5,474,925 A | 12/1995 | Maliyakal et al. | |
| 5,501,967 A | 3/1996 | Offringa et al. | |
| 5,527,695 A | 6/1996 | Hodges et al. | |
| 5,576,198 A | 11/1996 | McBride et al. | |
| 5,627,059 A | 5/1997 | Capecchi et al. | |
| 5,635,381 A | 6/1997 | Hooykaas et al. | |
| 5,670,623 A | 9/1997 | Shoseyov et al. | |
| 5,723,765 A | 3/1998 | Oliver et al. | |
| 5,744,336 A | 4/1998 | Hodges et al. | |
| 5,773,689 A | 6/1998 | Thompson et al. | |
| 5,877,402 A | 3/1999 | Maliga et al. | |
| 5,885,836 A | 3/1999 | Wahl et al. | |
| 5,910,415 A | 6/1999 | Hodges et al. | |
| 6,037,525 A | 3/2000 | Thompson et al. | |
| 6,077,992 A * | 6/2000 | Yadav | ........................... 800/278 |
| 6,100,448 A | 8/2000 | Thompson et al. | |
| 6,110,736 A | 8/2000 | Hodges et al. | |
| 6,147,278 A | 11/2000 | Rogers et al. | ................ 800/278 |
| 6,174,700 B1 | 1/2001 | Haynes et al. | |
| 6,175,058 B1 * | 1/2001 | Baszczynski et al. | ........ 800/278 |
| 6,187,994 B1 * | 2/2001 | Baszczynski et al. | ........ 800/278 |
| 6,239,328 B1 | 5/2001 | Thompson et al. | |
| 6,300,545 B1 | 10/2001 | Baszczynski et al. | |
| 6,303,848 B1 | 10/2001 | Kumagai et al. | |
| 6,331,416 B1 | 12/2001 | Shani et al. | |
| 6,331,661 B1 | 12/2001 | Baszczynski et al. | ........ 800/278 |
| 6,686,515 B1 | 2/2004 | Lassner et al. | |
| 6,746,870 B1 | 6/2004 | Ow et al. | |
| 6,781,033 B2 | 8/2004 | Staub et al. | |
| 7,126,041 B1 | 10/2006 | Helmer et al. | |
| 2003/0188337 A1 | 10/2003 | Day et al. | |
| 2004/0005713 A1 | 1/2004 | Baszczynski et al. | |
| 2004/0016014 A1 | 1/2004 | Nguyen et al. | |
| 2004/0016015 A1 | 1/2004 | Nguyen et al. | |
| 2004/0055037 A1 | 3/2004 | Gleba et al. | |
| 2004/0083499 A1 | 4/2004 | Eibl et al. | |
| 2004/0088764 A1 | 5/2004 | Gleba et al. | |
| 2004/0137631 A1 | 7/2004 | Herz et al. | |
| 2004/0191788 A1 | 9/2004 | Gleba et al. | |
| 2004/0221330 A1 | 11/2004 | Klimyuck et al. | |
| 2004/0244073 A1 | 12/2004 | Klimyuck et al. | |
| 2004/0255347 A1 | 12/2004 | Klimyuck et al. | |

(Continued)

FOREIGN PATENT DOCUMENTS
EP   265556   5/1988
(Continued)

OTHER PUBLICATIONS

Stanley (1993, Current Opinion in Genetics and Development 3:91-96 provided in IDS.*
Albert et al. "Site-specific integration of DNA into wild-type and mutant *lox* sites placed in the plant genome" *Plant Journal* 7:649-659 (1995).
Coutts et al. "Development of Geminivirus-based Gene Vectors for Dicotyledonous Plants" *Australian Journal of Plant Physiology* 17:365-375 (1990).
Dale et al. "Intra- and intermolecular site-specific recombination in plant cells mediated by bacteriophage P1 recombinase" *Gene* 91:79-85 (1990).

(Continued)

Primary Examiner — Brent T Page
(74) Attorney, Agent, or Firm — Lerner, David, Littenberg, Krumholz & Mentlik, LLP

(57) ABSTRACT

A process of causing a targeted integration of DNA of interest into a plant cell nuclear genome, comprising; i) providing plant cells with an amplification vector, or a precursor thereof, capable of autonomous replication in plant cells, said vector comprising; a) DNA sequence(s) encoding an origin of replication functional in plant cells, b) DNA sequence(s) necessary for site-specific and/or homologous recombination between the vector and a host nuclear DNA, and c) optionally, further DNA of interest; ii) optionally providing conditions that facilitate vector amplification and/or cell to cell movement and/or site-specific and/or homologous recombination, and iii) selecting cells having undergone recombination at a predetermined site in the plant nuclear DNA.

26 Claims, 30 Drawing Sheets

U.S. PATENT DOCUMENTS

| | | | |
|---|---|---|---|
| 2005/0014150 | A1 | 1/2005 | Atabekov et al. |
| 2005/0015829 | A1 | 1/2005 | Koop et al. |
| 2005/0015830 | A1 | 1/2005 | Dorokhov et al. |
| 2005/0059004 | A1 | 3/2005 | Atabekov et al. |
| 2005/0066384 | A1 | 3/2005 | Klimyuck et al. |
| 2005/0091706 | A1 | 4/2005 | Klimyuck et al. |

FOREIGN PATENT DOCUMENTS

| | | |
|---|---|---|
| EP | 0270 248 | 6/1988 |
| EP | 1 045 037 | 10/2000 |
| WO | WO87/00551 | 1/1987 |
| WO | WO 91/02070 | 2/1991 |
| WO | WO 93/17116 | 9/1993 |
| WO | WO 94/16089 | 7/1994 |
| WO | WO 94/17176 | 8/1994 |
| WO | WO 95/34668 | 12/1995 |
| WO | WO 96/17954 | 6/1996 |
| WO | WO 97/41228 | 11/1997 |
| WO | WO98/09505 | 3/1998 |
| WO | WO 98/44097 | 10/1998 |
| WO | WO 98/54342 | 12/1998 |
| WO | WO99/25821 | 5/1999 |
| WO | WO 99/25821 | 5/1999 |
| WO | WO 99/25840 | 5/1999 |
| WO | WO 99/25841 | 5/1999 |
| WO | WO 99/25853 | 5/1999 |
| WO | WO 99/25854 | 5/1999 |
| WO | WO99/25855 | 5/1999 |
| WO | WO 99/25855 | 5/1999 |
| WO | WO 99/36516 | 7/1999 |
| WO | WO 01/11020 | 2/2000 |
| WO | WO 00/17365 | 3/2000 |
| WO | 00/20557 A2 | 4/2000 |
| WO | WO 00/20611 | 4/2000 |
| WO | WO 00/32799 | 6/2000 |
| WO | WO 00/68391 | 11/2000 |
| WO | WO 00/68431 | 11/2000 |
| WO | WO 00/70019 | 11/2000 |
| WO | WO 00/77174 | 12/2000 |
| WO | WO 00/77175 | 12/2000 |
| WO | WO 00/78985 | 12/2000 |
| WO | WO 01/59138 | 8/2001 |
| WO | WO 01/81600 | 11/2001 |
| WO | WO 02/12522 | 2/2002 |
| WO | WO 02/29068 | 4/2002 |
| WO | WO 02/46438 | 6/2002 |
| WO | WO 02/46440 | 6/2002 |
| WO | WO 02/055651 | 7/2002 |
| WO | WO 02/057466 | 7/2002 |
| WO | WO 02/068664 | 9/2002 |
| WO | WO 02/077246 | 10/2002 |
| WO | WO 02/079481 | 10/2002 |
| WO | WO 02/088369 | 11/2002 |
| WO | WO 02/101060 | 12/2002 |
| WO | WO 03/001900 | 1/2003 |
| WO | WO 03/004658 | 1/2003 |
| WO | WO 03/020927 | 3/2003 |
| WO | WO 03/020928 | 3/2003 |
| WO | WO 03/020938 | 3/2003 |

OTHER PUBLICATIONS

Dale et al. "Mutations in the CRE/LOX Recombination Site Enhance the Stability of Recombination Products: Applications for Gene Targeting in Plants" *Journal of Cellular Biochemistry* 16:206 (1992).

Neunzig et al. "Self replicating vectors as a tool for gene targeting in plants" *Experienta* 46:A34 (1990).

Peterson-Burch et al. "Retroviruses in plants?" *Trends in Genetics* 16:151-152 (2000).

Porta et al. "Use of Viral Replicons for the Expression of Genes in Plants" *Molecular Biotechnology* 5:209-221 (1996).

Stanley, J. "Geminiviruses: plant viral vectors" *Current Opinion in Genetics and Development* 3:91-96 (1993).

Walden et al. "Gene-transfer and plant regeneration techniques" *Trends in Biotechnology* 13:324-331 (1995).

International Search Report corresponding to PCT/EP02/03266; Date of Mailing: Feb. 18, 2003.

Allison et al., "Deletion of rpoB Reveals a Second Distinct Transcription System in Plastids of Higher Plants," The EMBO Journal, 15:11 2802-2809 (1996).

Altschul et al. "Basic Local Alignment Search Tool," J. Mol. Biol., 215:403-410 (1990).

Anandalakshmi et al. (1998) "A viral suppressor of gene silencing in plants" Proc. Natl. Acad. Sci. U.S.A. 95:13079-13084.

Anandalakshmi et al. (2000) "A calmodulin-related protein that suppresses posttranscriptional gene silencing in plants" Science 290:142-144.

Arnold et al. "Allelic Ladder, D18S51 Allele 8" EBI Database accession No. AAX01351 (Apr. 14, 1999) Abstract.

Bagwell, BC "Poly-dA 50mer Probe Target Sequence" EBI Database accession No. AAQ66922 (Jan. 24, 1995) Abstract.

Bateman et al. (2000) "Tools for chloroplast transformation in Chlamydomonas: expression vectors and a new dominant selectable marker" Mol. Gen. Genet. 263:401-410.

Bergamini et al. "Picornavirus IRESes and the Poly(A) tail Jointly Promote Cap-Independent Translation in a Mammalian Cell-free System," RNA, 6:1781-1790 (2000).

Bogorad, Lawrence, "Engineering Chloroplasts: an Alternative Site for Foreign Genes, Proteins, Reactions and Products," TIBTECH, 18:257-263 (Jun. 2000).

Bouchez et al, (1993) "A binary vector based on Basta resistance for in planta transformation of *Arabidopsis thaliana*" C. R. Acad. Sci. Paris, Science de la vie 316:1188-1193.

Boynton et al., "Chloroplast Transformation in Chlamydomonas with High Velocity Microprojectiles," Science, 240:1534-1538 (1988).

Carpin et al. (2001) "Identification of a Ca2+-Pectate Binding Site on an Apoplastic Peroxidase" The Plant Cell 13:511-520.

Chappell et al. "A 9-nt Segment of Cellular mRNA Can Function as an Internal Ribosome Entry Site (IRES) and When Present in Linked Multiple Copies Greatly Enhances IRES Activity," PNAS, 97(4):1536-1541 (Feb. 15, 2000).

Clelland et al. (1999) "Hiding Messages in DNA Microdots," Nature 399:533-534.

Daniell, "New Tools for Chloroplast Genetic Engineering," Nature Biotechnology, 17:855-856 (Sep. 1999).

De Santis-Maciossek et al., "Targeted Disruption of the Plastid RNA Polymerase Genes rpoA, B and C1: Molecular Biology, Biochemistry and Ultrastructure," The Plant Journal, 18(5):477-489 (1999).

Domingo et al. (1999) "Identification of a novel peptide motif that mediates cross-linking of proteins to cell walls" The Plant Journal 20:563-570.

Dorokhov et al. "Polypurine (A)-Rich Sequences Promote Cross-Kingdom Conservation of Internal Ribosome Entry" PNAS 99(8):5301-5306 (Apr. 16, 2002).

Drescher et al., "The Two Largest Chloroplast Genome-Encoded Open Reading Frames of Higher Plants are Essential Genes," The Plant Journal, 22(2):97-104 (2000).

El-Sheekh, M.M. (2000) "Stable Chloroplast Transformation in *Chlamydomonas reinhardtii* using Microprojectile Bombardment" Folia Microbiol. 45(6) 496-504.

Fischer et al., "Selectable Marker Recycling in the Chloroplast," Mol. Gen. Genet., 251:373-380 (1996).

Gatz et al. (1991) "Regulation of a modified CaMV 35S promoter by the Tn10-encoded Tet repressor in transgenic tobacco" Mol. Gen. Genet. 227:229-237.

Hager at al., "Enslaved Bacteria as New Hope for Plant Biotechnologists," Appl. Microbiol. Biotechnol., 54:302-310 (2000).

Heifetz, Peter B., "Genetic Engineering of the Chloroplast," Biochimie, 82:655-666 (2000).

Hoff et al. (2001) "A recombinase-mediated transcriptional induction system in transgenic plants" Plant Mol. Biol. 45:41-49.

Horvath et al., "Targeted Inactivation of the Plastid ndhB Gene in Tobacco Results in an Enhanced Sensitivity of Photosynthesis to Moderate Stomatal Closure," Plant Physiology, 123:1337-1349 (Aug. 2000).

Houdebine et al. "Internal Ribosome Entry Sites (IRESs): Reality and Use" Transgenic Research, 8:157-177 (1999).

Iamtham et al. (2000) "Removal of antibiotic resistance genes from transgenic tobacco plastids" 18:1172-1176.

Ivanov et al. "A Tobamovirus Genome That Contains an Internal Ribosome Entry Site Functional In Vitro," Virology, 232:32-43 (1997).
Jeon et al. (2000) "T-DNA insertional mutagenesis for functional genomics in rice" Plant J. 22:561-570.
Kofer et al., "PEG-Mediated Plastid Transformation in Higher Plants," In Vitro Cell. Dev. Biol.- Plant, 31:303-309 (1998).
Koshinsky et al. (2000) "Cre-lox site-specific recombination between *Arabidopsis* and tobacco chromosomes" The Plant Journal 23:715-722.
Kozak, "Initiation of Translation in Prokaryotes and Eukaryotes" Gene 234:187-208 (1999).
Kumagai et al. (1995) "Cytoplasmic inhibition of carotenoid biosynthesis with virus-derived DNA" Proc. Natl. Acad. Sci. USA 92:1679-1683.
Lehtiö et al. (2001) "Directed immobilization of recombinant staphylococci on cotton fibers by functional display of a fungal cellulose-binding domain" FEMS Microbiology Letters 195:197-204.
Lopez de Quinto et al. "Parameters Influencing Translational Efficiency in Aphthovirus IRES-Based Bicistronic Expression Vectors" Gene 217:51-56 (1998).
Martinez-Salas, Encarnacion. "Internal Ribosome Entry Site Biology and Its Use in Expression Vectors," Current Opinion in Biotechnology, 10:458-464 (1999).
Matzk et al. (1994) "Improved Techniques for haploid Production in Wheat using Chromosome Elimination" Plant Breeding 113:125-129.
Melchers et at (1974) "Somatic Hybridisation of Plants by Fusion of Protoplasts" Molec. Gen. Genet. 135:277-294.
Michael et al. (1999) "Efficient gene-specific expression of Cre recombinase in the mouse embryo by targeted insertion of a novel IRES-Cre cassette into endogenous loci" Mech. Dev. 85:35-47.
Mizuguchi et al. (2000) "IRES-Dependent Second Gene Expression Is Significantly Lower Than Cap-Dependent First Gene Expression in a Bicistronic Vector" Mol. Ther. 1:376-382.
Monde et al.; "Post-Transcriptional Defects in Tobacco Chloroplast Mutants Lacking the Cytochrome b6/f Complex," The Plant Journal, 21(1):61-72 (2000).
Mountford et al. (1995) "Internal ribosome entry sites and dicistronic RNAs in mammalian transgenesis" Trends Genet. 11:179-184.
Niepel et al. (1999) "Identification and Characterization of the Functional Elements within the Tobacco Etch Virus 5' Leader Required for Cap-Independent Translation" J. Virol. 73:9080-9088.
Owens et al. "Identification of Two Short Internal Ribosome Entry Sites Selected From Libraries of Random Oligonucleotides," PNAS, 98(4):1471-1476 (Feb. 13, 2001).
Pearson et al. "Improved Tools for Biological Sequence Comparison," Proc. Nat'l. Acad. Sci. USA, 85: 2444-2448 (Apr. 1988).
Preiss et al. "Dual Function of the Messenger RNA Cap Structure in Poly(A)-tail-promoted Translation in Yeast," Nature, 392:516-520 (Apr. 2, 1998).
Qin et al. (Mar. 1994) "Cre recombinase-mediated site-specific recombination between plant chromosomes" Proc. Natl. Acad. Sci. 91:1706-1710.
Riera-Lizarazu et al. (1993) "Polyhaploid Production in the Triticeae: Wheat x Tripsacum Crosses" Crop Science 33:973-976.
Ruf et al., "Targeted Inactivation of a Tobacco Intron-Containing Open Reading Frame Reveals a Novel Chloroplast-Encoded Photosystem I-Related Gene," The Journal of Cell Biology, 139(1):95-102 (Oct. 6, 1997).
Schreuder et al. (1993) "Targeting of a Heterologous Protein to the Cell Wall of *Saccharomyces cerevisiae*" Yeast 9:399-409.
Serino et al., "RNA Polymerase Subunits Encoded by the Plastid rpo Genes are Not Shared with the Nucleus-Encoded Plastid Enzyme," Plant Physiol., 117:1165-1170 (1998).
Shepard et al. (1983) "Genetic Transfer in Plants Through Interspecific Protoplast Fusion" Science 219:683-688.
Staub et al. (1994) "Extrachromosomal elements in tobacco plastids" Proc. Natl. Acad. Sci. 91:7468-7472.
Staub et al., "Expression of a Chimeric uidA Gene Indicates that Polycistronic mRNAs are Efficiently Translated in Tobacco Plastids," The Plant Journal, 7(5):845-848 (1995).

Suzuki et al. (1997) "Generation and maintenance of tandemly repeated extrachromosomal plasmid DNA in *Chlamydomonas* chloroplasts" Plant J. 11:635-648.
Suzuki et al., "Engineering of the rp123 Gene Cluster to Replace the Plastid RNA Polymerase α Subunit with the *Escherichia Coli* Homologue," Curr. Genet., 38:218-225 (2000).
Toth et al. (2001) "A novel strategy for the expression of foreign genes from plant virus vectors" FEBS Lett. 489:215-219.
Ueda et al. (2000) "Genetic immobilization of proteins on the yeast cell surface" Biotechnology Advances 18:121-140.
Urwin et al. (2000) "Functional characterization of the EMCV IRES in plants" Plant J. 24:583-589.
Valancius et al. (1991) "Testing an "In-Out" Targeting Procedure for Making Subtle Genomic Modifications in Mouse Embryonic Stem Cells" Molecular and Cellular Biology 11:1402-1408.
Van Haaren et al. (1993) "Prospects of applying a combination of DNA transposition and site-specific recombination in plants: a strategy for gene identification and cloning" Plant Molecular Biology 23:525-533.
Vergunst et al. "Cre/lox-mediated site-specific integration of Agrobacterium T-DNA in *Arabidopsis thaliana* by transient expression of cre" Plant Molecular Biology 38:393-406 (1998).
Wells et al. (1999) "Codon optimization, genetic insulation, and rtTA reporter improve performance of the tetracycline switch" Transgenic Res. 8:371-381.
Whitney et al., "Directed Mutation of the Rubisco Large Subunit of Tobacco Influences Photorespiration and Growth," Plant Physiology, 121:579-588 (Oct. 1999).
Wilde et al. (1992) "Control of gene expression in tobacco cells using a bacterial operator-repressor system" EMBO J. 11:1251-1259.
Zhao et al. "Development and evaluation of a complementation-dependent gene delivery system based on cucumber mosaic virus" Arch Virol 145:2285-2295 (2000).
Hagemann et al. "Extranuclear Inheritance: Plastid Genetics" *Progress in Botany*, vol. 55, 260-275 (1994).
Klaus et al. "Generation of Marker Free Plastid Transformants Using a Transiently Cointegrated Selection Gene" *Nature Biotechnology* 22: 225-229 (2004).
Mühlbauer et al. "Functional analysis of plastid DNA replication origins in tobacco by targeted inactivation" *The Plant Journal*, 32:175-184 (2002).
Ruf et al. "Stable Genetic Transformation of Tomato Plastids and Expression of a Foreign Protein in Fruit" *Nature Biotechnology* 19: 870-875 (2001).
Shimada et al. "Fine Structural Features of the Chloroplast Genome: Comparison of the Sequenced Chloroplast Genomes" *Nucleic Acids Research* 19: 983-995 (1991).
Shinozaki et al. "The Complete Nucleotide Sequence of the Tobacco Chloroplast Genome: Its Gene Organization and Expression" *The EMBO Journal* 5: 2043-2049 (1986).
Sidorov et al. "Stable Chloroplast Transformation in Potato: Use of Green Fluorescent Protein as a Plastid Marker" *The Plant Journal* 19: 209-216 (1999).
Santz et al. "Altered local and systemic spread of movement deficient virus in transgenic tobacco plants expressing the cucumber mosaic virus 3a protein" *Arch Virol*. 145:2387-2401 (2000).
Parry et al. "Construction of a bidirectional promoter probe vector and its use in analyzing *nod* gene expression in *Rhizobium loti*" *Gene* 150:105-109 (1994).
Derbyshire et al. "Lightning strikes twice: Intron-intein coincidence" *Proc. Natl. Acad. Sci. USA* 95:1356-1357 (1998).
Lustig et al. "Long Poly(A) Tracts in the Human Genome are Associate with the *Alu* Family of Repeated Elements" *J. Mol. Biol*. 180:753-759 (1984).
Wu at al. "Markeriess Deletions of *pil* Genes in *Myxococcus xanthus* generated by Counterselection with the *Bacillus subtilis sacB* Gene" *Journal of Bacteriology* 178(19):5817-5281 (1996).
Donson et al. "Systemic expression of a bacterial gene by a tobacco mosaic" *Proc. Natl. Acad. Sci. USA* 88: 7204-7208 (1991).
Murakami et al. "High-level expression of exogenous genes by replication-competent retrovirus vectors with an Internal ribosomal entry site" *Gene* 202: 23-29 (1997).

Baszczynski et al. "Targeted Gene Integration and Modification in Plants' Abstract W-25. Congress on In Vitro Biology meeting sponsored by the Society—for In Vitro Biology. New Orleans, LA, Jun. 5-9, 1999.

Bayley et al. "Exchange of gene activity in transgenic plants catalyzed by the Cre-*lox* site-specific recombination system" *Plant Molecular Biology* 18:353-361 (1992).

Buchholz et al. "A simple assay to determine the functionality of Cre or FLP recombination targets in genomic manipulation constructs" *Nucleic Acids Research* 24(15):3118-3119 (1996).

Chilton "*Agrobactertum* gene transfer: Progress on a "poor man's vector" for maize" *Proc. Natl. Acad. Sci.* 90:3119-3120 (1993).

Dale et al. "Gene transfer with subsequent removal of the selection gene from the host genome" *Proc. Natl. Acad. Sci. USA* 88:10558-10562 (1991).

Golic et al. "FLP-mediated DNA mobilization to specific target sites in *Drosophila* chromosomes" *Nucleic Acids Research* 25(18):3665-3671 (1997).

Gordon-Kamm et al. "FLP-mediated transgene excision in maize" Abstract P-14. Congress on In Vitro Biology meeting sponsored by the Society for In Vitro Biology. New Orleans, LA, Jun. 5-9, 1999.

Hooykaas et al. "Gene targeting in plants via homologous and site-specific recombination" Abstract W-24. Congress on In Vitro Biology meeting sponsored by the Society for In Vitro Biology. New Orleans, LA, Jun. 5-9, 1999.

Huang et al. "A bacterial model system for chromosomal targeting" *Nucleic Acids Research* 19(3):443448(1991).

Ishida et al. "High efficiency transformation of maize (*Zea mays L.*) mediated by *Agrobacterium tumefaciens*" *Nature Biotechnology* 14:745-750 (1996).

Kilby et al. "FLP recombinase in transgenic plants: constitutive activity in stably transformed tobacco and generation of marked cell clones in *Arabidopsis*" *The Plant Journal* 8(5):637-652 (1995).

Komari et al. "Vectors carrying two separate T-DNAs for co-transformation of higher plants mediated by *Agrobacterium tumefaciens* and segregation of transformants free from selection markers" *The Plant Journal* 10(1):165-174 (1996).

Kumar et al. "Gene Targeting: Development of Novel Systems for Genome engineering in Plants" In: *Floriculture, Ornamental and Plant Biotechnology*, vol. IV, pp. 84-98, Global Science Books, UK (2006).

Lam "Targeted Gene Insertion in Higher Plants Via Homologous Recombination" Abstract W-23. Congress on In Vitro Biology meeting sponsored by the Society for in Vitro Biology. New Orleans, LA, Jun. 5-9, 1999.

Lyznik et al. "Heat-inducible expression of *FLP* gene in maize cells" *The Plant Journal* 8(2):177-186 (1995).

Lyznik et al. "Activity of yeast FLP recombinase in maize and rice protoplasts" *Nucleic Acids Research* 21(4):969-975 (1993).

Lyznik et al. "FLP-mediated recombination of *FRT* sites in the maize genome" *Nucleic Acids Research* 24(19):3784-3789 (1996).

Medberry et al. "Intra-chromosomal rearrangements generated by Cre-*lox* site specific recombination" *Nucleic Acids Research* 23(3):485-490 (1995).

Odell and Russell "Use of Site-Specific Recombination Systems in Plants" In: *Homologous Recombination and Gene Silencing in Plants*, pp. 219-270, J Paszkowski (Ed.) Klumer Academic Publishers, NL (1994).

Odell et al. "Site-directed recombination in the genome of transgenic tobacco" *Mol. Gen. Genet.* 223:369-378 (1990).

Onouchi et al. "Operation of an efficient site-specific recombination system of *Zygosaccharomyces rouxii* in tobacco cells" *Nucleic Acids Research* 19(23):6373-6378 (1991).

Russell et al. "Directed excision of a transgene from the plant genome" *Mol. Gen. Genet.* 234:49-59 (1992).

Vergunst et al. "Site-specific integration of *Agrobacterium* T-DNA in *Arabidopsis thaliana* mediated by Cre recombinase" *The Plant Journal* 7(4):649-659 (1998).

Wei et al. "Agrobacterium-mediated transformation:state of the art and future prospect" *Chinese Science Bulletin* 45(17): 1537-1546 (2000).

Berlani, R., et al, Plant Molecular Biology, 11: 173-182 (1988).
Borisjuk, N, et al, Nature Biotechnology, 18: 1303-1306 (2000).
Berlani, R., et al, Plant Molecular Biology, 11: 161-172 (1988).
Ow et al., Critical Reviews in Plant Sciences, 14(3); 239-261 (1995).
Sugimoto et al., The Plant Journal, 5(6); 863-871 (1994).
Reiss et al.; PNAS, 93, 3094-3098 (1996).
Timmermans et al.; Annu. Rev. Plant Physiol. Plant Mol. Bio., 1994, 45, 79-112.
Gutierrez, C., EMBO J. 19(5); 792-799 (2000).
Palmer, K.E. and Rybicki, E.P., Plant Science 129; 115-130 (1997).
Bowdoin et al., Critical Reviews in Plant Sciences, 18(1); 71-106 (1999).
Masuda, Virus vol. 50, No. 2, p. 233-241 (2000).
Hirochika et al., Plant Cell vol. 8, p. 725-734 (1996).
Hanley-Bowdoin et al., Proc. Natl. Acad. Sei. USA vol. 87, p. 1446-1450 (1990).

* cited by examiner

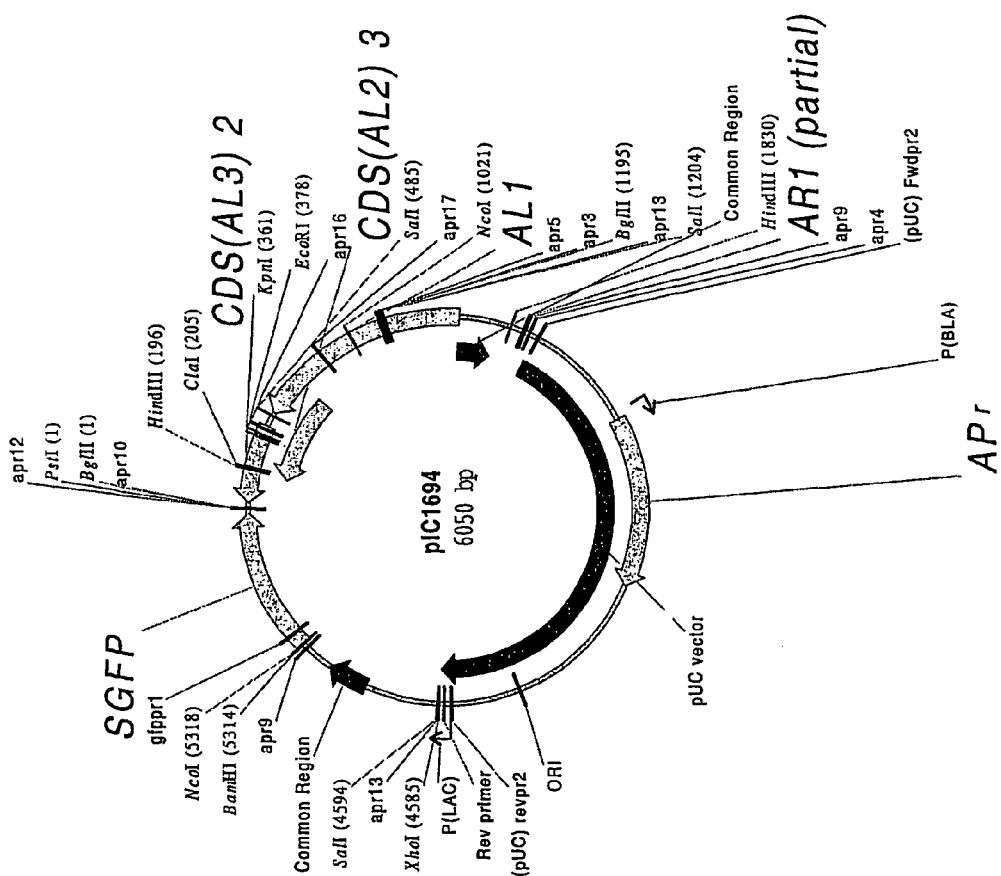
Appendix 1

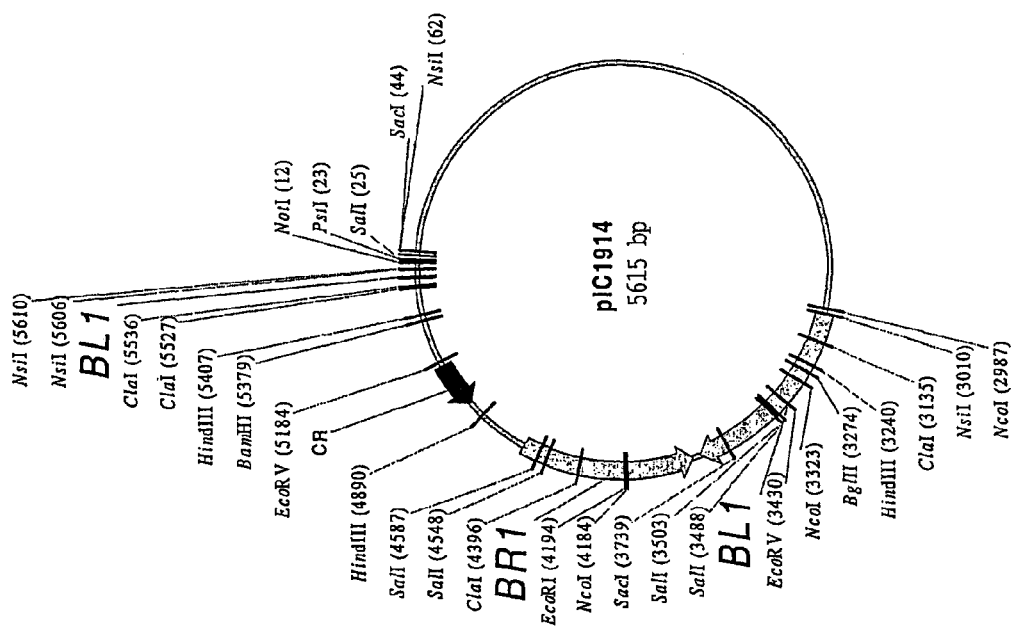

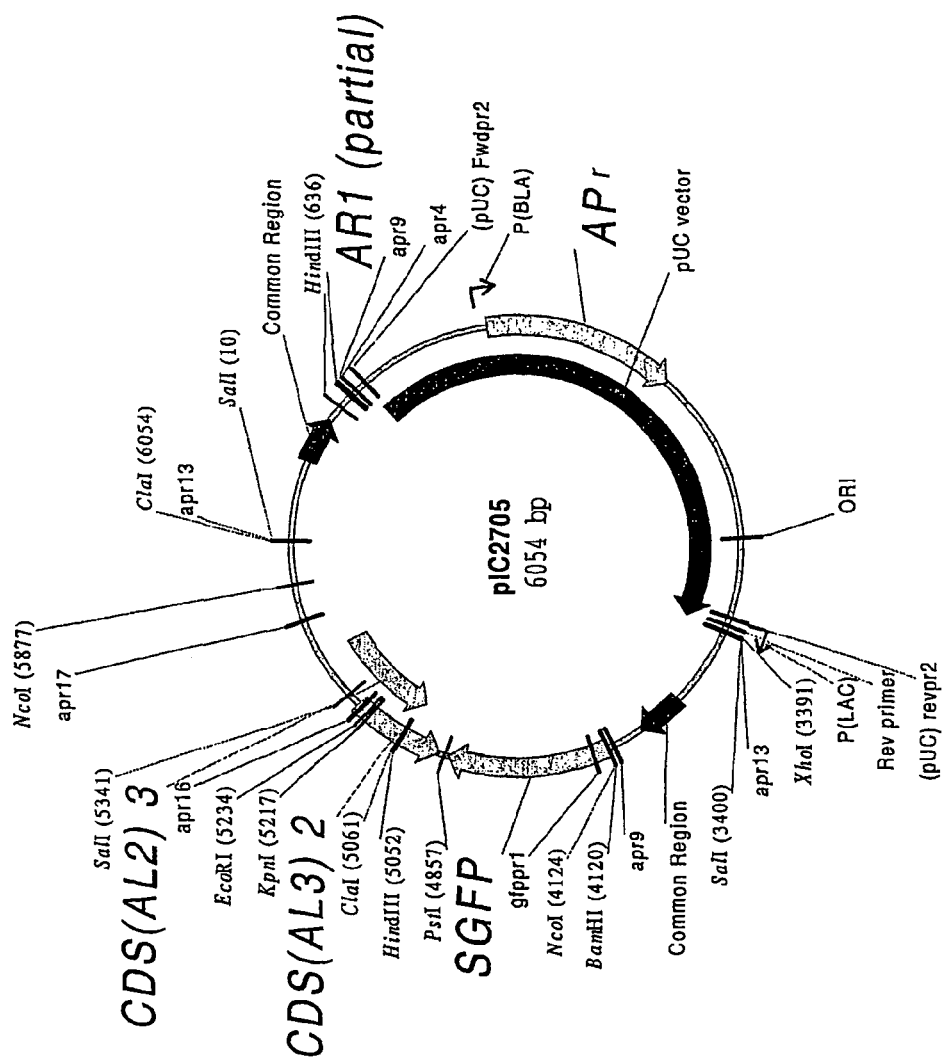

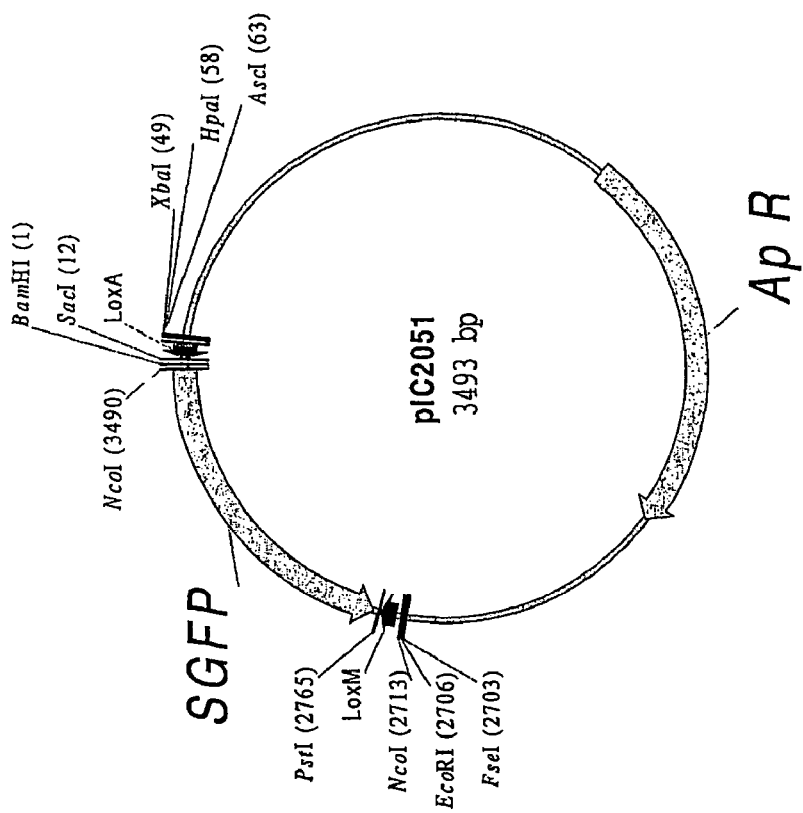
Appendix 4

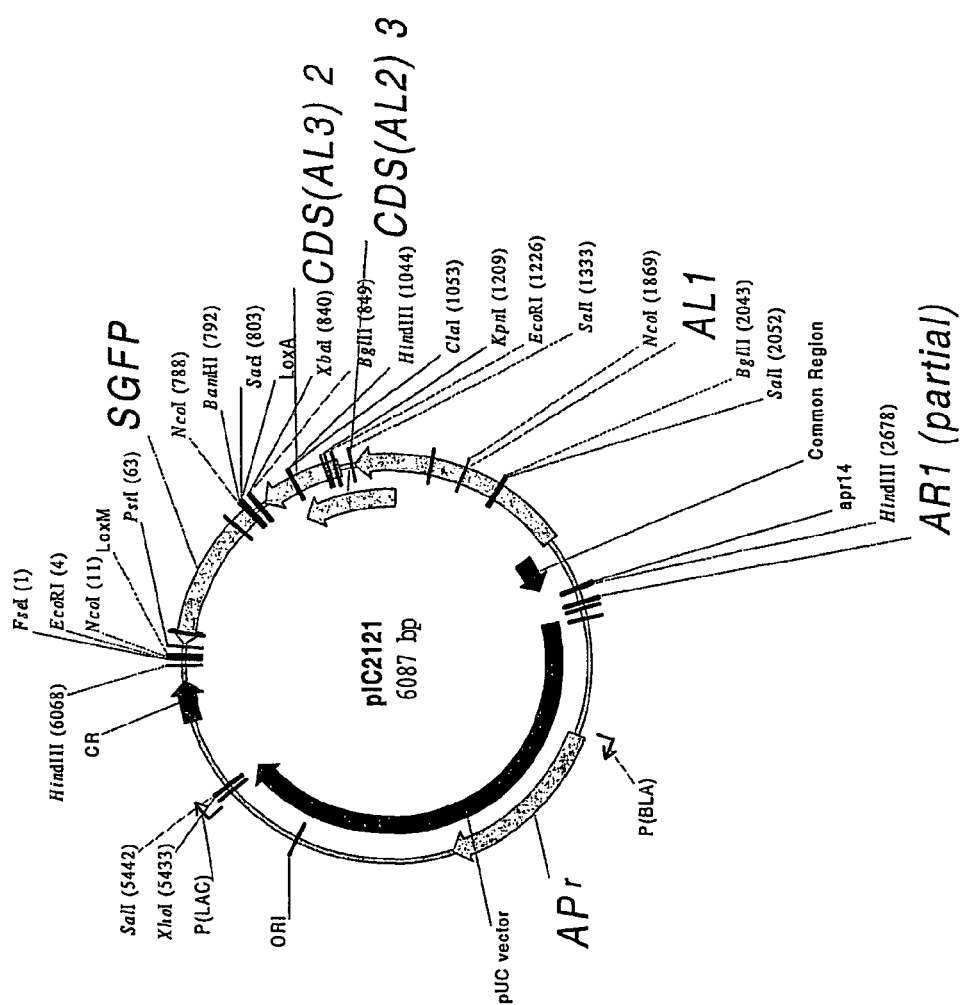

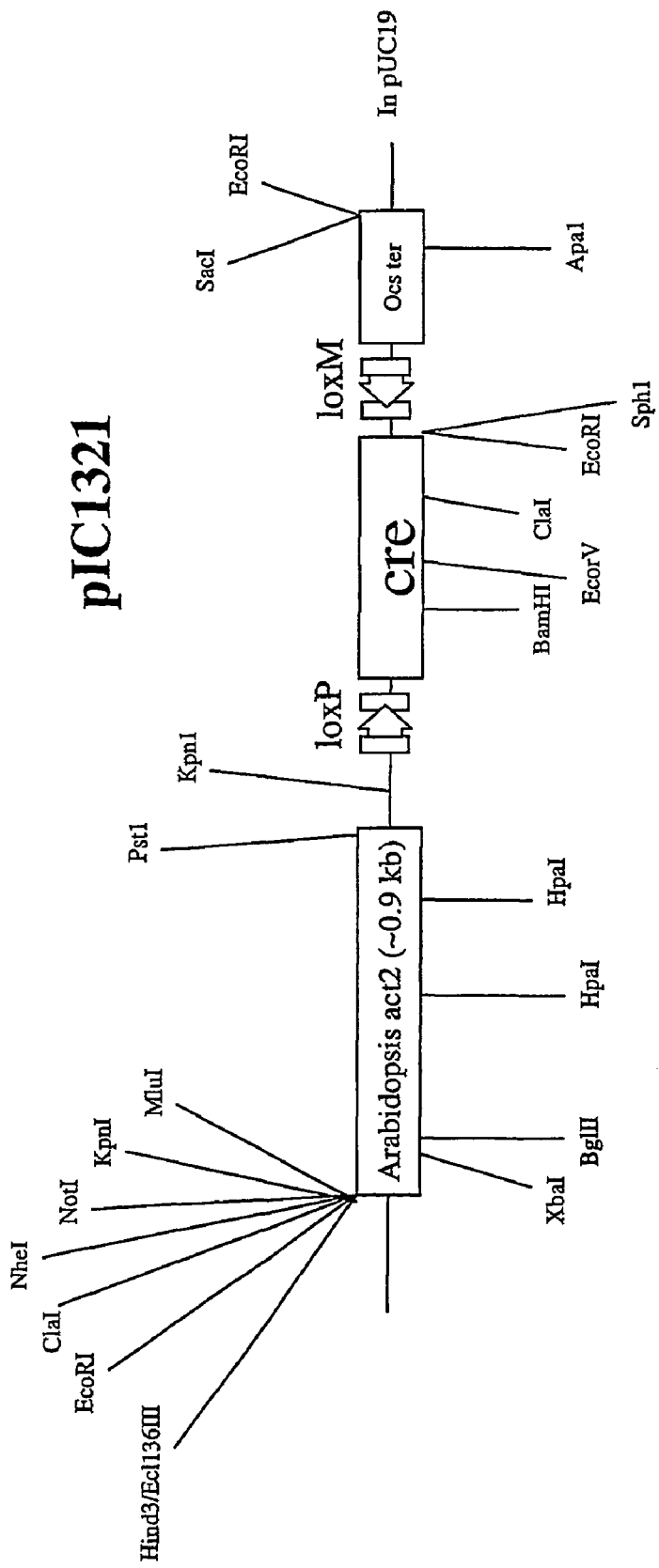
Appendix 6

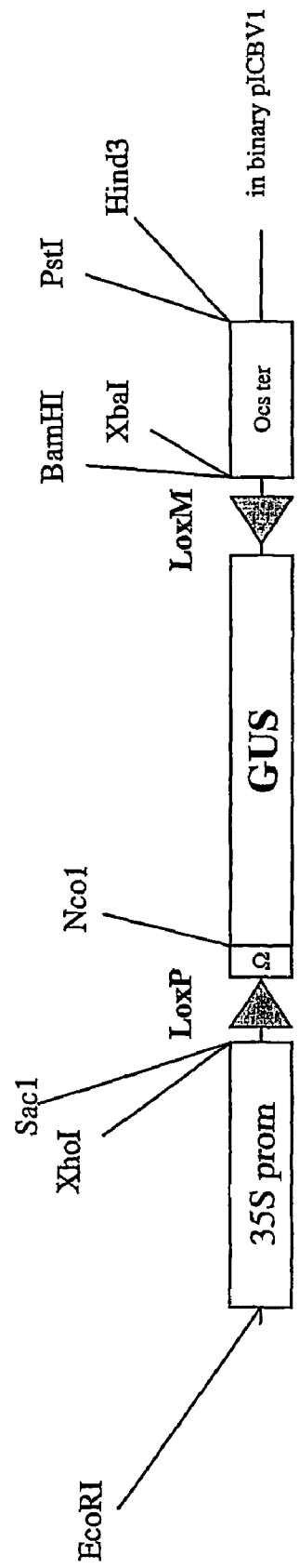

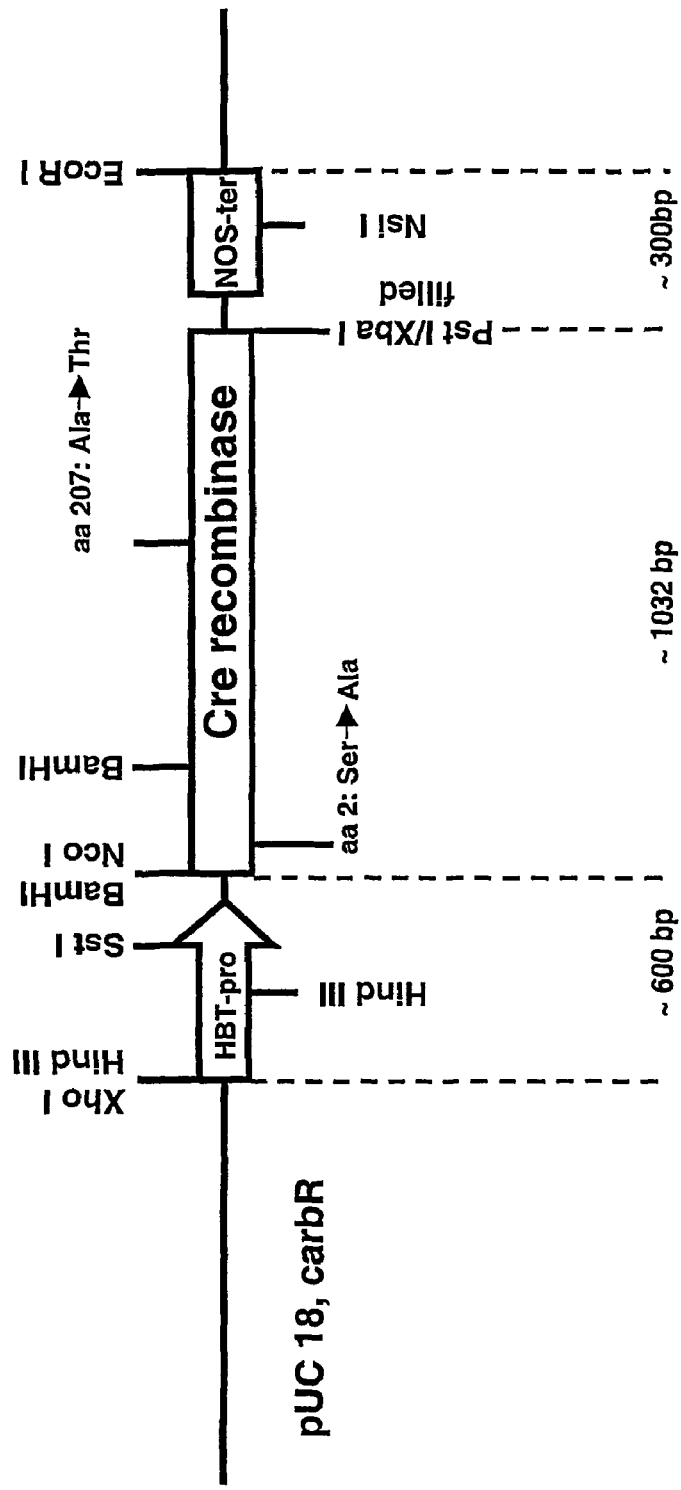

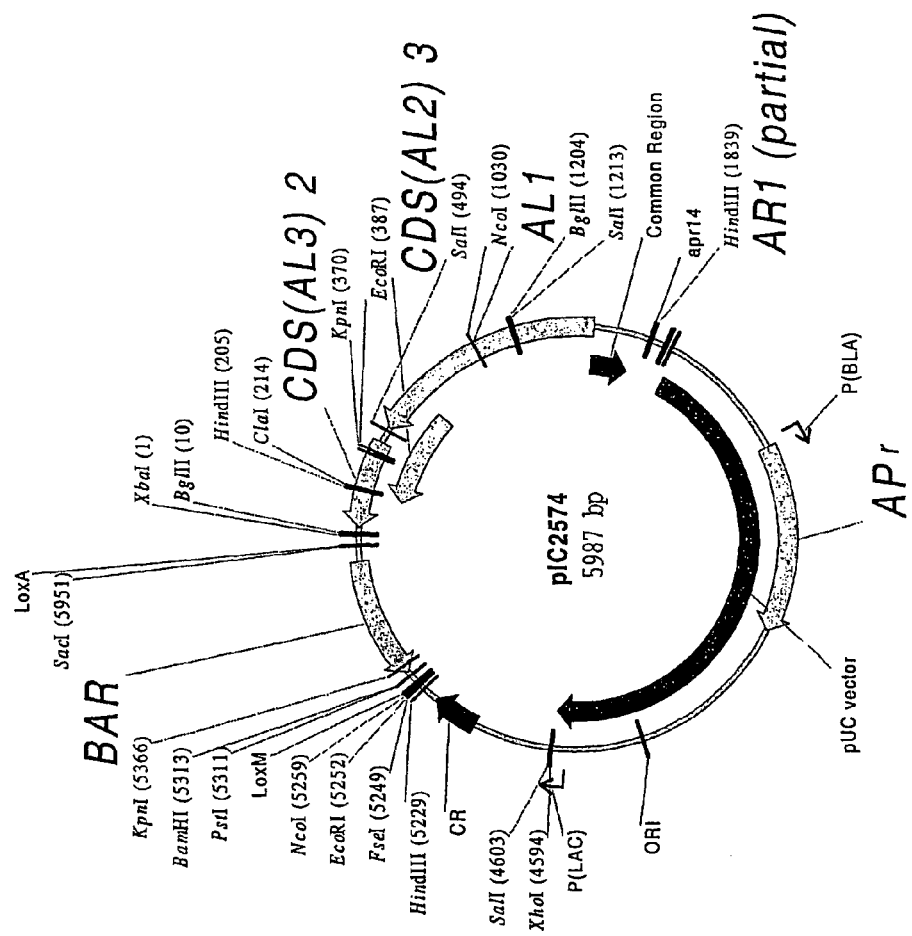
Appendix 9

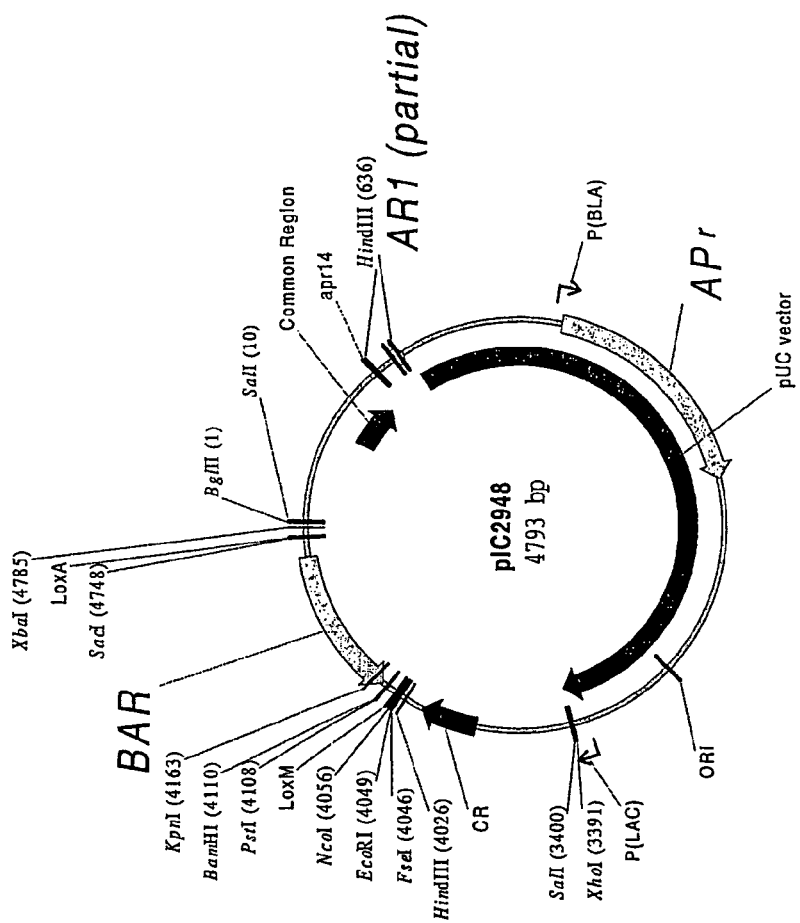
Appendix 10

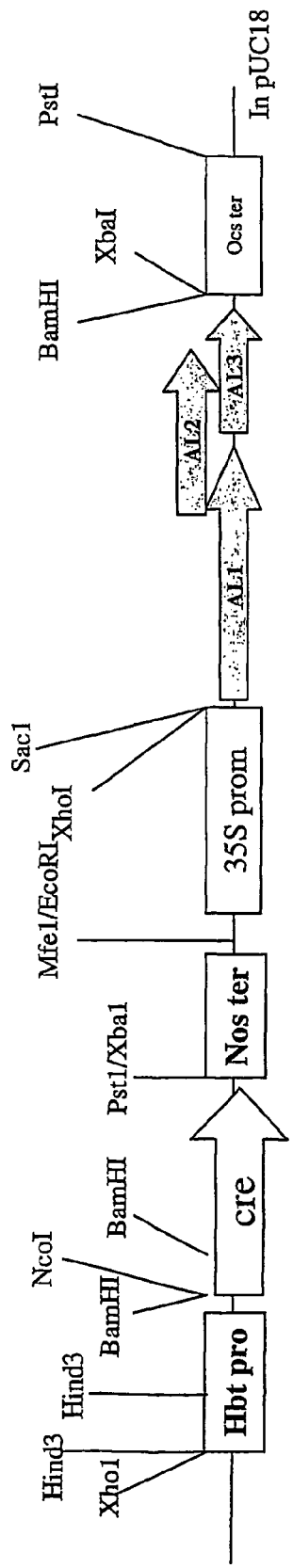
pIC2966
Appendix 11

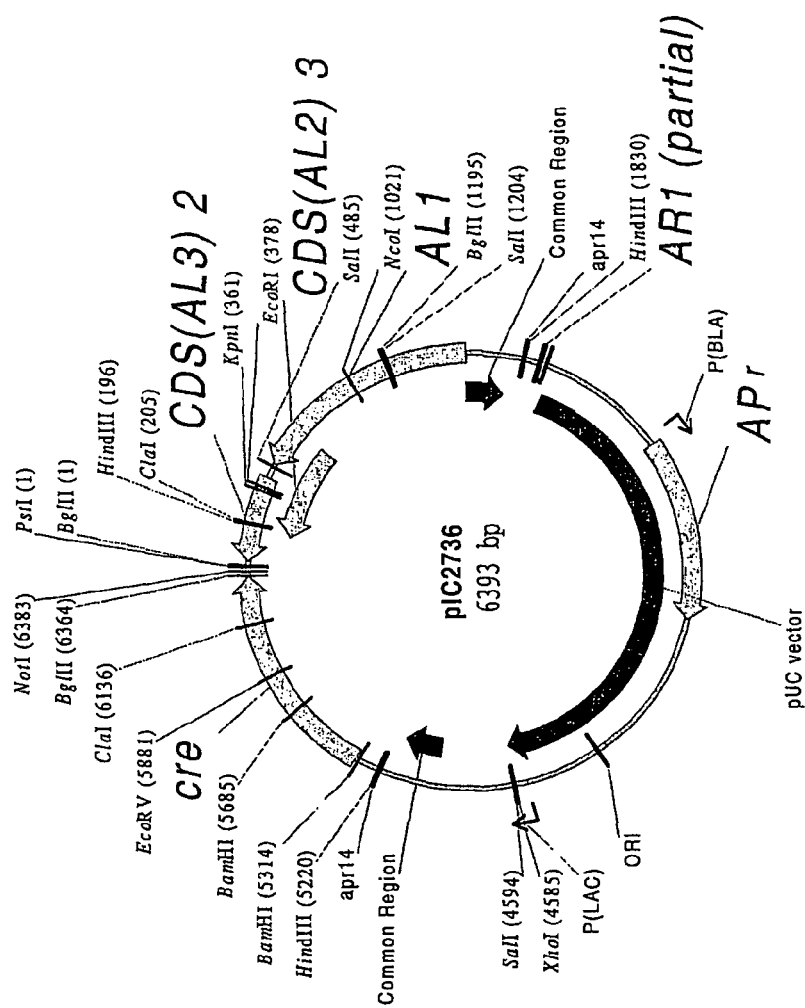
Appendix 12

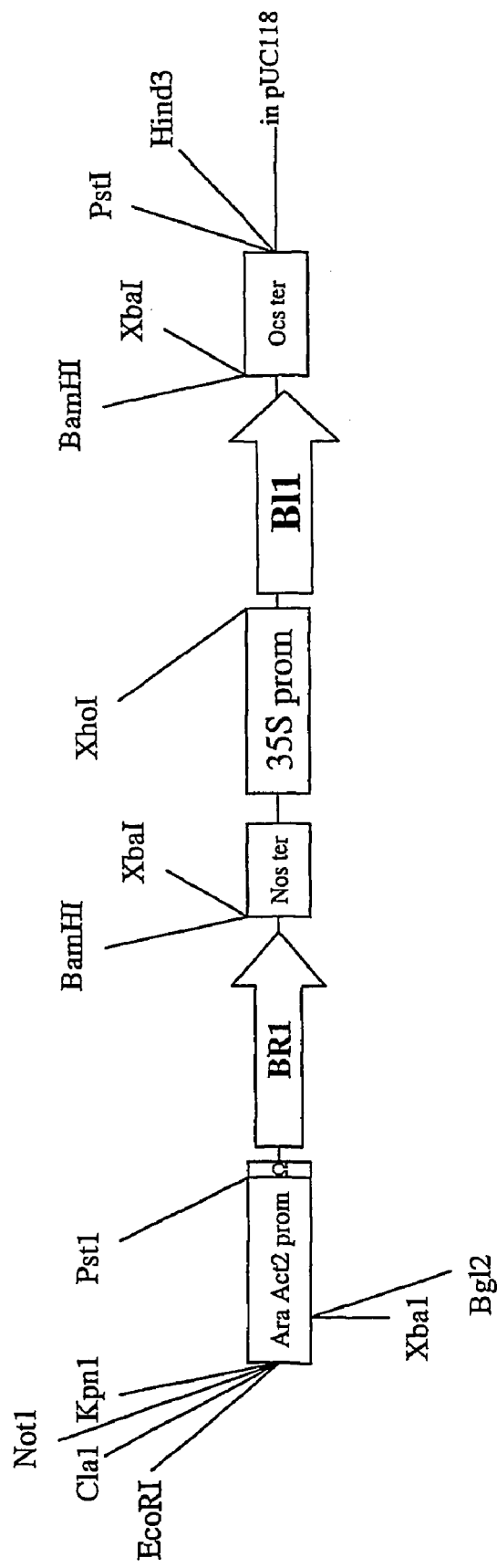

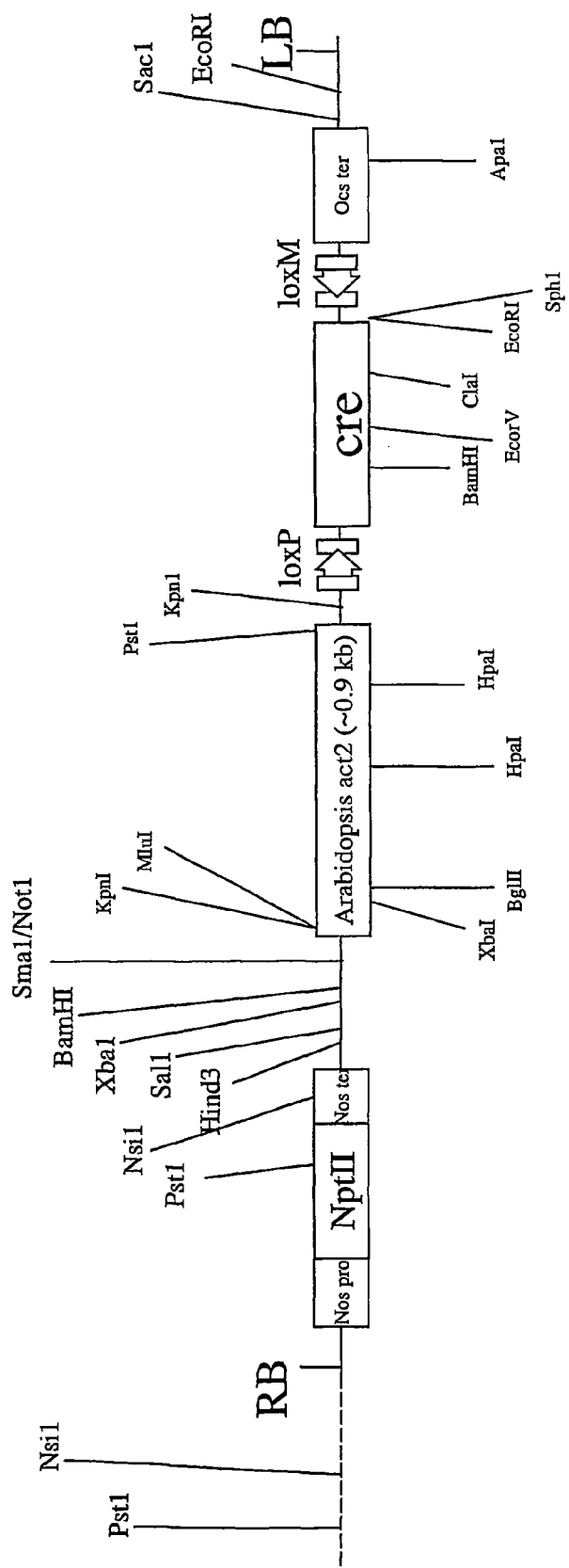

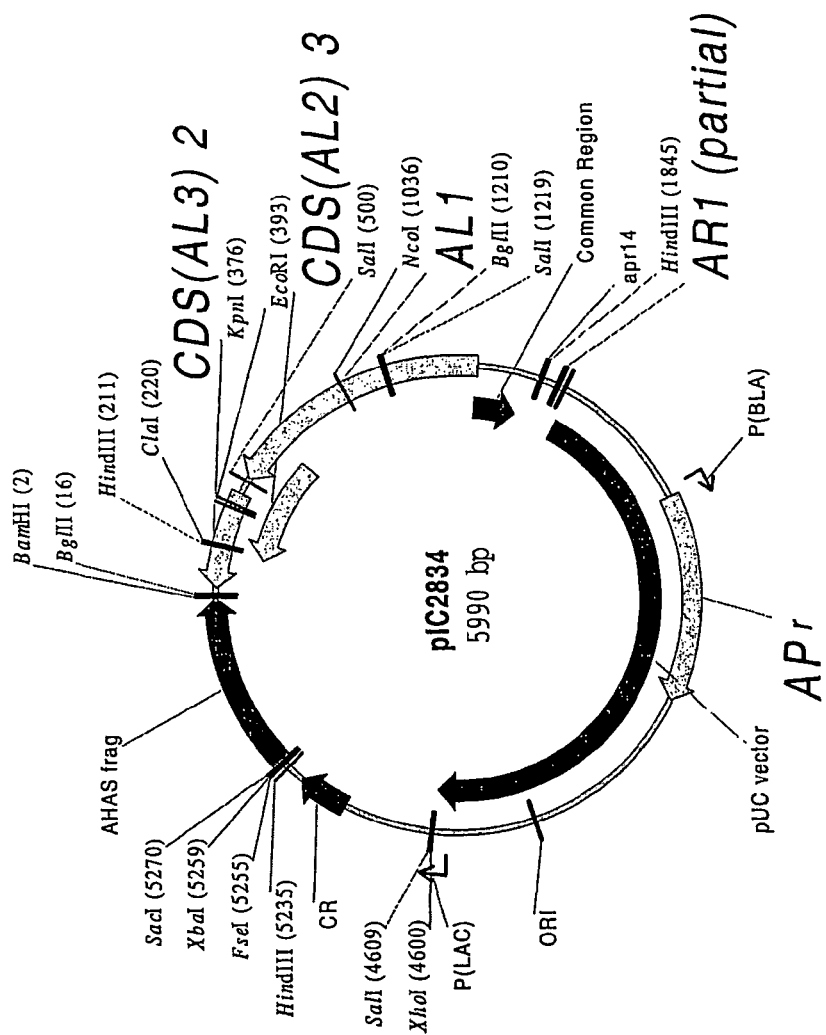
Appendix 15

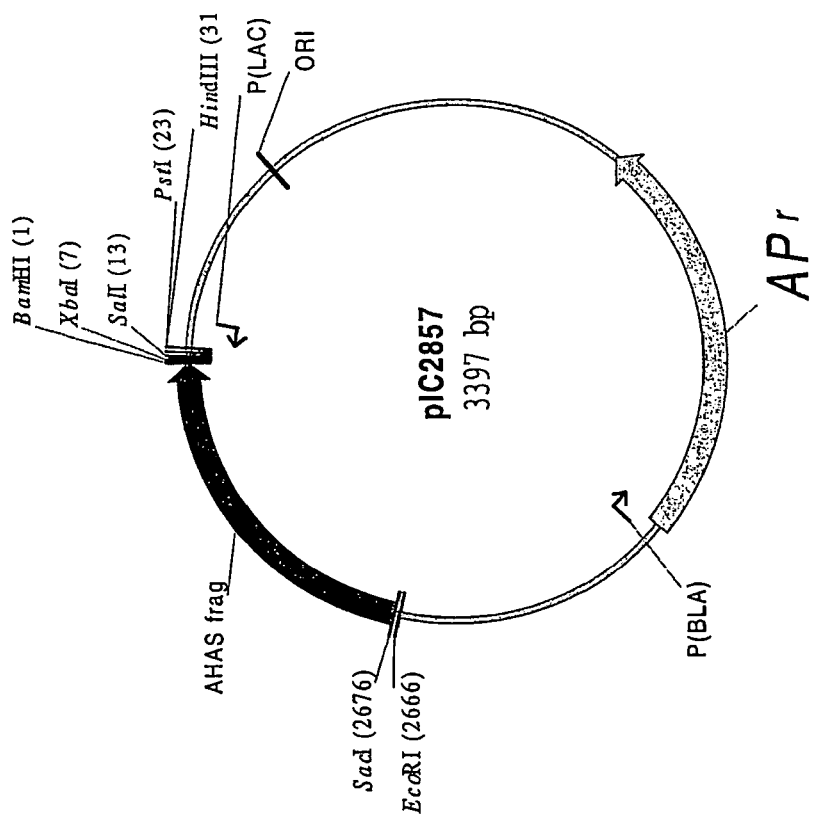
Appendix 16

SITE-TARGETED TRANSFORMATION USING AMPLIFICATION VECTORS

CROSS-REFERENCE TO RELATED APPLICATIONS

The present application is a 35 U.S.C. §371 National Phase Application of International Application Serial No. PCT/EP02/03266, filed Mar. 22, 2002 and published in English as PCT Publication No. WO 02/077246 on Oct. 3, 2002, which claims priority to German Patent Application Serial No. 101 14 209.9, filed Mar. 23, 2001, the disclosures of each of which are incorporated herein by reference in their entireties.

FIELD OF THE INVENTION

The present invention relates to the genetic modification of plants. Particularly, it relates to a process of site-targeted integration of DNA into a plant cell nuclear genome. It further relates to vectors for such a process and to plant cells, seeds and plants produced thereby. Also, a kit-of-parts is provided for performing the process of the invention.

BACKGROUND OF THE INVENTION

With current levels of research in the field of plant molecular genetics and functional genomics, plant transformation is likely to become an increasingly important tool for plant improvement. Limitations of current transformation procedures are numerous but one most important deficiency of currently used techniques is that they result in random insertions of target genes in host genomes, leading to uncontrolled delivery and unpredictable levels of transgene expression. As a result, existing methods require many independent transgenic plants to be generated and analyzed for several generations in order to find those with the desired level or pattern of expression. The vectors for such non-targeted transformation must necessarily contain full expression units, as the subsequent transformation to the same site is impossible, thus limiting engineering capability of the process. A number of different approaches have been investigated in an attempt to develop protocols for efficient targeting of DNA at specific sites in the genome. These efforts include:
  (i) attempts to improve the process of homologous recombination (that relies on the endogenous cellular recombination machinery) by over-expressing some of the enzymes involved in recombination/repair;
  (ii) attempts to decrease non-targeted recombination by down-regulating enzymes that contribute to non-specific recombination;
  (iii) use of heterologous recombinases of microbial origin;
  (iv) development of chimeraplasty for targeted DNA modification in plants.

A brief description of these efforts is summarized below.

Homologous recombination occurs readily in bacteria and yeast, where it is used for gene replacement experiments. More recently it has been developed as a tool for gene replacement in mammals (Mansour et al, 1988, Nature, 336, 348-336; Thomas et al, 1986, Cell, 44, 419-428; Thomas et al, 1987, Cell, 51, 503-512), and the moss Physcomytrella patens (Schaefer & Zryd, 1997, Plant J., 11, 1195-1206). However, it is inefficient in plants. Targeted DNA modification by homologous recombination is accomplished by introducing into cells linear DNA molecules that share regions of homology with the target site. Homologous recombination occurs as a result of a repair mechanism induced by the double-strand breaks at the ends of the DNA fragment. Unfortunately, a competing repair mechanism called non-homologous end-joining (NHEJ) also takes place at a much higher frequency in many organisms and/or cell types, rendering selection of the desired site-targeted events difficult (Haber, 2000, Curr. Op. Cell. Biol., 12, 286-292; Haber, 2000, TIG, 16, 259-264; Mengiste & Paszkowski, 1999, Bio.l Chem., 380, 749-758). In higher plants only a few cases of successful targeted transformation by homologous recombination have been reported, and all were obtained with efficiencies of targeted events over non-targeted events in the range of $10^{-3}$ to $10^{-5}$ (Paszkowski et al., 1988, EMBO J., 7, 4021-4026; Lee et al., 1990, Plant Cell; 2, 415-425; Miao & Lam, 1995, Plant J., 7, 359-365; Offringa et al., 1990, EMBO J., 9, 3077-3084; Kempin et al., 1997, Nature, 389, 802-803). This means that the screening procedure will involve a very large number of plants and will be very costly in terms of time and money; in many cases this will be a futile effort.

Attempts to increase homologous recombination frequencies have been made. Investigators have over-expressed some of the enzymes involved in double-strand break repair. For example, over-expression of either the E. coli RecA (Reiss et al., 1996, Proc Natl Acad Sci USA., 93, 3094-3098) or the E. coli RuvC (Shalev et al., 1999, Proc Natl Acad Sci USA., 96, 7398-402) proteins in tobacco has been tried. However, this has only led to an increase of intrachromosomal homologous recombination (of approximately 10 fold). There was no increase of gene targeting (Reiss et al., 2000, Proc Natl Acad Sci USA., 97, 3358-3363.). Using another approach to increase homologous recombination, investigators have induced double-strand breaks at engineered sites of the genome using rare cutting endonucleases such as the yeast HO endonuclease (Chiurazzi et al, 1996, Plant Cell, 8, 2057-2066; Leung et al., 1997, Proc. Natl. Acad. Sci., 94, 6851-6856) or the yeast I-Sce I endonuclease (Puchta et al., 1996, Proc. Natl. Acad. Sci., 93, 5055-5060). Site targeted frequency of $2\times10^{-3}$ to $18\times10^{-3}$ was obtained using the I-Sce I endonuclease. Although an improvement, this is still inefficient. In addition, many of the targeted events contained unwanted mutations or occurred by homologous recombination at one end of the break only. Incidentally, there is an interesting recent publication describing a hyperrecombinogenic tobacco mutant demonstrating three orders of magnitude increase of mitotic recombination between homologous chromosomes, but the gene(s) involved has not been identified yet (Gorbunova et al., 2000, Plant J., 24, 601-611) and targeted recombination is not involved.

An alternative approach consists of decreasing the activity of enzymes (e.g. Ku70) involved in non-homologous end joining (U.S. Pat. No. 6,180,850) to increase the ratio of homologous/non-homologous recombination events. This approach has been far from being practically useful.

A recently developed approach called chimeraplasty consists of using DNA/RNA oligonucleotides to introduce single-nucleotide mutations in target genes. This approach is highly efficient in mammalian cells (Yoon et al., 1996, Proc. Natl. Acad. Sci. USA., 93, 2071-2076; Kren et al., 1999, Proc. Natl. Acad. Sci. USA., 96, 10349-10354; Bartlett et al., 2000, Nature Biotech., 18, 615-622) with a success rate of more than 40%. Unfortunately, the efficiency is much lower in plants (Zhu et al., 1999, Proc. Natl. Acad. Sci. USA., 96, 8768-8773; Beetham et al., 1999, Proc. Natl. Acad. Sci. USA., 96, 8774-8778; Zhu et al., 2000, Nature Biotech., 18, 555-558; WO9925853) and reaches only a frequency of $10^{-5}$-$10^{-7}$. A further severe drawback of using the chimeraplasty approach in plant systems is that it is limited to the introduction of single-nucleotide mutations and to the special case where the introduced mutation results in a selectable phenotype.

Another approach has been to use heterologous site-specific recombinases of microbial origin. When these recombinases are used, specific recombination sites have to be included on each side not only of the DNA sequence to be targeted, but also of the target site. So far, this has been a severely limiting condition which gives this approach little practical usefulness. Examples of such systems include the Cre-Lox system from bacteriophage P1 (Austin et al., 1981, *Cell*, 25, 729-736), the Flp-Frt system from *Saccharomyces cerevisiae* (Broach et al., 1982, *Cell*, 29, 227-234), the R-RS system from *Zygosaccharomyces rouxii* (Araki et al., 1985, *J. Mol. Biol.*, 182, 191-203) and the integrase from the *Streptomyces* phage PhiC31 (Thorpe & Smith, 1998, *Proc. Natl. Acad. Sci.*, 95, 5505-5510; Groth et al., 2000, *Proc. Natl. Acad. Sci.*, 97, 5995-6000). Wild-type Lox sites (LoxP sites) consist of 13 bp inverted repeats flanking an 8 bp asymetrical core. The asymmetry of the core region confers directionality to the site. Recombination between LoxP sites is a reversible reaction that can lead to deletions, insertions, or translocations depending on the location and orientation of the Lox sites. In plants, the Cre-Lox system has been used to create deletions (Bayley et al, 1992, *Plant Mol. Biol.*, 18, 353-361), inversions (Medberry et al., 1995, *Nucl. Acids. Res.*, 23, 485-490), translocations (Qin et al., 1994, *Proc. Natl. Aced. Sci.*, 91, 1706-1710); Vergunst et al, 2000, *Chromosoma*, 109, 287-297), insertion of a circular DNA into a plant chromosome (Albert et al., 1995, *Plant J.*, 7, 649-659), interspecies translocation of a chromosome arm (Heather et al., 2000, *Plant J.*, 23, 715-722), and removal of selection genes after transformation (Dale & Ow, 1991, *Proc. Natl. Acad. Sc.*, 88, 10558-62; Zuo et al., 2001, *Nat Biotechnol.*, 19, 157-161). One problem encountered when the Cre-Lox system (or a similar recombination system) is used for targeted transformation is that insertion of DNA can be followed by excision. In fact, because the insertion of DNA is a bimolecular reaction while excision requires recombination of sites on a single molecule, excision occurs at a much higher efficiency than insertion. A number of approaches have been devised to counter this problem including transient Cre expression, displacement of the Cre coding sequence by insertion leading to its inactivation, and the use of mutant sites (Albert et al., 1995, *Plant J.*, 7, 649-659; Vergunst et al., 1998, *Plant Mol. Biol.*, 38, 393-406; U.S. Pat. No. 6,187,994). Some site-specific recombinases such as the *Streptomyces* phage PhiC31 integrase should not suffer from the same problem, theoretically, as recombination events are irreversible (the reverse reaction is carried out by different enzymes) (Thorpe & Smith, 1998, *Proc. Natl. Acad. Sci.*, 95, 5505-5510), but they are limited to animals), but the use of this recombination system in plant cells has not been confirmed yet. There are other flaws that render the site-specific recombination systems practically unattractive. First, one needs to engineer a landing or docking site in the recipient's genome, a procedure that is currently done by random insertion of recombination sites into a plant genome. This eliminates most of benefits of the site-specific integration. Second, the frequency of desired events is still very low, especially in economically important crops, thus limiting its use to tobacco and *Arabidopsis*. Expression of recombinant enzymes in plant cells leads to a toxicity problems, an issue that cannot be circumvented with commonly used systems such as Cre-lox or Flp-frt.

WO 99/25855 and corresponding intermediate U.S. Pat. No. 6,300,545 disclose a method of mobilizing viral replicons from an *Agrobacterium*-delivered T-DNA by site-specific recombination-mediated excision for obtaining a high copy number of a viral replicon in a plant cell. It is speculated that said high copy number is useful for site-targeted integration of DNA of interest into a plant chromosome using site-specific recombination. However, the disclosure does not contain information on how to test this speculation. The examples given in the disclosure do not relate to site-targeted integration. Moreover, the examples cannot provide cells having undergone site-targeted integration, but only plants showing signs of viral infection such as appearance of yellow spots and stripes at the base of new leaves indicative of the decay of the infected cells. Therefore, the teaching of these references is limited to the infection of cells leading to the destruction of the cell by the viral vector. The teaching of these references neither allows the determination as to whether or not integration into the nuclear genome has taken place, let alone the selection of successful site-targeted integration events. This is underlined by the fact that the references do not contain a disclosure of selection methods for recovering site-targeted transformants. Selection and recovery of transgenic progeny cells containing said DNA of interest site-specifically integrated into the nuclear genome is simply impossible based on the teaching of these references. Moreover, WO 99/25855 and U.S. Pat. No. 6,300,545 are silent on this problem. Further, these documents are silent on homologous recombination. Moreover, the method is limited to replicon delivery by way of *Agrobacterium*.

Therefore, it is the problem of the invention to provide a process for targeted transformation of plants which is sufficiently efficient for practical purposes.

It is a further problem of the invention to provide a method of targeted integration of DNA of interest into a plant cell nuclear genome that allows recovery of integration events, i.e. selection of cells having undergone recombination in the plant nuclear DNA.

It is a further problem of the invention to provide a method of targeted integration of DNA of interest into a plant cell nuclear genome by homologous recombination.

It is therefore a further problem of the invention to provide a method of targeted integration of DNA of interest into a plant cell nuclear genome by delivery methods independent from *Agrobacterium*-mediated methods.

SUMMARY OF THE INVENTION

This problem is solved by a process of causing a targeted integration of DNA of interest into a plant cell nuclear genome, comprising:

(i) providing plant cells with an amplification vector, or a precursor thereof, capable of autonomous replication in plant cells, said vector comprising:
   (a) DNA sequences encoding an origin of replication functional in plant cells,
   (b) DNA sequence(s) necessary for site-specific and/or homologous recombination between the amplification vector and a host nuclear DNA, and
   (c) optionally, a further DNA of interest;

(ii) optionally providing conditions that facilitate vector amplification and/or cell to cell movement and/or site-specific and/or homologous recombination, and (iii) selecting cells having undergone recombination at a predetermined site in the plant nuclear DNA.

Further, a process of causing a targeted integration of DNA of interest into a plant cell nuclear genome is provided, comprising the following steps:
(i) transfecting or transforming a plant cell with a first DNA comprising a sequence which, when integrated in the plant cell genome, provides a target site for site-specific and/or homologous recombination;
(ii) selecting a cell which contains said target site for site-specific and/or homologous recombination in its nuclear genome;
(iii) transfecting or transforming said selected cell with a second DNA comprising a region for recombination with said target site and a first sequence of interest;
(iv) optionally providing enzymes for recombination; and
(v) selecting cells which contain the sequence of interest from the second DNA integrated at the target site,
whereby at least one of said first or said second DNA is delivered by an amplification vector, or a precursor thereof, capable of autonomous replication in a plant cell and comprising DNA sequences encoding an origin of replication functional in the plant cell.

Further, this invention provides plant cells, seeds and plants obtained or obtainable by performing these processes and a vector (amplification vector) or pro-vector (precursor) for performing these processes. Moreover, the invention provides *Agrobacterium* cells and packaged viral particles containing said vector or pro-vector.

Finally, the invention provides a kit-of-parts comprising
(i) plant cells, seeds or plants, notably according to steps (i) and (ii) of the above five-step process and
(ii) a vector or pro-vector according to the invention and/or said *Agrobacterium* cells and/or said packaged viral particles.

A further kit-of-parts is provided comprising a vector or a pro-vector for performing steps (i) and (ii) of the above five-step process and a vector for performing steps (iii) and (iv) of that process.

It has been found that surprisingly the efficiency of site-targeted transformation of plant cells can be greatly improved by providing DNA sequences for site-specific and/or homologous recombination by an amplification vector. The exact reasons for this improvement are not yet known but it may be due to an increase of the copy number of the sequence(s) to be targeted. Examples are provided which demonstrate a strong increase of site-targeted insertion events by using amplification vectors as opposed to non-amplifying vectors. It is even more surprising that this increased copy number does not at the same time increase the frequency of non-targeted or random insertion of the sequence(s) to be targeted into the nuclear genome. As a result, the ratio of targeted to random insertion frequencies is highly increased by the processes of this invention. Most importantly, targeted transformation reaches a level of efficiency such that it may now become a routine method in plant biotechnology.

Replication of the amplification vector, however, renders selection of integration events difficult or impossible since high copy numbers of an amplification vectors lead to disease symptoms, impediment of cell division and ultimately to death of affected cells. Consequently, progeny cells containing DNA of interest integrated into the nuclear genome cannot be obtained. The inventors were therefore faced with the following dilemma: on the one hand, efficient site-targeted integration requires replication of the vector. On the other hand, said replication prevents selection of cells having undergone recombination in the plant nuclear DNA.

The inventors of the invention have surprisingly identified ways out of this dilemma. Preferably, the processes of the invention are designed such that the replication of said amplification vector in cells transformed or transfected with said amplification vector is transient. Transient replication means temporal replication, i.e. a replication that lasts for a limited period of time necessary to achieve or to detect homologous and/or site-specific recombination within said cells and integration of said DNA of interest into the nuclear genome. Transient replication of the amplification vector does preferably not prevent the ability of said cells to divide such that progeny cells are formed which can be selected. Preferably, the amplification vector disappears in progeny cells. Below, examples are provided which demonstrate successful selection of progeny cells according to the invention.

Transient replication of the amplification vector may be achieved in several ways. One possibility is to provide the nucleic acid polymerase (replicase) involved in replicating the amplification vector transiently such that replication stops when said polymerase disappears. This may be done by providing the replicase gene to the plant cell on a non-replicating vector (cf. example 6). Preferably, selection pressure used for maintaining said non-replicating vector may be relieved to this end. Further, replication may stop or diminish as a result of the recombination event (cf. example 13), e.g. by rendering the replicase gene non-expressible.

The invention further provides a process of causing targeted integration of DNA of interest into a plant cell nuclear genome comprising:
(i) providing plant cells with an amplification vector, or a precursor thereof, capable of autonomous replication in plant cells, said vector comprising:
 (a) DNA sequences encoding an origin of replication functional in plant cells,
 (b) DNA sequence(s) necessary for homologous recombination between the amplification vector and a host nuclear DNA, and
 (c) optionally, a further DNA of interest;
(ii) optionally providing conditions that facilitate vector amplification and/or cell to cell movement and/or site-specific and/or homologous recombination, and
(iii) selecting cells having undergone recombination at a predetermined site in the plant nuclear DNA.

In order to amplify in a plant cell, the amplification vector used in this invention has to have an origin of replication functional in a plant cell. The origin of replication may be derived from a plant nuclear genome, e.g. from a ribosomal DNA intergenic spacer region. Alternatively, the origin of replication may be of non-plant origin or of synthetic nature. Preferably, the origin of replication is derived from a plant virus, most preferably from a plant DNA virus. The origin of replication is functional in a plant cell if it is recognised by a replication enzyme (DNA or RNA polymerase) in said cell. The replication enzyme is preferably of the same origin as the origin of replication. If the replication enzyme originates from the plant species to be transformed, no foreign replication enzyme has to be provided to said plant cells. In order to facilitate vector amplification, a replication enzyme may be provided, notably if said origin of replication originates from a source different from said plant cells. This enzyme may be encoded on the amplification vector, on an additional vector or it may be incorporated into the plant nuclear genome.

The amplification vector may be a plant virus-derived vector. It may be derived from an RNA virus. In this case it is preferably a DNA copy or a replication intermediate of an RNA virus-derived vector. Preferably however, the vector is derived from a DNA virus. A vector may be considered to be derived from an RNA or DNA virus, if it contains at least one functional element of such a virus. Preferably, such a functional element is an origin of replication which is recognized by a replication enzyme (polymerase) of that virus.

Geminiviridae are particularly well-suited for the purpose of performing this invention. Preferably, the amplification vector has additionally other sequences encoding viral functions for host infectivity, cell-to-cell and/or systemic movement for spreading throughout the plant and for further increasing the frequency of targeted transformation. The amplification vector may have further sequences for functions such as integration into the host chromosome, viral particle assembly, control of gene silencing by the host, and/or control of host physiology. Alternatively, such additional viral functions may be provided on an additional vector. The additional vector may be a replicating vector as well. Preferably, the additional vector is a non-replicating vector such that the additional viral functions are only transiently expressed. This may reduce disease symptoms of the plant. Further, the amplification vector may be of retrotransposon origin.

The amplification vector may further contain a DNA sequence of interest e.g. a gene to be expressed e.g. for conferring a useful trait, for performing mutagenesis etc.

Said site-specific or homologous recombination takes place between the amplification vector and a host nuclear DNA. Said host nuclear DNA may belong to a nuclear chromosome of the host or it may belong to an episomal nuclear DNA. Preferably, said recombination takes place between the amplification vector and a DNA on a nuclear chromosome of the host.

In order to facilitate site-specific or homologous recombination, suitable recombination enzymes such as site-specific recombinases, restriction enzymes or integrases may be provided from an additional vector or from a gene previously incorporated into said plant. Such an additional vector may be co-transformed with the amplification vector or it may be transformed separately. Expression of the recombination enzyme may be constitutive or inducible. Preferably, the recombination enzyme is only transiently expressed e.g. from a non-replicating vector. If the recombination enzyme is present at the target locus of the nuclear genome, its function may be destroyed as a result of the recombination event.

In case of homologous recombination, a recombination enzyme may not have to be provided externally and the process may rely on an endogenous recombinase. However, the efficiency may be further increased by additionally providing a recombination enzyme for promoting homologous recombination. Such an enzyme may be an enzyme native to said plant, a heterologous enzyme or an engineered enzyme.

If homologous recombination is used to target a DNA of interest into the nuclear genome of the plant, any site in the nuclear genome may be targeted as long as suitable selection means exist to select for the desired recombination event. Selection may be achieved by introducing a mutation conferring an antibiotic or inhibitor resistance or by providing a resistance marker gene. As more genome sequences become known, targeting of a desired site by homologous recombination becomes more broadly applicable.

A preferred embodiment of targeted homologous recombination is site-directed mutagenesis of a gene of the plant nuclear genome. For this purpose, the amplification vector may contain the desired mutation flanked by homologous sequences of the target site.

If site-specific recombination is used to target a DNA of interest into the nuclear genome of the plant, target site(s) recognizable by site-specific recominases are preferably pre-introduced into the plant according to the above five-step process. The above five-step process comprises two stages: in the first stage (step (i) and (ii)), a transgenic plant having pre-engineered target sites for site-specific recombination is produced. Preferably, the target sites are stably incorporated into the nuclear genome. Transfecting or transforming said first DNA in step (i) of the five-step process may be non-targeted. Many transgenic plants with target sites introduced in many different loci of the genome may be produced. Then a transgenic plant line with the target site at a desired location may be chosen for performing the steps of the second stage (steps (iii) to (v)). Integration of a DNA of interest in the second stage can then be targeted. According to this process, stable transgenic plant lines may be produced in the first phase. Each such transgenic plant line may then be used for various purposes according to the second stage, making this process highly versatile. At least one of said first or said second DNA is delivered by an amplification vector. Preferably, at least said second DNA is delivered by an amplification vector.

Both said first and said second DNA may comprise a sequence of interest. Such a sequence of interest may be a selectable marker and/or a gene to be expressed e.g. for conferring the plant with a useful trait. Preferably, the recombination event may establish a functional sequence. An example for the establishment of a functional sequence is the placement of a DNA to be expressed under the control of a promoter, whereby the promoter may be provided by said first or said second DNA and the DNA to be expressed may be provided by said second or said first DNA, respectively. Further, other functions necessary for functional expression of a gene such as combination of two fragments of a coding sequence may be combined by said recombination event. The recombination event may also be used to destroy the function of a gene or to eliminate a sequence at the target site.

Said plant cells may be provided with said amplification vector (e.g. a replicon) or with (a) precursor(s) thereof (a pre-replicon or pro-vector). If said plant cells are provided with said precursor, the precursor has to be adopted to be processed to said amplification vector in the plant cell. The amplification vector may e.g. be excised from a precursor by recombination. However, if an amplification vector is to be excised from a precursor, this is preferably achieved by providing the precursor with two origins of replication for allowing replicative release of the amplification vector. Excision of the amplification vector from a precursor is preferably done in combination with *Agrobacterium* transformation for excising the amplification vector out of the Ti-plasmid delivered by *Agrobacterium*. Further, the amplification vector may be assembled in plant cells from two or more precursors by recombination.

Said plant cells may be provided with said amplification vector or its precursor by several methods. Preferred methods are *Agrobacterium*-mediated delivery, direct viral transfection, and non-biological delivery (e.g. particle bombardment). In direct viral transfection, infectious viral material is directly applied to plant tissue. Direct viral transfection should be distinguished from Agroinfection where viral DNA is delivered indirectly using *Agrobacterium*. In *Agrobacterium*-mediated delivery, Ti-plasmids are delivered as precursors of amplification vectors, which are processed in the plant cell to generate said amplification vectors. Direct viral transfection and non-biological delivery methods are preferred.

X—donor molecule or sequence of interest; Y—acceptor or target site; Z—frequency of site-targeted or homologous recombination events; W—frequency of non-homologous recombination or random integration events. Larger letters mean increased number/concentration of molecules (X, Enzymes), target sites (Y) and increased frequency of recombination events (Z, W).

Figure 2:
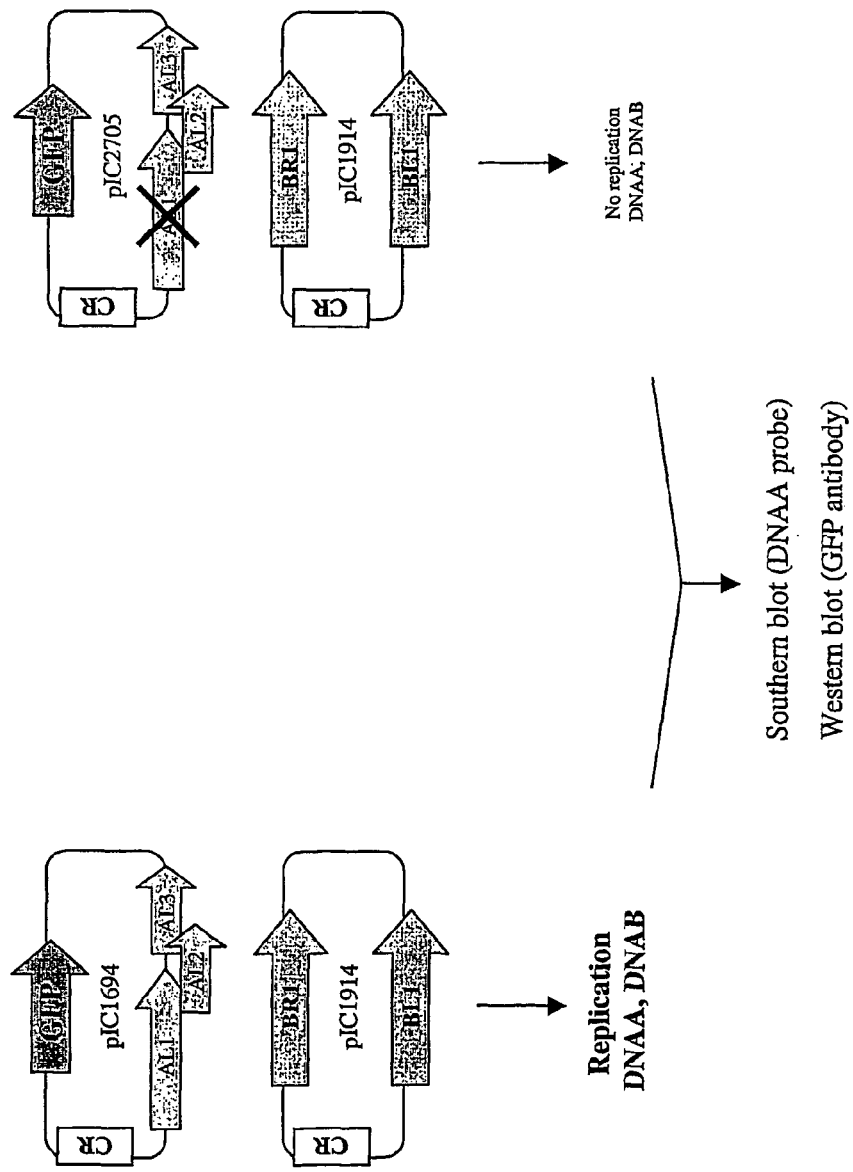

FIG. 2 depicts the scheme of experiment designed to test the ability of a geminivirus-based vector to replicate.

Figure 3:
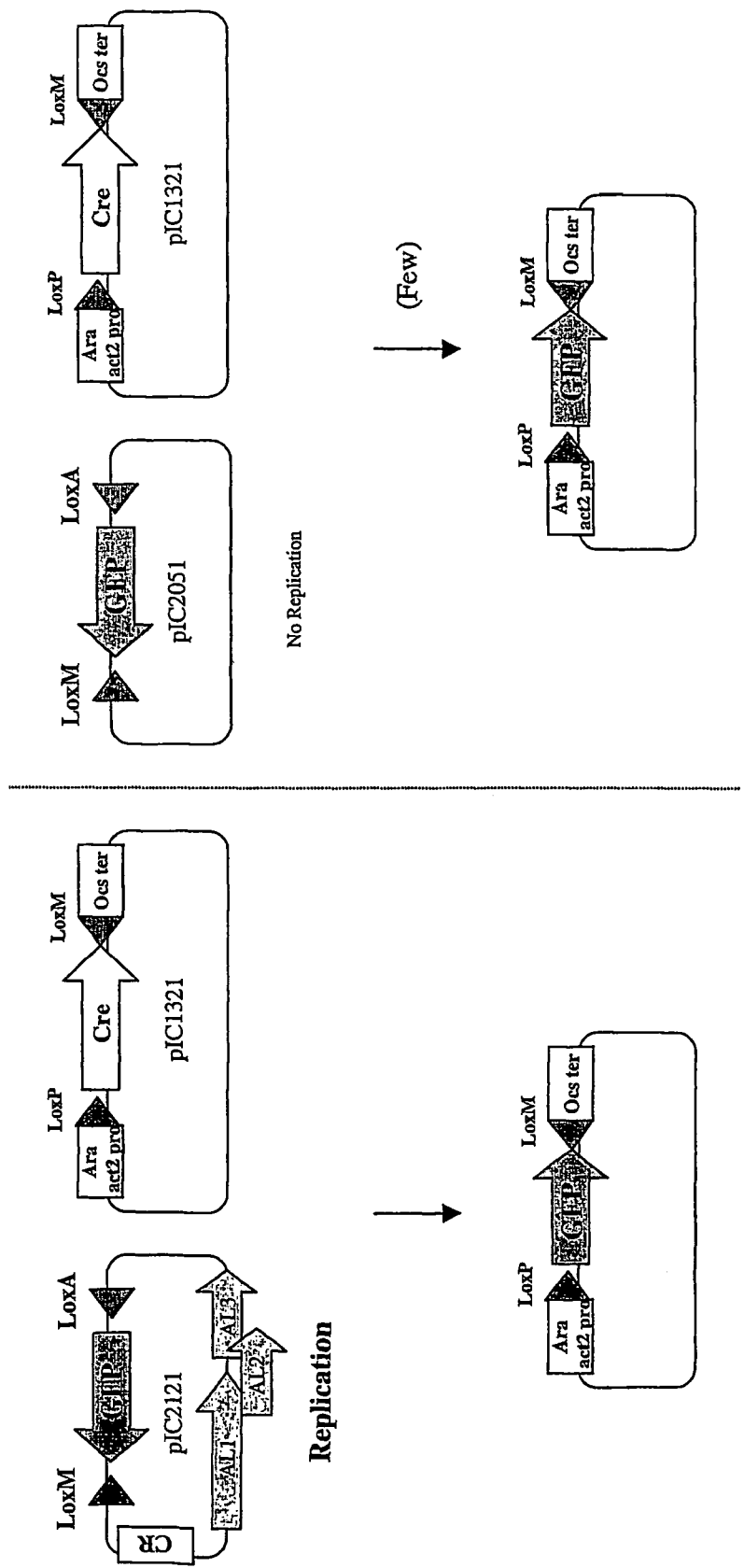

FIG. 3 depicts the scheme for comparing the efficiencies of site-specific recombination events using replicating and non-replicating vectors in transient expression experiments.

Figure 4:
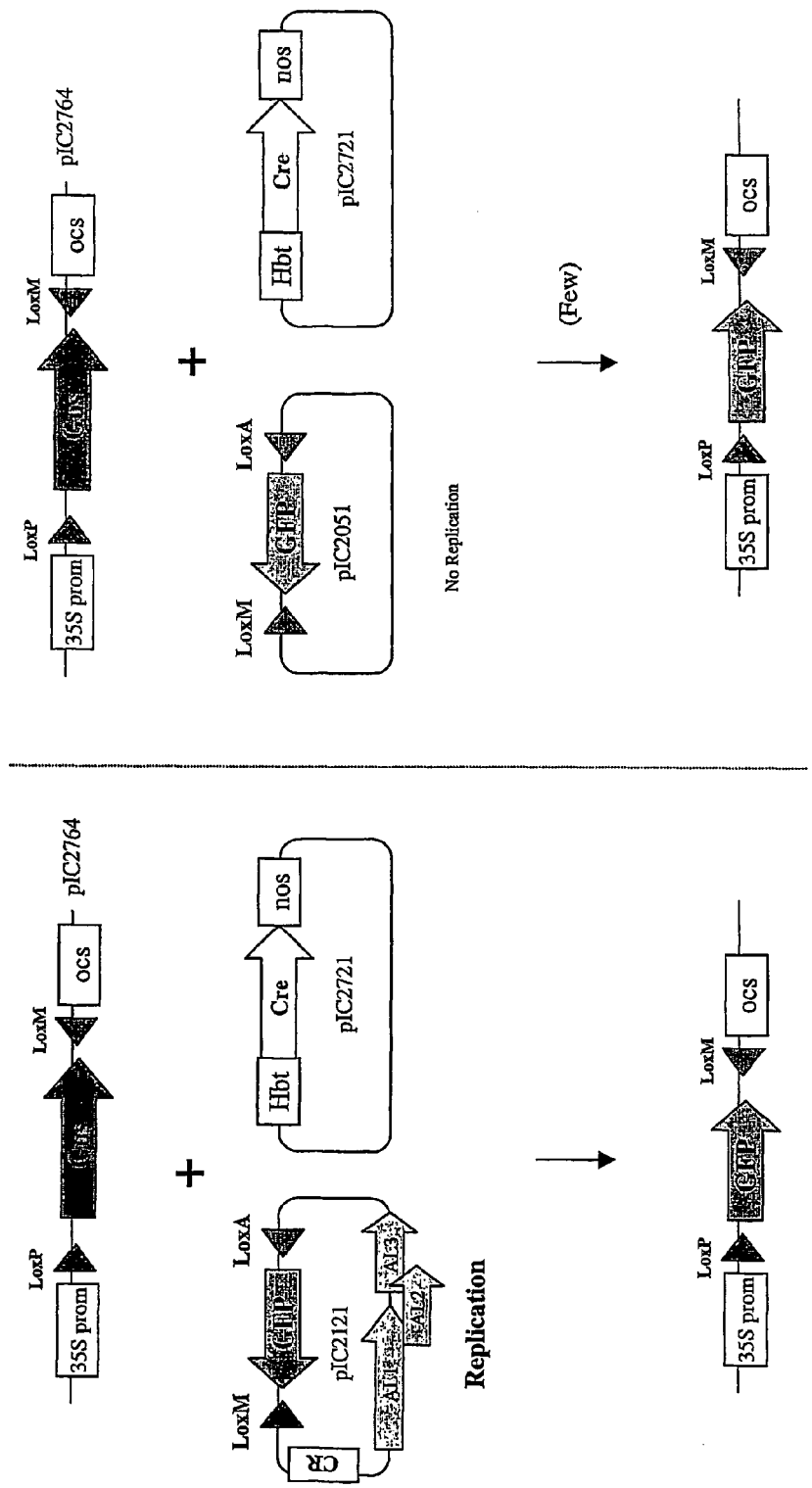

FIG. 4 depicts the scheme for comparing the efficiencies of site-directed recombination events in transgenic plant cells using replicating and non-replicating vectors with donor sequences of interest (GFP). Site-specific Cre recombinase is provided transiently from a non-replicating vector.

Figure 5:
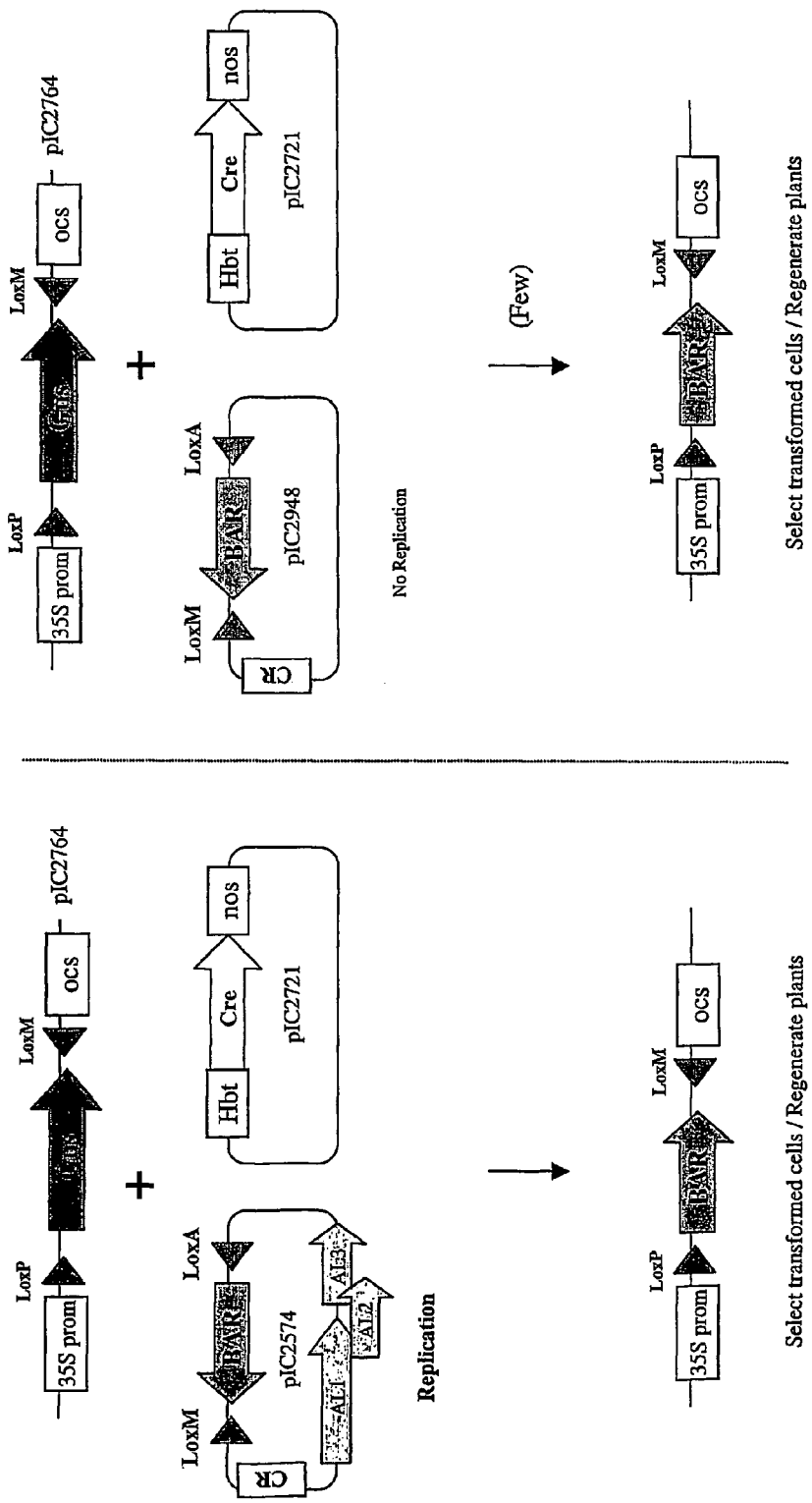

FIG. 5 depicts the scheme for comparing the efficiencies of site-directed recombination events in transgenic plant cells using replicating and non-replicating vectors with donor sequences of interest (BAR). Site-specific Cre recombinase is provided transiently from non-replicating vector.

Figure 6:
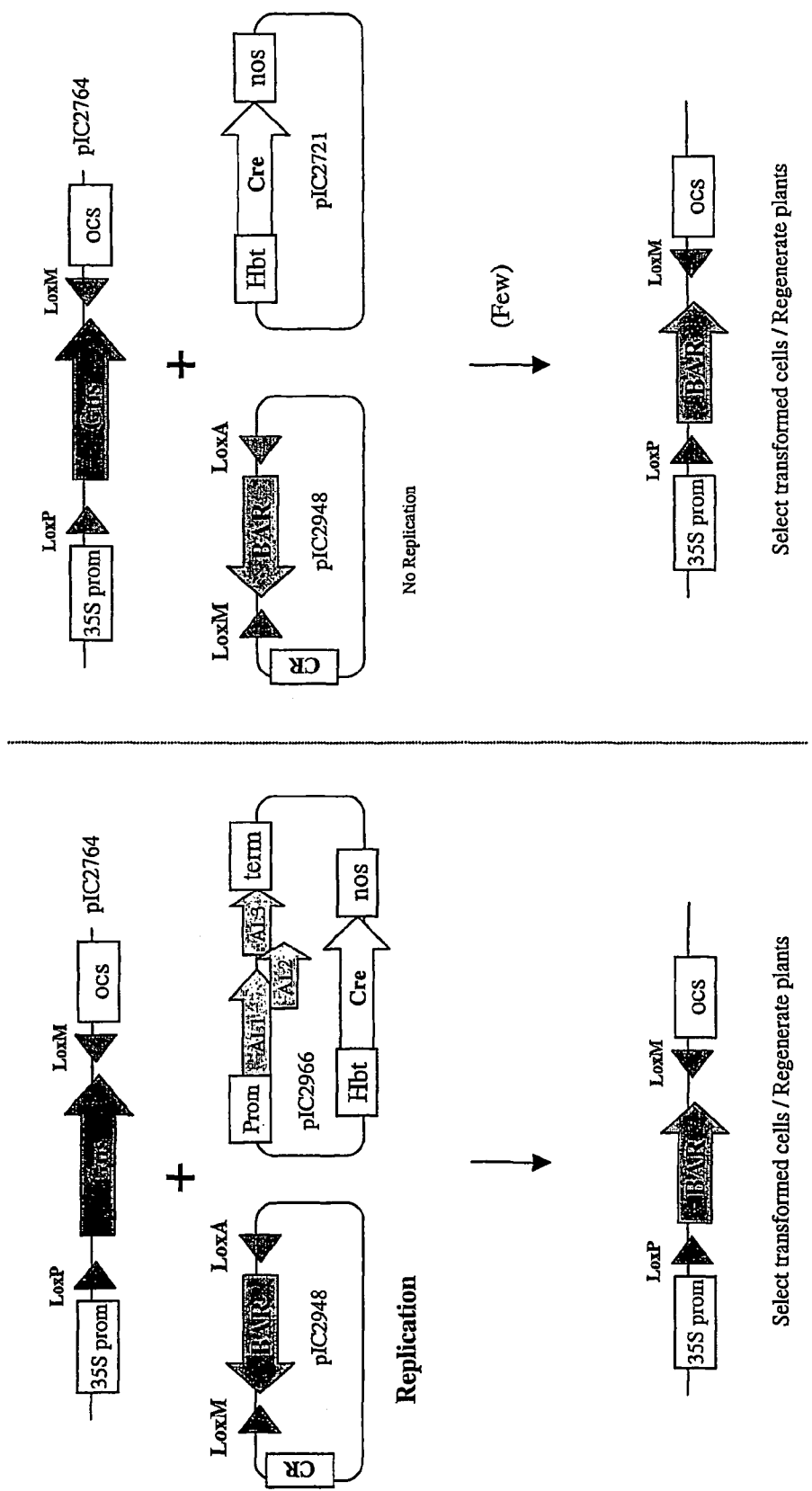

FIG. 6 depicts the scheme for comparing the efficiencies of site-directed recombination events in transgenic plant cells using replicating and non-replicating vectors with donor sequences of interest (BAR). Site-specific Cre recombinase is provided transiently together with replicase from a non-replicating vector.

Figure 7:
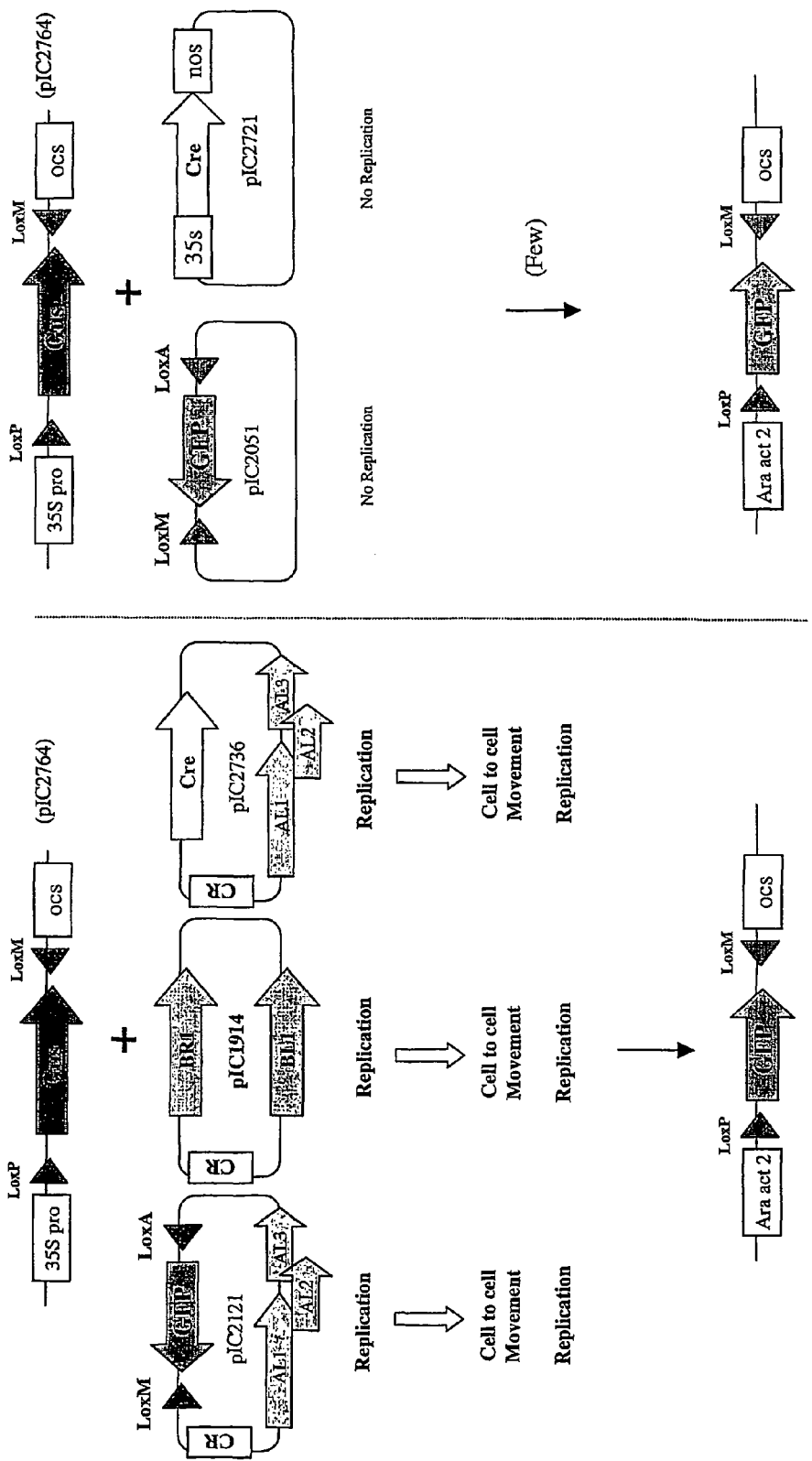

FIG. 7 depicts the scheme for comparing the efficiencies of site-directed recombination events in transgenic plant cells using replicating vectors with ability for cell-to-cell movement (due to the replication and movement of BGMV B genome) and non-replicating vectors with donor sequences of interest (GFP). Site-specific Cre recombinase is provided transiently from replicating or non-replicating vectors.

Figure 8:
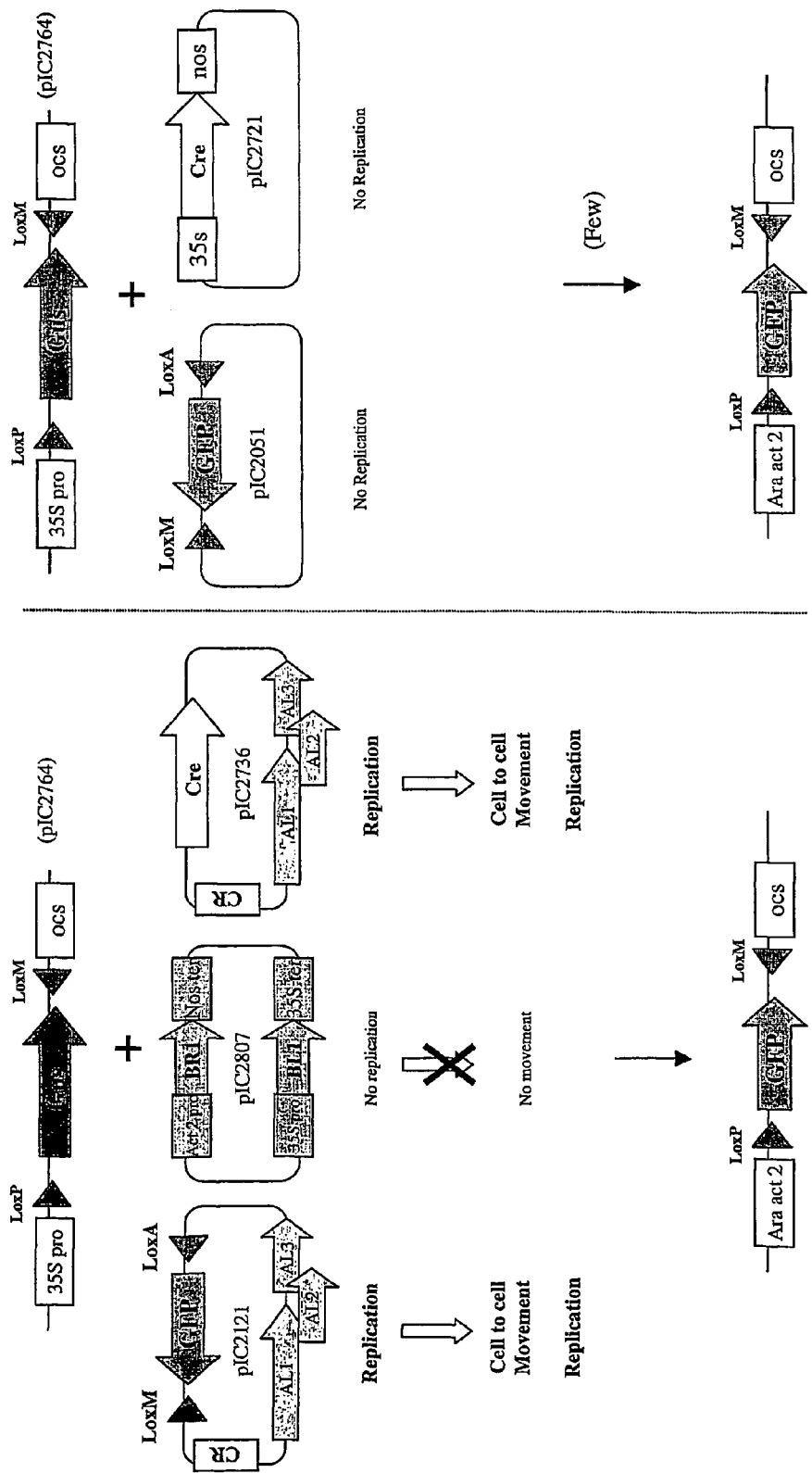

FIG. 8 depicts the scheme for comparing the efficiencies of site-directed recombination events in transgenic plant cells using replicating vectors with the ability for cell-to-cell movement (but BGMV B genome is unable to move) and non-replicating vectors with donor sequences of interest (GFP). Site-specific Cre recombinase is provided transiently from replicating or non-replicating vectors.

Figure 9:
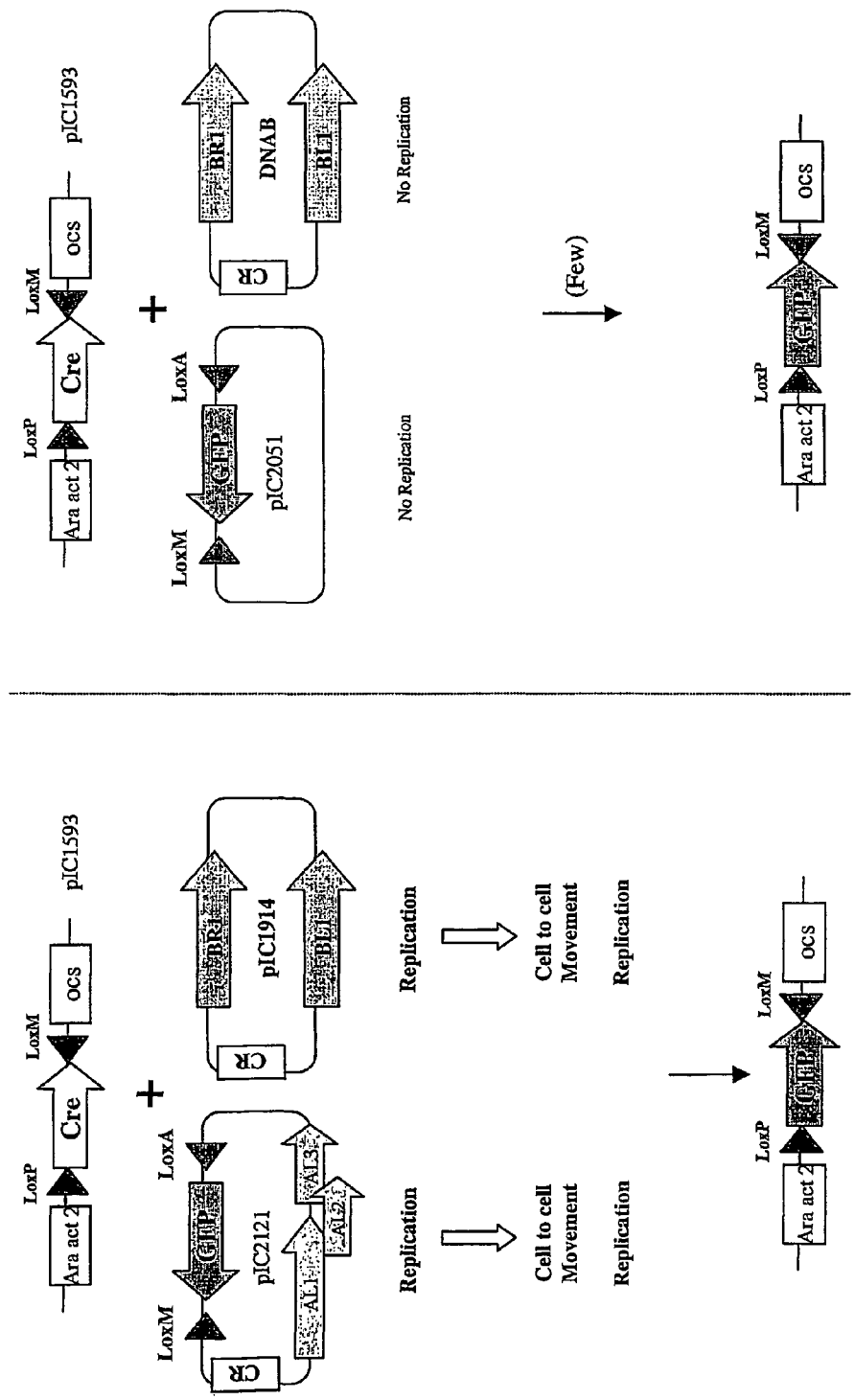

FIG. 9 depicts the scheme for comparing the efficiencies of site-directed recombination events in transgenic plant cells using replicating vectors that retain the ability for cell to cell movement (due to the replication and movement of BGMV B genome and non-replicating vectors with donor sequences of interest (GFP). Site-specific Cre recombinase is expressed by transgenic plant cells and is switched off as a result of site-directed recombination.

Figure 10:
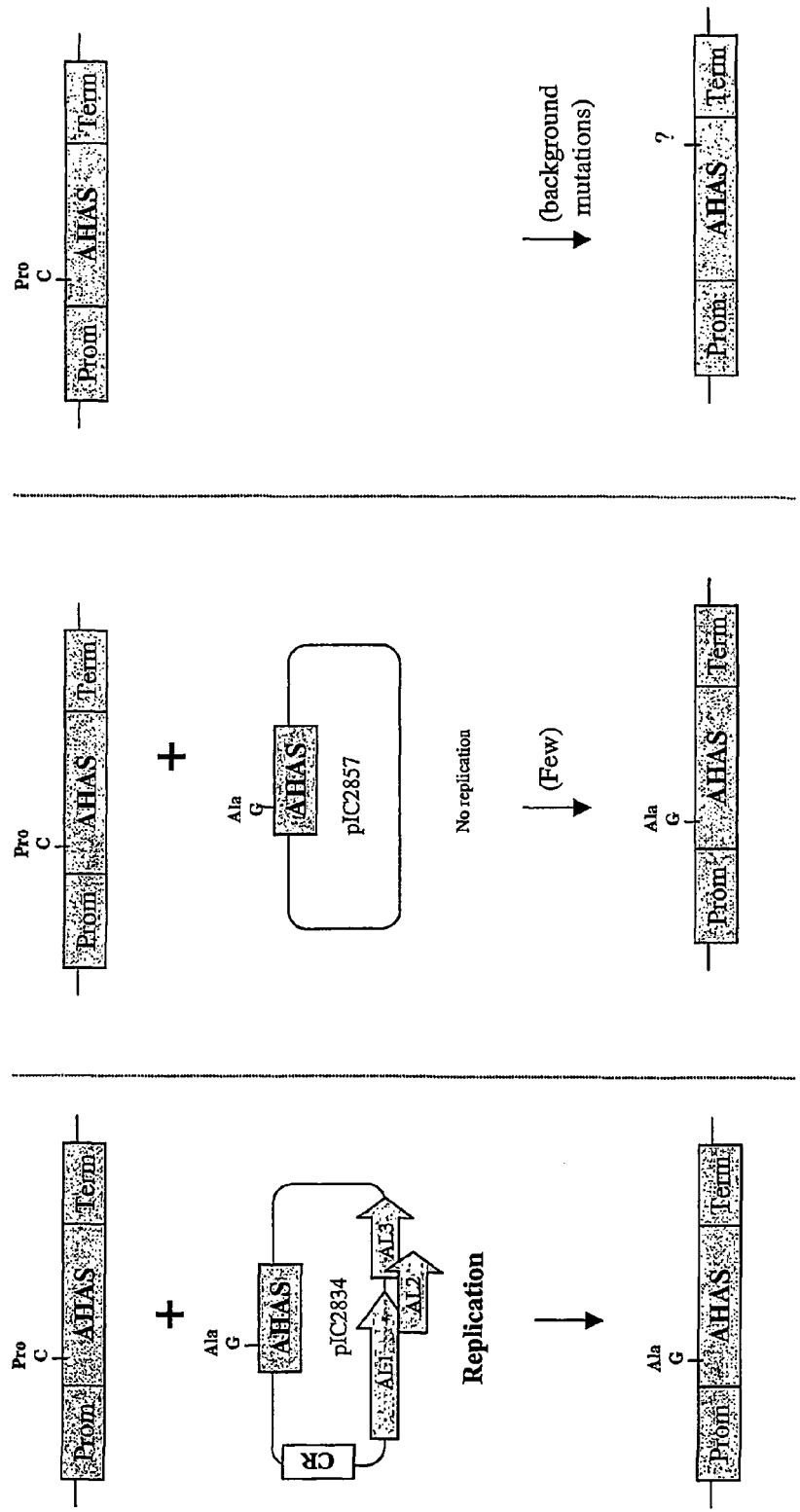

FIG. 10 depicts the scheme of experiments for site-directed mutagenesis by homolgous recombination using geminivirus-based replicating vector.

Figure 11:
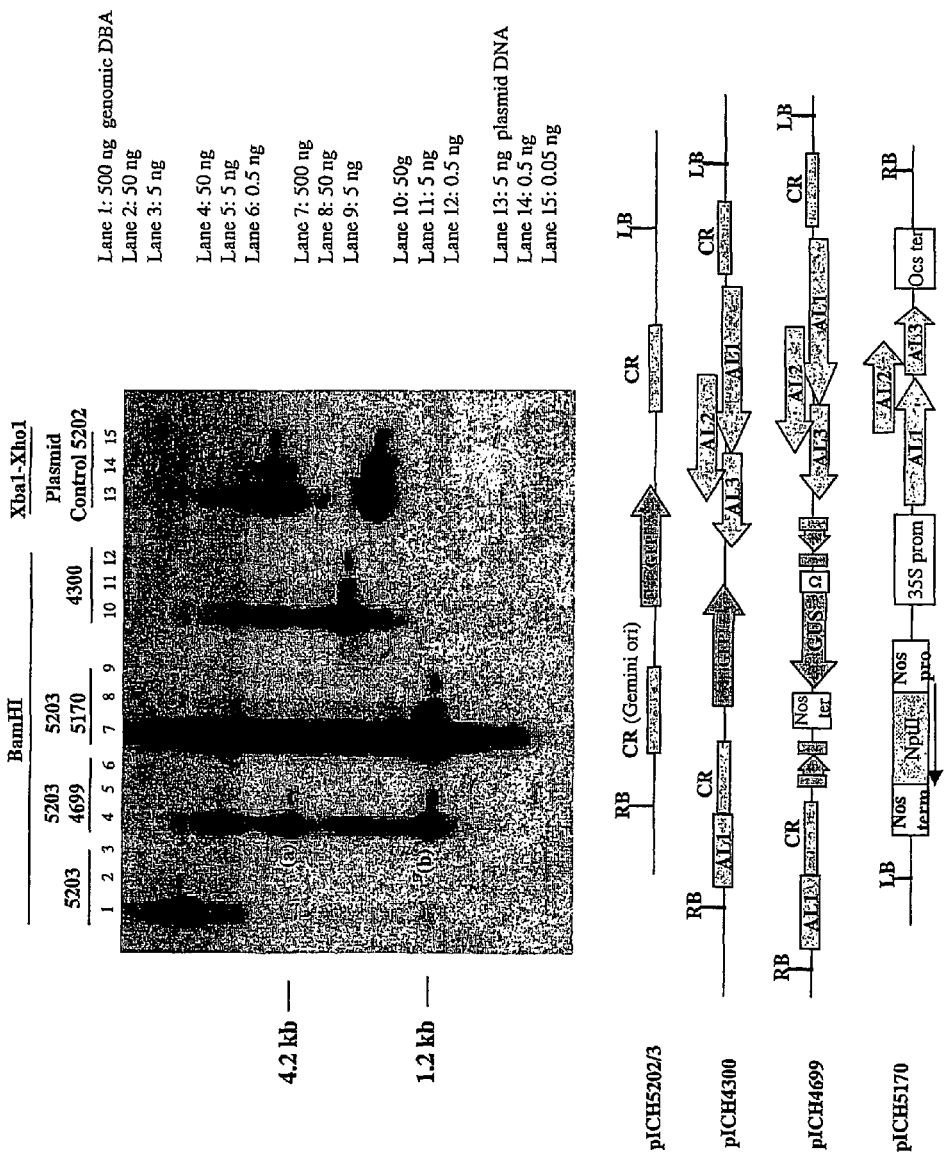

FIG. 11 depicts the T-DNA based constructs pICH5203, pICH4300, pICH4699, and pICH5170 made to demonstrate amplification of replicons with the replicase provided in trans and shows results of a Southern blot analysis.

Figure 12:
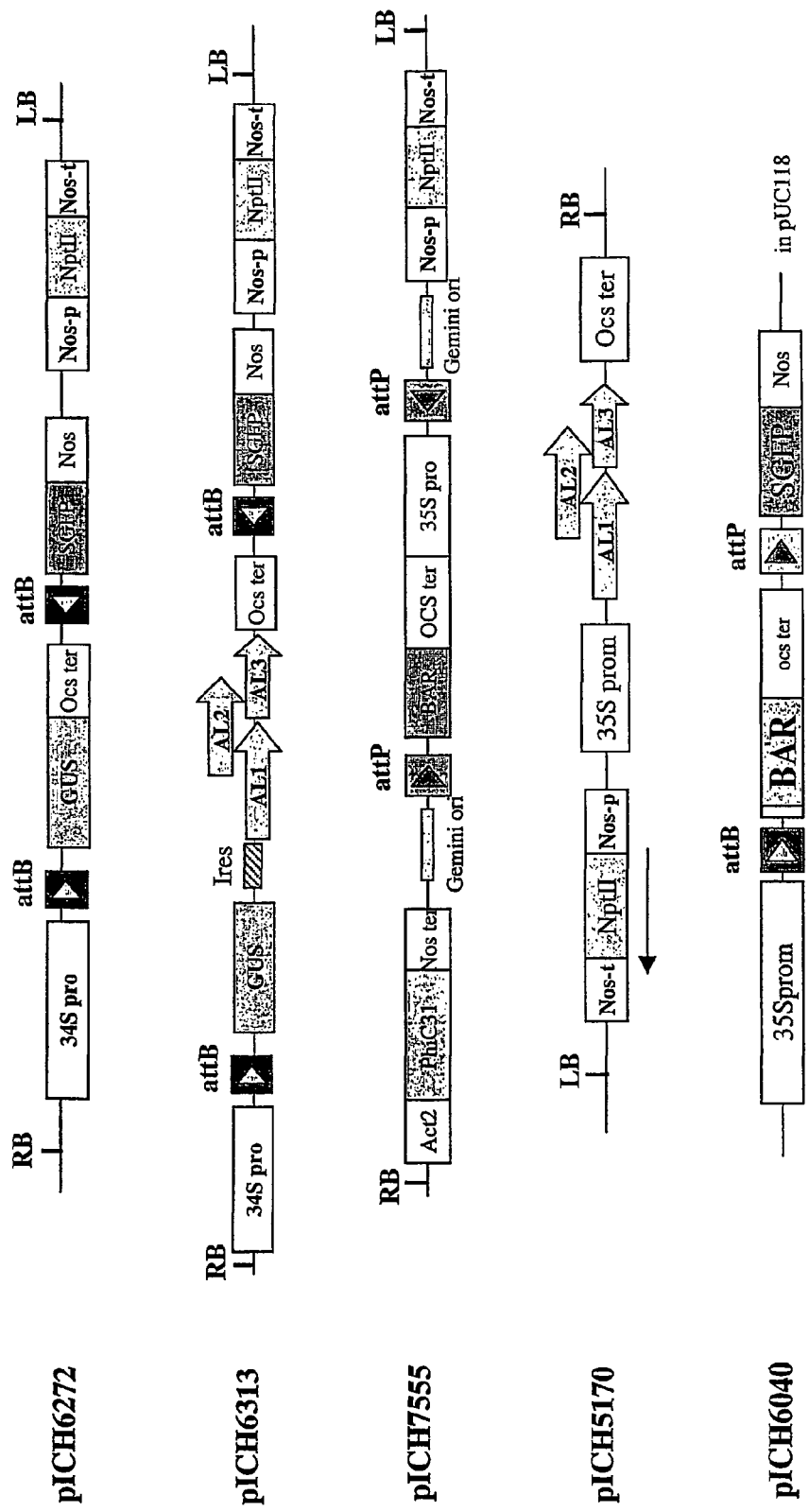

FIG. 12 depicts T-DNA based constructs pICH6272, pICH6313, pICH7555, pICH5170 and pICH6040 designed for site specific integration using the phage C31 integrase system.

Figure 13:
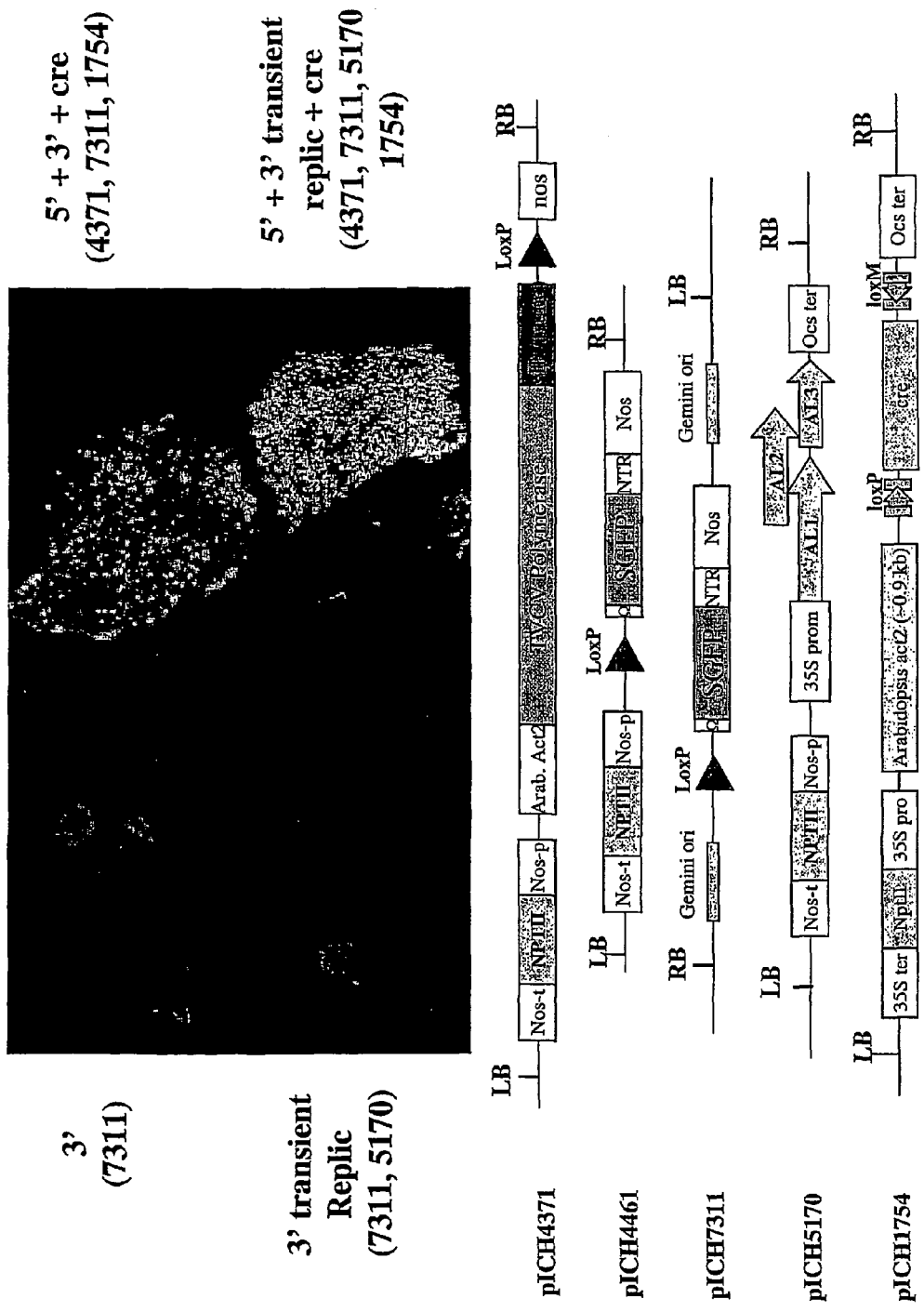

FIG. 13 depicts constructs pICH4371, pICH4461, pICH7311, pICH5170, and pICH1754 used to demonstrate increased site-specific recombination between 5' and 3' provectors using geminivirus-mediated 3' end provector amplification. Also, a picture of an infiltrated *N. benthamiana* leaf showing increased site-specific recombination is shown.

Figure 14:
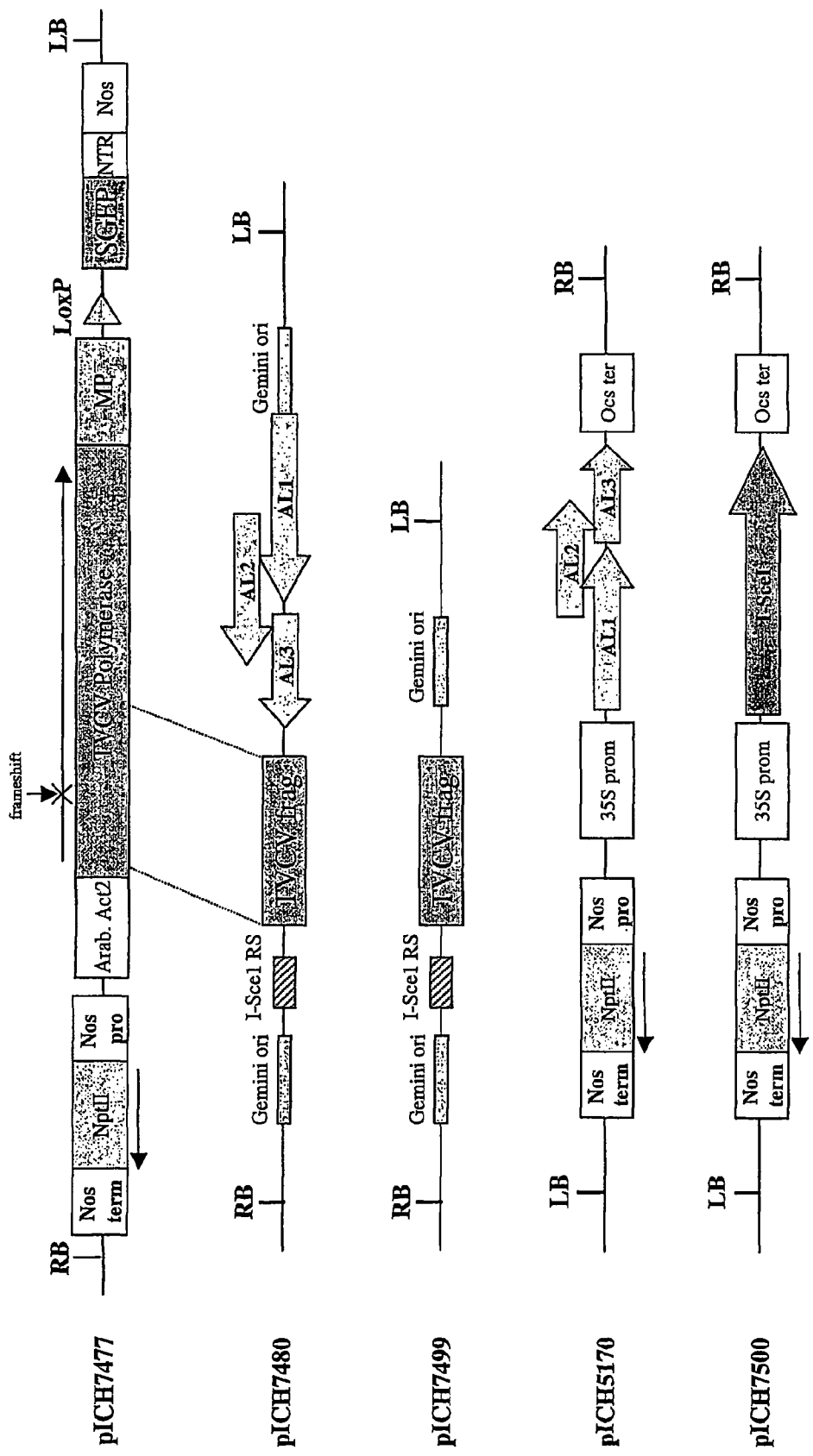

FIG. 14 depicts the T-DNA based constructs pICH7477, pICH7480, pICH7499, pICH5170, and pICH7500 designed for homologous recombination using pro-vector elements as the detection system of recombination events.

Appendices 1 to 16 depict vectors used in the examples section.

DETAILED DESCRIPTION OF THE INVENTION

The present invention describes the use of amplification vectors to increase the efficiency of targeted transformation in plants. Vectors capable of replication in a plant cell that amplify passenger DNA (DNA of interest) in cells into which the DNA has been delivered, are shown to greatly enhance the frequency of directed recombination. In addition, when the vectors used are derived from viral genomes and retain other viral capabilities such as cell-to-cell or long distance (systemic) movement, the passenger DNA to be targeted can be transported to adjacent cells and throughout the organism where it also replicates; the resulting targeted recombination effect amplifies even further. We have found that increased homologous recombination frequencies are obtained with replicating vectors at either natural or pre-engineered target sites using either the endogenous recombination machinery of the plant or heterologous site-specific recombination systems.

Figure 1:
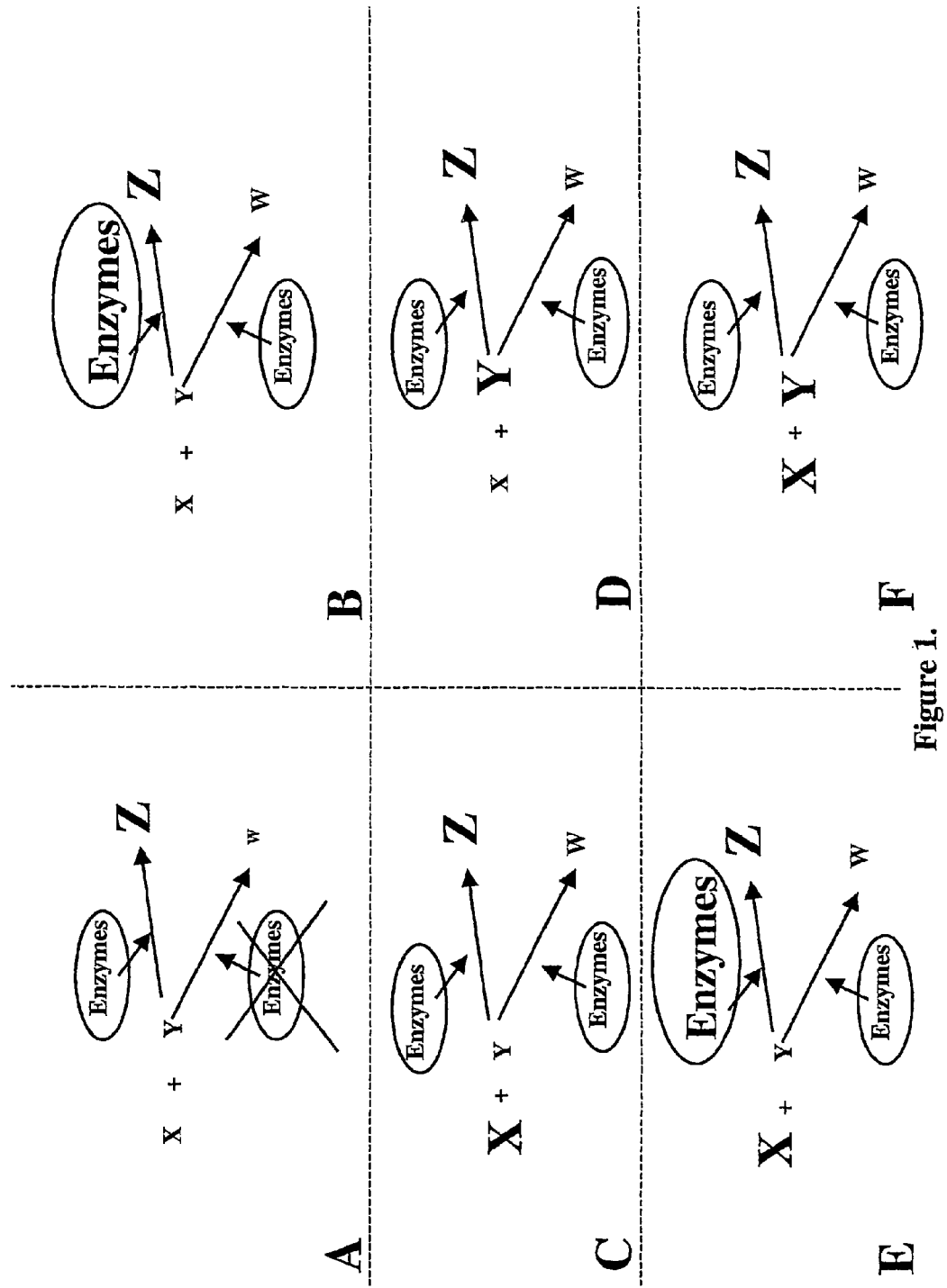
FIG. 1(A-F) shows six of many possible ways to increase the frequency of site-targeted or homologous recombination events in plant cells.

Irrespective of whether the incoming DNA needs to be recombined using the endogenous recombination machinery or heterologous site-specific recombinases, recombination theoretically involves a physical interaction between incoming DNA molecules and the target site. Therefore, it will be dependent on the relative concentrations of incoming and target DNA (Wilson et al., 1994, *Proc. Natl. Acad. Sci.*, 91, 177-181). This is particularly important when recombinases such as Cre are used, since the recombination reaction (which is bimolecular) takes place at a much lower rate than the excision reaction and sophisticated strategies (described above) have to be used to recover an insertion event. Different approaches already have been or can be undertaken (see FIG. 1). Our approach to modify the efficiency of site-specific recombination consists of using replicating vectors to amplify the DNA to be targeted with or without the increase of the concentration of an enzyme involved in homologous recombination. Optionally, expression of proteins involved in non-homologous recombination may additionally be suppressed. Amplification vectors are shown herein to replicate passenger DNA within the cells into which they are delivered. If virus-based amplicons (replicons) are used, the infection will spread to adjacent cells further improving the efficiency of targeted insertions. The unexpected outcome is an enormously increased targeted transformation frequency. The success of this approach was surprising, since a competing repair mechanism called non-homologous end-joining (NHEJ) also takes place at a high frequency in most higher plant species including all economically important crops. NHEJ is one of the reasons why selection for the desired site-targeted events diluted or hidden in a strong background of unwanted reactions is difficult in the prior art.

Targeted transformation according to this invention makes plant engineering a much more precise, controlled and efficient technology. It is broadly applicable and it allows to solve many current problems in plant genetic engineering including gene introduction duration, lack of control over gene activation, gene silencing, vector design limitations, single-step nature of current engineering processes, line conversion duration and associated linkage drag, etc. To our knowledge, there is no prior art for the use of amplification vectors for targeted transformation in plants.

Vectors Utilizing Plant Viral Amplicons

Geminiviruses are members of a large and diverse family of plant-infecting viruses characterized by twinned icosahedral capsids and circular, single-stranded DNA genomes (For reviews, see Timmermans et al., 1994, *Annu. Rev. Plant Physiol. Plant Mol. Biol.*, 45, 79-113; Mullineaux et al., 1992, in: Wilson, T. M. A., Davies, J. W. (Eds.) *Genetic Engineering with Viruses*, CRC Press, Boca Raton, Fla., 187-215; Palmer & Rybicki, 1997, *Plant Science*, 129, 115-130). Geminiviruses can be generally classified into two subgroups (with the exception of a few atypical geminiviruses):

(i) monopartite geminiviruses which have a single component genome, infect monocotyledonous plants and are transmitted by leafhoppers, and (ii) bipartite geminiviruses whose genome is composed of two circular genomes, infect dicotyledonous plants and are transmitted by whiteflies.

Some examples of monopartite geminiviruses include the maize streak virus (MSV), the wheat dwarf virus (WDV), the *Digitaria* streak virus (DSV), and the *Miscanthus* streak virus (MiSV). Examples of bipartite geminiviruses include the tomato golden mosaic virus (TGMV), the bean golden mosaic virus (BGMV), the African cassava mosaic virus (ACMV), and the *abutilon* mosaic virus (AbMV).

Geminiviruses replicate their genomes using a rolling-circle mechanism similar to that used by ssDNA containing coli phages (e.g. PhiX174) (Saunders et al., 1991, *Nucl. Acids. Res.*, 19, 2325-2330; Stenger et al., 1991, *Proc. Natl. Acad. Sci.*, 88, 8029-8033). A consequence of this mode of replication is the generation of double-stranded DNA genomes as replication intermediates. These double-stranded DNA genomes behave essentially as high copy plant plasmids and can be present at extremely high copy numbers of up to 30000 copies per nucleus of infected cell (Kanevski et al., 1992, *Plant J.*, 2, 457-463; Timmermans et al., 1992, *Nucl. Acids Res.*, 20, 4047-4054). These characteristics and the fact that, collectively, geminiviruses have a very broad host range, has stimulated a lot of research in developing geminiviruses as replicating vectors for plants, mainly to enhance levels of transgene expression or to develop resistance strategies against geminiviral diseases. Several patents have been issued which describe the use of replicating geminivirus vectors for enhancing gene expression in plants (U.S. Pat. No. 5,981,236, WO020557A2, U.S. Pat. No. 6,110,466, U.S. Pat. No. 6,147,278, U.S. Pat. No. 6,077,992), for developing plant disease resistance strategies (some examples are U.S. Pat. No. 6,118,048, WO9739110A1, U.S. Pat. No. 6,133,505, U.S. Pat. No. 6,087,162), or for suppressing gene expression in plants (WO9950429A1).

There are several publications that describe attempts of combined use of geminivirus vectors and transposons to achieve transposition and transformation of genomes of monocots (Laufs et al., 1990, *Proc. Natl. Acad. Sci. USA.*, 87, 7752-7756; Shen & Hohn, 1992, *Plant J.*, 2, 35-42; Sugimoto et al., 1994, *Plant J.*, 5, 863-871). One publication reports the use of geminiviruses as amplification vectors to increase transformation frequency (Sugimoto et al., 1994, *Plant J.*, 5, 863-871). This works is inspired by a *Drosophila* transformation method which is based on transposition of P elements from introduced DNA molecules to chromosomal DNA. The authors cloned a Ds element and the Ac transposase in separate geminivirus *miscanthus* streak virus (MiSV) vectors and co-bombarded rice protoplasts with these vectors. After excision, a low frequency of reinsertion (in the order of $10^{-5}$) led to the recovery of five chromosomal insertion events. No transposition event could be detected in a control non-replicating vector, indicating that replication was required to recover reinsertion events due to the low transposition frequency. This approach differs from our invention by the non-targeted nature of the resulting transformation events.

The present invention preferably uses replicons as amplification vectors (replicons are freely replicating circular DNA molecules, the use of which is described in many publications, see reviews: Timmermans et al., 1994, *Annu. Rev. Plant. Physiol. Plant Mol. Biol.*, 45, 79-113; Mullineaux et al., 1992, in: Wilson, T. M. A., Davies, J. W (Eds.) *Genetic Engineering with Viruses*, CRC Press, Boca Raton, Fla., 187-215; Palmer & Rybicki, 1997, *Plant Science*, 129, 115-130). Replicons contain a geminivirus origin of replication and preferably a DNA sequence of interest. Replication is mediated by the geminiviral replicase which can be present either on the replicon itself, on a co-transformed replicating or non-replicating plasmid, or it may be expressed from a stably transformed expression cassette integrated into a chromosome. Replicons may be cloned in bacteria in the form of pre-replicons. Replicons may be released from pre-replicons by either one of two approaches: (i) by digesting the pre-replicon with an enzyme that will release replicon DNA from a plasmid vector or (ii) by using pre-replicons containing more than one unit length of genome. In the first approach, excised DNA will recircularize after its introduction into cells using an endogenous ligase (Bisaro et al., 1983, *Nucl. Acids. Res.*, 11, 7387-96). In the second approach, circular replicons are released from pre-replicons by homologous intramolecular recombination in duplicated sequences or by a replicational release mechanism (provided that two origins of replication are present in the pre-replicon) (Stenger et al., 1991, *Proc. Natl. Acad. Sci.*, 88, 8029-8033; Rogers et al., 1986, *Cell*, 45, 593-600). A pre-replicon contains a replicon in its continuity and replicon formation is the process of release of said continuity from flanking sequences of said pre-replicon. Replicon(s) can also be formed in a plant host from precursor vector(s) or pro-vector(s). Precursor vector(s) or pro-vector(s) are nucleic acids, which upon processing in plant host form vector(s) that are able to amplify and express heterologous nucleic acid sequence(s) in said host. Said processing includes formation of continuity from discontinued vector parts.

Replicons can be introduced into plant cells by a variety of mechanisms including *Agrobacterium*-mediated transformation, electroporation, particle delivery or any other DNA delivery technology. Alternatively, the replicon can be released from a pre-replicon integrated in a chromosome. Pre-replicons in these constructs will contain two origins of replication so as to facilitate release of replicons by a replicative release mechanism. Release of the replicon and replication will be controlled by expression of the replicase. It will therefore be useful to be able to control the timing of expression by using an inducible or tissue-specific promoter in order to minimize the potential detrimental effect of replicon replication on cell survival.

Although geminivirus-based amplification vectors are preferred for performing this invention, other vectors capable of amplification in plant cells may also be used for this invention.

Both RNA- and DNA-containing viruses could be used for the construction of replicating vectors, and examples of different viruses are given in the following list:

DNA Viruses:
Circular dsDNA Viruses: Family: Caulimoviridae, Genus: Badnavirus, Type species: commelina yellow mottle virus, Genus: Caulimovirus Type species: cauliflower mosaic virus, Genus "SbCMV-like viruses", Type species: Soybean chloroticmottle virus, Genus "CsVMV-like viruses", Type species: Cassaya vein mosaicvirus, Genus "RTBV-like viruses", Type species: Rice tungro bacilliformvirus, Genus: "Petunia vein clearing-like viruses", Type species: Petunia vein clearing virus;

Circular ssDNA Viruses: Family: Geminiviridae, Genus: Mastrevirus (Subgroup I Geminivirus), Type species: maize streak virus, Genus: Curtovirus (Subgroup II Geminivirus), Type species: beet curly top virus, Genus: Begomovirus (Subgroup III Geminivirus), Type species: bean golden mosaic virus;

RNA Viruses:

ssRNA Viruses: Family: Bromoviridae, Genus: Alfamovirus, Type species: alfalfa mosaic virus, Genus: Ilarvirus, Type species: tobacco streak virus, Genus: Bromovirus, Type species: brome mosaic virus, Genus: Cucumovirus, Type species: cucumber mosaic virus;

Family: Closteroviridae, Genus: Closterovirus, Type species: beet yellows virus, Genus: Crinivirus, Type species: Lettuce infectious yellows virus, Family: Comoviridae, Genus: Comovirus, Type species: cowpea mosaic virus, Genus: Fabavirus, Type species: broad bean wilt virus 1, Genus: Nepovirus, Type species: tobacco ringspot virus;

Family: Potyviridae, Genus: Potyvirus, Type species: potato virus Y, Genus: Rymovirus, Type species: ryegrass mosaic virus, Genus: Bymovirus, Type species: barley yellow mosaic virus;

Family: Sequiviridae, Genus: Sequivirus, Type species: parsnip yellow fleck virus, Genus: Waikavirus, Type species: rice tungro spherical virus; Family: Tombusviridae, Genus: Carmovirus, Type species: carnation mottle virus, Genus: Dianthovirus, Type species: carnation ringspot virus, Genus: Machlomovirus, Type species: maize chlorotic mottle virus, Genus: Necrovirus, Type species: tobacco necrosis virus, Genus: Tombusvirus, Type species: tomato bushy stunt virus, Unassigned Genera of ssRNA viruses, Genus: Capillovirus, Type species: apple stem grooving virus;

Genus: Carlavirus, Type species: carnation latent virus; Genus: Enamovirus, Type species: pea enation mosaic virus, Genus: Furovirus, Type species: soil-borne wheat mosaic virus, Genus: Hordeivirus, Type species: barley stripe mosaic virus, Genus: Idaeovirus, Type species: raspberry bushy dwarf virus;

Genus: Luteovirus, Type species: barley yellow dwarf virus; Genus: Marafivirus, Type species: maize rayado fino virus; Genus: Potexvirus, Type species: potato virus X; Genus: Sobemovirus, Type species: Southern bean mosaic virus, Genus: Tenuivirus, Type species: rice stripe virus, Genus: Tobamovirus, Type species: tobacco mosaic virus, Genus: Tobravirus, Type species: tobacco rattle virus, Genus: Trichovirus, Type species: apple chlorotic leaf spot virus; Genus: Tymovirus, Type species: turnip yellow mosaic virus; Genus: Umbravirus, Type species: carrot mottle virus; Negative ssRNA Viruses: Order: Mononegavirales, Family: Rhabdoviridae, Genus: Cytorhabdovirus, Type Species: lettuce necrotic yellows virus, Genus: Nucleorhabdovirus, Type species: potato yellow dwarf virus;

Negative ssRNA Viruses: Family: Bunyaviridae, Genus: Tospovirus, Type species: tomato spotted wilt virus;

dsRNA Viruses: Family: Partitiviridae, Genus: Alphacryptovirus, Type species: white clover cryptic virus 1, Genus: Betacryptovirus, Type species: white clover cryptic virus 2, Family: Reoviridae, Genus: Fijivirus, Type species: Fiji disease virus, Genus: Phytoreovirus, Type species: wound tumor virus, Genus: Oryzavirus, Type species: rice ragged stunt virus;

Unassigned Viruses: Genome ssDNA: Species: banana bunchy top virus, Species coconut foliar decay virus, Species: subterranean clover stunt virus, Genome: dsDNA, Species: cucumber vein yellowing virus; Genome: dsRNA, Species: tobacco stunt virus, Genome: ssRNA, Species Garlic viruses A,B,C,D, Species grapevine fleck virus, Species maize white line mosaic virus, Species olive latent virus 2, Species: ourmia melon virus, Species Pelargonium zonate spot virus;

Satellites and Viroids: Satellites: ssRNA Satellite Viruses: Subgroup 2 Satellite Viruses, Type species: tobacco necrosis satellite, Satellite RNA, Subgroup 2 B Type mRNA Satellites, Subgroup 3C Type linear RNA Satellites, Subgroup 4 D Type circular RNA Satellites, Viroids, Type species: potato spindle tuber viroid.

Mostly, vectors of plant viral origin are used as plasmids capable of autonomous replication in plants, but the principles necessary for engineering such plasmids using non-viral elements are known. For example, many putative origins of replication from plant cells have been described (Berlani et al., 1988, *Plant Mol. Biol.*, 11, 161-162; Hernandes et al., 1988, *Plant Mol. Biol.*, 10, 413-422; Berlani et al., 1988, *Plant Mol. Biol*, 11, 173-182; Eckdahl et al., 1989, *Plant Mol. Biol.*, 12, 507-516). It has been shown that the autonomously replicating sequences (ARS elements) from genomes of higher plants have structural and sequence features in common with ARS elements from yeast and higher animals (Eckdahl et al., 1989, *Plant Mol. Biol*, 12, 507-516). The plant ARS elements are capable of conferring autonomous replicating ability to plasmids in *Saccharomyces cerevisiae*. Studies of maize nuclear DNA sequences capable of promoting autonomous replication of plasmids in yeast showed that they represent two families of highly repeated sequences within the maize genome. Those sequences have characteristic genomic hybridization pattern. Typically there was only one copy of an ARS-homologous sequence on each 12-15 kb of genomic fragment (Berlani et al., 1988, *Plant Mol. Biol.*, 11:161-162). Another source of replicons of plant origin are plant ribosomal DNA spacer elements that can stimulate the amplification and expression of heterologous genes in plants (Borisjuk et al., 2000, *Nature Biotech.*, 18, 1303-1306).

Therefore, an amplification vector contemplated in this invention is not necessarily derived from a plant virus. Similarly, plant DNA viruses provide an easy way of engineering amplification vectors that could be especially useful for targeted DNA transformation, but vectors made entirely or partially of elements from plant RNA viruses or even non-plant viruses are possible. Advantages of plant-virus based vectors are evident. Such vectors, in addition to amplification, may provide additional useful functions such as cell-to-cell and long distance movement. Further, they can frequently more easily removed from the plant cell aposteriori by using known methods of virus eradication from infected plants.

In the present invention, replicons are preferably used to increase the copy number of a desired target sequence in the nuclei of the host cells. In one embodiment of this invention, recombination with a target site will occur by the intermediate of specific recombination sites placed on the replicon and at the target site. In another embodiment, recombination will occur as a result of homologous recombination between sequences carried by the replicon and homologous sequences in the host genome. Details of the vectors and uses of these vectors are described next.

Replicons Containing Recombination Sites from Heterologous Recombination Systems Suitable recombinases/recombination site systems include inter alia the Cre-Lox system from bacteriophage P1 (Austin et al., 1981, *Cell,* 25, 729-736), the Flp-Frt system from *Saccharomyces cerevisiae* (Broach et al., 1982, *Cell,* 29, 227-234), the R-Rs system from *Zygosaccharomyces rouxii* (Araki et al., 1985, *J. Mol. Biol.,* 182, 191-203), the integrase from the *Streptomyces* phage PhiC31 (Thorpe & Smith, 1998, *Proc. Natl. Acad. Sci.,* 95, 5505-5510; Groth et al., 2000, *Proc. Natl. Acad. Sci.,* 97, 5995-6000), and resolvases. One or two recombination sites may be present on the replicon. When a single site is present, recombination will lead to integration of the entire replicon at the target site including geminiviral sequences (one-sided recombination). Preferably, two recombination sites flanking the DNA to be targeted are therefore employed (two-sided recombination). Upon expression of the recombinase, recombination of the two sites with compatible sites at the target locus will lead to the replacement of the DNA sequence located between the recombination sites at the target locus by the DNA sequence of interest on the replicon. Selection for targeted events can easily be accomplished e.g. by including a promoterless selection marker on the DNA fragment to be targeted and a promoter at the target site. Recombination will then result in activation of the selectable marker gene by placing it under the control of the promoter at the target site, thus establishing a functional marker. The opposite strategy wherein a promoterless selectable marker is present at the target site and a promoter on the replicon is also possible.

When two recombination sites are present on the replicon, it is advantageous that these sites do not recombine with each other since this may delete the sequence of interest during replication of the replicon. Pairs of recombination sites that cannot recombine with each other have been described for the Cre-Lox and Flp/Frt systems. Such sites, called heterospecific sites, contain mutations in the central core region. These sites can recombine at wild-type level with sites identical to them but not with different heterospecific sites (Bethke & Sauer, 1997, *Nucl. Acids Res.,* 25, 2828-2834, see also example 2). Recombination sites of some systems, such as the PhiC31 integrase cannot recombine with identical sites, but only with different compatible sites. For example, in the presence of the PhiC31 integrase, attP sites recombine with an attB sites, thus producing attL and attR. attP or attB sites may be used on the replicon, while compatible sites may be placed at the target sites on the genome.

Target sites in the plant nuclear genome may be naturally occurring (resident genes to be targeted, sequences recognized by heterologous site-specific recombinases, restriction enzymes, etc.) or pre-engineered and introduced into the plant genome using existing technologies. Various methods may be used for the delivery of such sites into plant cells such as direct introduction of a vector into the plant cell by means of microprojectile bombardment (U.S. Pat. No. 05,100,792; EP 00444882B1; EP 00434616B1), electroporation (EP00564595B1; EP00290395B1; WO 08706614A1) or PEG-mediated treatment of protoplasts. These three methods may be summarized as non-biological delivery methods. *Agrobacterium*-mediated plant transformation (U.S. Pat. No. 5,591,616; U.S. Pat. No. 4,940,838; U.S. Pat. No. 5,464,763) also presents an efficient way of vector delivery. In principle, other plant transformation methods may also be used such as microinjection (WO 09209696; WO 09400583A1; EP 175966B1). The choice of the transformation method depends on the kind of plant species to be transformed. For example, for monocot transformation, the microprojectile bombardment is preferable, while for dicots, *Agrobacterium*-mediated transformation gives better results in general. The same methods may be used for transfecting or transforming a plant cell with an amplification vector or for said providing a plant cell with DNA. Moreover, this may be achieved by viral transfection or by using a vector or pro-vector that was pre-integrated into the plant nuclear DNA to form an autonomously replicating plasmid.

An appropriate heterologous recombinase may be expressed either from the replicon, from a co-transformed replicating or non-replication plasmid, or it may be expressed from the chromosomal target site. Its expression can be made constitutive, tissue-specific or inducible. Various possibilities are illustrated in the examples section below.

Bipartite geminiviruses have two genome components, DNAA and DNAB. The B genome encodes two genes whose products are required for cell-to-cell and systemic movement of both genome components (Brough et al., 1988, J. Gen. Virol., 69, 503-514; Qin et al., J. Virol., 72, 9247-9256). An example is the DNAB genome of BGMV, which encodes two open reading frames, BL1 and BR1. Expression of genes encoded on the B genome will allow replicons to move from cell to cell or systemically. Both genes may be provided by co-transforming a construct from which a wild-type B genome will be released. Alternatively, B genes can be provided on a non-replicating plasmid. In this way, genes of the B genome may be expressed transiently until the non-replicating plasmid disappears from the cell. This is advantageous as expression of the genes of the B genome and in particular BL1 is responsible for the disease symptoms of geminivirus-infected plants (Pascal et al., 1993, *Plant Cell,* 5, 795-807). It has also been shown that transient expression of genes encoded by the B genome is sufficient for systemic movement of the DNAA genome for TGMV (Jeffrey et al., 1996, *Virology,* 223, 208-218).

Replicons Carrying Sequences with Homology to Endogenous Sequences

Replication of replicons containing DNA sequence(s) which are homologous to endogenous sequences will increase recombination with homologous target sequences. Homologous recombination is preferably initiated by double strand breaks or nicks in DNA. Geminiviral DNA is present in cells in different forms including supercoiled double-stranded circular, open-circular, and linear DNA (Saunder et al., 1991, *Nucl. Acids Res.,* 19, 2325-2330). Nicks in open-circular DNA and double strand breaks on linear DNA will induce homologous recombination events. To further increase recombination, it is also possible to induce the formation of double strand breaks in replicated DNA by placing on the replicon one or two restriction sites for a rare cutting enzyme such as the yeast HO or I Sce-I endonucleases. The endonuclease can be expressed from a co-transformed replicating or non-replicating plasmid or from a stably integrated expression cassette integrated in a chromosome. Its expression can be constitutive, tissue-specific or inducible.

The vector used in this invention may be a pro-vector. A pro-vector is a vector from which a vector according to the invention is generated within a plant cell by the plant nucleid acid processing machinery, e.g. by intron splicing.

EXAMPLES

The following examples demonstrate, inter alia, the detection of site-targeted integration events at increased frequency due to replicating amplification vectors. Further, examples for successful selection of progeny cells and recovery of transformants preferably using transiently replicating amplification vectors are given.

Example 1

This example reports the cloning of replicating clones of BGMV DNAA and DNAB genomes (FIG. 2).
Cloning of a DNAA Genome Replicating Vector Containing GFP:

pUC19 DNA was amplified with primers dnaapr7 (aac tgc agt cta gac tgg ccg tcg ttt tac aac) and dnaapr8 (aac tgc aga aca att gct cga ggc gta atc atg gtc a), and the amplified fragment digested with Pst1 and religated. The resulting plasmid, pIC1144, is similar to pUC19, but the polylinker has been replaced with Xho1, MfeI, and Pst1. DNA was extracted from *Phaseolus vulgaris* tissue infected by bean golden mosaic virus (BGMV) isolate DSMZ PV-0094 obtained from the German Collection of Microorganisms and Cell Cultures (DSMZ, Deutsche Sammlung von Mikroorganismen und Zelikulturen GmbH). A fragment of the genome encompassing the BGMV common region. (CR; contains the BGMV origin of replication) was amplified by PCR with primers dnaapr3 (ggg aat tca cta gta aag atc tgc cgt cga ctt gga att g) and dnaapr4 (caa tgc atc atg gcg cat cac gct tag g) and cloned as an EcoRI-NsiI fragment in pIC1144 digested with MfeI and PstI, resulting in plasmid pIC1156. The BGMV insert in pIC1156 was sequenced. Two other BGMV DNAA genome fragments were amplified from BGMV infected *Phaseolus vulgaris* DNA with primers pairs dnaapr9 (aag ctg cag aag gat cct ctg gac tta cac gtg gaa tgg)/dnaapr13 (cgc tcg agg ccg tcg act tgg aat tgt c), and dnaapr5 (gaa gat ctg caa gag gag gtc agc a)/dnaapr10 (aag ctg cag atc tat ttc tat gat tcg ata acc). The sum of these fragments amounts to a complete BGMV genome without the coat protein. These fragments were digested with Xho1/Pst1 and Pst1/BglII (respectively) and cloned in a three way-ligation in pIC1156 digested with XhoI and BglII. The resulting plasmid contains one complete BGMV DNAA genome without the coat protein gene flanked by duplicated BGMV DNAA common regions. Three clones were kept for testing: pIC1663, 1664 and 1667. A multicloning site containing BamHI and PstI replaces the coat protein gene.

A GFP (SGFP stands for synthetic GFP) coding sequence was cloned as a BamHI-PstI fragment from pIC011 (Hbt promoter-Synthetic GFP coding sequence-Nos terminator in pUC18), into the BamHI-Pst1 sites of pIC1663 pIC1664 and pIC1667, resulting in plasmids pIC1693, pIC1694 and pIC1697 (Appendix 1). GFP is placed under the control of the coat protein promoter.

A DNAA genome clone mutated for the replicase was made by destroying a BglII site present in the AL1 ORF. As two BglII sites are present in pIC1693, pIC1694 or pIC1697, an intermediate construct lacking the second BglII site was made (pIC2690). This construct was made by amplifying a fragment from pIC1694 by PCR using primers dnaapr16 (aag ctg cag gtc tat ttc tat gat tcg ata acc) and dnaapr5 (gaa gat ctg caa gag gag gtc agc a), and cloning a Pst1-HindIII fragment from the amplified product into pIC1694 digested with Hind3 and PstI. pIC2690 was then digested with BgI2, the ends filled-in with klenow polymerase and religated to give plasmid pIC2705 (Appendix 3).
Cloning of the DNAB Genome A complete DNAB genome was amplified by PCR from BGMV-infected *Phaseolus vulgaris* DNA with primers dnabpr2 (cgg cat gca tgc att tgg agg att tgc taa ctg) and dnabpr3 (cgg atg cat tca att atg tag agt cac aca g). The amplified fragment was cloned in the pGEMT vector from promega. Digestion of the clones with NsiI releases a complete linear DNAB genome. Twelve colonies were picked and nine clones containing an insert, pIC1911 to pIC1919 (Appendix 2), were kept for testing for functionality.
Test for Functionality of DNAA and DNAB Clones:

To test for functionality of GFP (functional coat protein promoter and functional coding sequence), pIC1693, pIC1694 and pIC1697 were bombarded in *Nicotiana benthamiana* and *Phaseolus vulgaris* excised leaves using a Biolistic Particle Delivery System 1000/HE (Biorad). GFP-expressing epidermal cells could be detected the next day in leaves of both species for all three constructs.

To test for replication and movement of DNAA and DNAB clones, pIC1693, 1694 and 1697 were cobombarded with pIC1911 to 1919 (digested with NsiI) in pairwise combinations, in *Phaseolus vulgaris* excised leaves. All combinations gave rise to hundreds of GFP expressing cells. For two plasmid combinations, 1694/1914 and 1697/1919, expression of GFP spread to neighbouring cells for a few of the GFP expressing cells, mainly in veins.

To test for the functionality of the DNAA and DNAB clones in entire plants, combinations of pIC1694/1914 and pIC1697/1919 were bombarded in the radicle of germinating bean plants (FIG. 2). The seedlings were transferred to soil and scored for GFP expression in the first two leaves 10 days later. The majority of the seedlings showed fluorescence in some of the veins of the first two leaves. DNA was extracted from the first two leaves and analyzed by Southern blotting with a DNAA probe. Single stranded, supercoiled double stranded and open circle double stranded forms were detected when plants were inoculated with the DNAA and DNAB clones but not when the plants were inoculated with DNAA clones only. The GFP protein was also detected by Western blotting using a GFP antibody.

Example 2

This example shows that replication of a plasmid can increase the frequency of recombination with a target co-transformed non-replicating plasmid. In this example, recombination is mediated by Cre recombinase and takes place at the loxP and LoxM sites present on both the donor and recipient plasmid (FIG. 3).
Description of the Plasmids:

A PCR fragment was amplified from pIC1667 with dnaapr13 (cgc tcg agg ccg tcg act tgg aat tgt c) and dnaapr15 (ccc atg cat cta gag tta acg gcc ggc cca aat atc taa cgt tct cac atg) and cloned as an XhoI-NsiI fragment in pIC1667 digested with XhoI and PstI. The resulting plasmid, pIC1951, is similar to pIC1667 but lacks the coat protein gene promoter.

Plasmid pIC551 was obtained by (i) performing PCR on pUC119 digested with XbaI and Hind3 with primers adlox1 (gtt cta gat gtt aac ggc gcg ccg gcg taa tca tgg tca), adlox2 (aac cat gga gaa ttc ggc cgg ccc tgg ccg tcg ttt tac aac), adlox3 (cgg gat cct gag ctc tat aac ttc gta taa tgt atg cta tac gaa gtt gtt cta gat gtt aac gg) and adlox4 (cgg gat ccc tgc aga taa ctt cgt ata atc tat act ata cga agt tag aaa aac aac cat gga gaa ttc gg), (ii) digesting the PCR product with BamHI and (iii) religating the digested fragment. pIC551 is similar to pUC119 but has the polylinker AscI-HpaI-XbaI-loxA-SacI-BamHI-PstI-LoxM-NcoI-EcoRI-FseI.LoxA (acaacttcgtatagcatacattatacgaagttat) and LoxM (ataacttcgtataatctat actatacgaagttag) are modified LoxP sites. LoxA differs from LoxP at one nucleotide in one of the inverted repeats and can recombine at wild-type level with LoxP. LoxM has two mutations in the central spacer region and cannot recombine with either LoxP or LoxA, but can freely recombine with itself as is the case for other heterospecific sites (Bethke & Sauer, 1997, *Nucl. Acids Res.*, 25, 2828-2834).

A BamHI-Pst1 fragment from pIC011 containing the GFP coding sequence was cloned in the BamHI and Pst1 sites of pIC551, resulting in plasmid pIC2051 (Appendix 4). A FseI/Xba1 fragment containing the GFP ORF flanked by LoxA and LoxM sites in opposite orientation was subcloned from pIC2051 into the XbaI and FseI sites of pIC1951, resulting in plasmid pIC2121 (Appendix 5). pIC2121 contains a promoterless GFP coding sequence located between two heterospecific sites, replacing the coat protein gene.

pIC1262 was made by cloning a 0.9 kb Ecl136II-Pst1 *Arabidopsis* actin2 promoter fragment from pIC04 (actin2 promoter fragment cloned in a plasmid vector) into the Hind3-blunt and Pst1 sites of pIC08 (35S promoter-LoxP-Cre-Nos terminator in pUC19). pIC1321 was made by replacing the Nos terminator of pIC1262 by a DNA fragment containing a LoxM (in opposite orientation relatively to the LoxP site) site followed by the Ocs terminator. pIC1321 (Appendix 6) contains the following insert in pUC19: *Arabidopsis* actin2 promoter-LoxP-Cre Orf-LoxM-Ocs terminator.

Recombination of a Replicating Plasmid with a Non-Replicating Plasmid Target Site (FIG. 3)

pIC2121 was co-bombarded with pIC1321 in wild-type *N. benthamiana* leaf, *Phaseolus vulgaris* leaf, and *Phaseolus vulgaris* bean cell suspension culture. As a control, pIC2051 was co-bombarded with pIC1321 in the same plant tissues. After three days, replication of the pIC2121 insert leads to increased recombination with pIC1321 and results in exchange of the Cre ORF with the GFP coding sequence. Fusion of GFP to the *arabidopsis* actin2 promoter leads to expression of GFP. No GPF expressing cells were detected in the control experiment with non-replicating plasmid pIC2051 (FIG. 3).

Example 3

In this example, we show that replication of a plasmid containing an insert to be targeted can increase the frequency of recombination with a target site stably inserted on a plant chromosome. Recombination is mediated by Cre recombinase and takes place at the loxP and LoxM sites present on both the replicating plasmid and the target site, and Cre is delivered on a co-transformed plasmid (FIG. 4).

Description of Plasmids:

An adaptor (made with primers adlox15 [tcg aga taa ctt cgt ata gca tac att ata cga agt tat agc t] and adlox16 [ata act tcg tat aat gta tgc tat acg aag tta tc]) containing a LoxP site flanked with XhoI and SacI was cloned in pIC01 digested with XhoI and SacI. The resulting plasmid, pIC2745 contains the DNA fragment (35S promoter-LoxP-Gus-Ocs terminator) in pUC118. An adaptor (made with primers adlox17 [gat cat aac ttc gta taa tct ata cta tac gaa gtt att] and adlox18 [cta gaa taa ctt cgt ata gta tag att ata cga agt tat]) containing a LoxM site (in opposite orientation) flanked with BamHI and XbaI sites was cloned in pIC2745 digested with BamHI and XbaI, resulting in plasmid pIC2755. An EcoRI-Hind3 fragment was subcloned from pIC2755 into the EcoRI and Hind3 sites of the binary vector pICBV1 (vector developed at Icon Genetics; any other binary vector system would be equally suitable for this cloning). The resulting plasmid, pIC2764 (Appendix 7) contains the insert (35S promoter-LoxP-Gus-LoxM-Ocs terminator) in a binary vector.

The Cre ORF was amplified by PCR from pIC08 with primers crerecomb1 (CATGCCATGG CCAATTTACT GACCT) and crerecomb2 (TGCTCTAGAC TAATCGCCAT CTTCCAGC) and cloned as a NcoI-XbaI blunt fragment into the PstI blunt and NcoI sites of pIC011. The resulting clone, pIC2721 (Appendix 8), contains the Cre ORF under the control of the Hbt promoter (chimeric promoter containing the 35S enhancer fused to the basal promoter of the maize C4PPDK gene; see Sheen, *EMBO J.*, 1995, 12, 3497) in pUC18.

Increased Recombination of a Replicating Plasmid with a Chromosomal Target Site.

Construct pIC2764 was introduced in *Agrobacterium* strain GV3101 by electroporation, and the transformed bacteria used for *Nicotiana benthamiana* transformation. Thirty transgenic *N. benthamiana* plants were stained with an X-gluc solution (Jefferson, 1987, *Plant Mol. Biol. Reporter*, 5, 387-405) to select plants with high levels of Gus expression. Plants expressing Gus were bombarded with a mix of plasmids pIC2721 and pIC2121. After delivery to plant cells, a DNAA genome containing GFP is expected to be released from pIC2121 and to replicate. Cre-mediated recombination results in exchange of the Gus coding sequence at the target locus on the chromosome by the GFP coding sequence, placing GFP under control of the 35S promoter. In a control experiment, pIC2051 (non-replicating promoterless GFP construct) was cobombarded on transgenic *N. benthamiana* plants expressing Gus. More GFP expressing cells were detected when pIC2121 was cobombarded with pIC2721 than in the control experiment.

pIC2764 was also transformed in a *Phaseolus vulgaris* cell suspension culture line developed at Icon Genetics. Stably transformed colonies were stained with X-Gluc to select lines with a high level of Gus activity. Cells from two clones expressing Gus at high level were multiplied and bombarded with a mix of plasmids pIC2121 and pIC2721 or with a mix of plasmids pIC2051 and pIC2721. More GFP positive cells were observed a week after bombardment when pIC2121 was cobombarded with pIC2721 in comparison with the control experiment.

Example 4

In this example we show that site-targeted recombination events as described in example 3 can lead to the production of stably transformed bean cells. In this example, the BAR gene (FIG. 5) is replaced by GFP, but the targeting strategy is identical as in example 3.

Plasmid Description and Experiment

PIC2103 was made by cloning a SstI-BamHI fragment from pIC012 (Nos promoter-Bar coding sequence-Ocs terminator in pUC118) in the SstI-BamHI sites of pIC551. A pIC2103 FseI-XbaI fragment containing the BAR coding sequence flanked by two heterospecific Lox sites in opposite orientations was subcloned in the FseI-XbaI sites of pIC1951 resulting in plasmid pIC2574 (Appendix 9). pIC2574 contains a promoterless BAR coding sequence cloned between two heterospecific sites, replacing the coat protein gene.

pIC2574 was digested with BgI2 and religated. The resulting clone pIC2948 (Appendix 10) has a deletion of the Al1 (replicase), Al2 and Al3 ORFs.

Cells from two *P. vulgaris* transgenic lines (stably transformed with pIC2764) described above were bombarded with a mix of plasmids pIC2574 and pIC2721 or with a mix of plasmids pIC2948 and pIC2721. Transformed clones were selected on plates containing phosphinotricin (PPT). Transformed clones were analyzed by PCR to make sure that they had been produced by site-specific recombination. More PPT resistant clones were obtained when pIC2574 was used than when the non-replicating control pIC2948 was used.

Example 5

In this example, the strategy is similar to that of example 4. However, here, the replicase is present on a non-replicating plasmid with Cre (FIG. 6). The benefit of this approach is that replication of the replicon is only transient and stops when the non-replicating plasmid carrying the replicase disappears. The advantage is that transformed cells are free of replicating plasmid, are healthier and transgenic plants can be regenerated more easily.

Plasmid Description and Experiment:

A fragment containing the Al1 (replicase), Al2 and Al3 ORFs was amplified from plasmid pIC1664 using primers Al1xho1 (tct ctc gag tta caa ata tgc cac cac ctc aaa g) and Al1xba1 (gct cta gag gat cta ttt cta tga ttc gat aac c). The amplified fragment was cloned as a Xho1 Xba1 fragment in the Xho1 and Xba1 sites of pIC01 (35S promter-Gus coding sequence-Ocs terminator in pUC118). The resulting plasmid, pIC2821, contains the BGMV replicase under the control of the 35S promoter.

An adaptor (ecopst1, ecopst2) was cloned in the EcoRI site of pIC2721. The resulting clone, pIC2955, has the EcoRI site replaced by the Mfe1 and Pst1 sites. Two fragments from pIC2821 (a EcoRI-NcoI fragment and a NcoI-Pst1 fragment) were cloned in a three-way ligation in pIC2955 digested with Mfe1 and Pst1. The resulting plasmid, pIC2966 (Appendix 11), contains the BGMV replicase expressed from the 35S promoter and the Cre coding sequence under the control of the Hbt promoter.

Cells from two *P. vulgaris* transgenic lines (stably transformed with pIC2764) described above were bombarded with a mix of plasmids pIC2948 and pIC2966 or with a mix of plasmids pIC2948 and pIC2721. Transformed clones were selected on plates containing phosphinotricin (PPT). Transformed clones were analyzed by PCR to check that they had been produced by site-specific recombination. More PPT resistant clones were obtained when pIC2948 was replicating (due to the replicase on pIC2966) than in the non-replicating control when pIC2948 is cotransformed with pIC2721.

Example 6

In this example, a replicating clone carrying GFP is co-bombarded with a replicating Cre-expressing clone and the BGMV DNAB genome (FIG. 7). All three clones are able to replicate, and because of the presence of the B genome, all three clones are able to move to neighboring cells where they also replicate. The result is an increase in the number of cells where site-specific recombination events take place.

Plasmid Description and Experiment

The Cre ORF was excised from pIC903 (Cre ORF cloned in pGem-T from Promega) as a SacI blunt-Pst1 fragment and cloned in the BamHI blunt and Pst1 sites of pIC1664. The resulting plasmid pIC2736 (Appendix 12) contains the Cre coding sequence under the control of the BGMV coat protein promoter in a DNAA replicating vector.

pIC2121 was co-bombarded with pIC2736 and pIC1914 (Nsi1-digested) in leaves of transgenic *Nicotiana benthamiana* plants transformed with pIC2764. In a control experiment, pIC2051 was co-bombarded with pIC2721. A week after bombardment, more GFP-expressing cells were detected in the experiment than in the control.

Example 7

This experiment is similar to the one described in example 6, but differs by the inability of the B genome clone to replicate and to move to neighboring cells (FIG. 8). The B genome clone is only transiently expressed and disappears after some time. It is advantageous to eliminate the B clone as it has been shown that expression of the BL1gene is in large part responsible for the disease symptoms of geminivirus-infected plants (Pascal et al., 1993, *Plant Cell*, 795-807). It has also been shown that transient expression of genes of the B genome is sufficient for systemic movement of DNAA genome for TGMV (Jeffrey et al., 1996, *Virology*, 223, 208-218).

Plasmid Description and Experiment

An EcoRI-SacI fragment from pIC04 containing the *Arabidopsis* actin2 promoter was cloned in the EcoRI and SacI sites of pIC02 (35S promoter-Gus coding sequence-Ocs terminator in pUC118), resulting in plasmid pIC2779. A PCR fragment containing the BGMV BL1 Orf was amplified from *Phaseolus vulgaris* DNA (extracted from BGMV infected leaf tissue) using primers Bl1Xho1 (gcc tcg agc tta aat gga ttc tca gtt agc) and Bl1bam (cgg gat cct tat ttc aaa gac ttt ggt tga g). This fragment was cloned as an Xho1-BamHI fragment in pIC01, resulting in plasmid 2781. A PCR fragment containing the BGMV BR1 ORF was amplified from pIC1914 DNA using primers Br1nsi1 (cga tgc atc aca cga att aat aat gta tgc gtc) and Br1bam (cgg gat cct tat cca aca taa tca aga tca aat g). This fragment was cloned as a Nsi1-BamHI fragment in pIC2779, resulting in plasmid 2792. Two pIC2781 fragments (EcoRI blunt-BamHI and BamHI-Hind3) were cloned in a three ways ligation in pIC2792 digested with Pst1 (blunted) and Hind3. The resulting plasmid, pIC2807 (Appendix 13), contains the BR1 and BL1 ORFs under control of the *Arabidopsis* actin2 promoter and the 35S promoter (respectively), in pUC118.

pIC2121 was co-bombarded with pIC2807 and pIC2736 in leaves of transgenic *Nicotiana benthamiana* plants transformed with pIC2764. In a control experiment, pIC2051 was co-bombarded with pIC2721. A week after bombardment, more GFP-expressing cells were detected in the experiment than in the control.

Example 8

This example is similar to example 6, but here the recombinase is expressed from the target site instead of being delivered from a replicating clone (FIG. 9). The advantage is that Cre is already expressed in all the cells where replicating clones move. In addition, recombination at the target site displaces cre, preventing its further expression.

Plasmid Description and Experiment

The actin2 promoter-LoxP-Cre Orf-Nos terminator fragment from pIC1321 was subcloned as a Not1 blunt-SacI fragment into the SmaI and SacI sites of the binary vector pBIN19, resulting in construct pIC1593 (Appendix 14).

A LoxP-Gus-Ocs terminator-LoxP fragment was amplified from plasmid pIC02 using primers LoxPgus (ggc atc gat ata act tcg tat agc ata cat tat acg aag tta tac aat ggg tca gtc cct tat g) and LoxPocs (gcc cat gga taa ctt gct ata atg tat gct ata cga agt tat gtc aag gtt tga cct gca c). The amplified fragment was digested with ClaI and NcoI and cloned in pIC591 (pIC011 with BamHI site replaced by ClaI) digested with ClaI and NcoI. The resulting plasmid, pIC2553, contains the Gus gene flanked by LoxP sites inserted between the promoter and the coding sequence of GFP.

pIC1593 was introduced in *Agrobacterium* strain Agl1 by electroporation and transformed *agrobacteria* used to transformed *Nicotiana benthamiana*. DNA extracted from 10 transformants was used to test for the presence of the transgene by PCR. All plants were found positive when PCR was performed with primers for the kanamycin transformation marker or for the Cre gene. To test functionality of the Cre recombinase in transgenic plants, one leaf of 25 transformants was bombarded with plasmid pIC2553. In presence of cre, recombination of the LoxP sites of pIC2553 results in expression of the GFP gene. Leaves of plants that were found to express Cre were bombarded with a mix of plasmids pIC2121 and pIC1914 (NsiI-digested). In a control experiment, leaves of the same transgenic plants were bombarded with a mix of plasmids pIC2051 and pIC1914 (Nsi1-digested). More GFP-expressing cells were observed in the experiment than in the control.

Example 9

This example shows that replication of a plasmid containing a DNA sequence homologous to a target sequence in the genome can lead to homologous recombination with this target sequence (FIG. 10).

Plasmid Description and Experiment

A fragment of the *Phaseolus vulgaris* ALS gene was amplified from genomic DNA using degenerate primers alsdpr1 (cgg gat ccc agg tgg ngc wtc mat gga gat) and alsdpr2 (cgg agc tcg cat aca cag thc crt gca t) and was sequenced directly. Sequence information was used to design two primers (alspr3: cga cag cgt cgc cct cgt tgc cat c and alspr4: gat ggc aac gag ggc gac gct gtc g) that overlap with a proline (equivalent to Pro-165 of maize AHAS108 [Lee et al., 1988, *EMBO J.*, 7, 1241-1248]). Alspr3 and alspr4 contain a nucleotide substitution to change this proline to alanine. Using PCR, a AHAS DNA fragment with a proline mutated to alanine was amplified from bean genomic DNA using primers alsdpr1, alsdpr2, alspr3 and alspr4. This DNA was cloned in pIC2171 as a SacI-BamHI fragment, resulting in plasmid pIC2834 (Appendix 15).

As a control for a non-replicating plasmid, the SacI-BamHI fragment from pIC2834 was subcloned in pUC19, resulting in plasmid 2857 (Appendix 16).

Bean cell suspension cultures were prepared from *Phaseolus vulgaris* leaf tissue. Sixty plates, each containing approximately $10^6$ cells, were bombarded with plasmid pIC2834. As a negative control, sixty plates were bombarded with plasmid pIC2857, and 40 additional plates were not bombarded but grown in the same conditions. The transformed cells were plated on solid culture medium containing 20 ppb chlorosulfon (Glean, technical grade, Dupont). Putative events identified 4 to 6 weeks after bombardment were selected on fresh media containing 50 ppb chlorosulfon. The resistant clones were analyzed by PCR amplification and sequencing. More resistant clones resulting from the expected change (Proline to Alanine at the targeted codon) were obtained in the experiment (using the replicating clone pIC2834) than in the controls.

Example 10

This example shows that replicating geminiviral clones can be delivered by agroinfiltration.

Plasmid Description and Experiment

A binary vector containing the proreplicon part of pIC1694 was made by subcloning a XhoI-NarI fragment from pIC1694 into pICBV11 digested with Xho1 and Cla1. The resulting clone, pICH4300 (FIG. 11), contains the GFP gene under control of the BGMV coat protein promoter and the Al1/2/3 genes, between duplicated CRs. pIC4300 was transformed in *Agrobacterium* strain GV3101. *Agrobacterium* cells were grown overnight in LB containing 100 uM acetosyringone. The following day, bacteria were pelleted and resuspended at an OD of 0.8 in a solution containing 10 mM MES, 10 mM MgSO4 and 100 uM acetosyringone. Resuspended *agrobacterium* cells were infiltrated in *Nicotiana benthamiana* leaves. From two days post inoculation to more than 2 weeks, strong GFP fluorescence was observed in the infiltrated area. To check that geminiviral replicons were formed, genomic DNA was extracted from infiltrated areas 3 days post inoculation, and analyzed by Southern blot. Undigested DNA analyzed with a GFP probe revealed the presence of nicked open circular DNA and supercoiled DNA, while DNA linearized with BamHI gave a single migrating fragment. By comparison of the intensity of the signal of linearized DNA with the signal of plasmid DNA of known concentration, it was estimated that replicons are present at 15 to 30000 copies per cell.

Example 11

In this example, we show that geminiviral clones lacking replicase can replicate efficiently when the replicase is provided in trans.

Plasmid Description

A PCR product amplified from pICH4300 with crpr6 (cgc aat tgc tcg agc ttt gag gtg gtg gca tat ttg) and gfppr1 (cgct-gaacttgtggccgttcac) was cloned as a Xho1 BamHI fragment in the Xho1 BamHI sites of pICH4300. The resulting clone pICH5184 is similar to pICH4300 but lacks a fragment of the AL1 gene located outside the proreplicon area in pICH5184. A GFP proreplicon lacking the replicase was made by cloning a PCR product amplified from pICH4300 with crpr9 (cgg tca tga ttc tca agc aca gta tgg cat att tgt aaa tat gcg agt gtc) and crpr8 (gc tct aga gac acg tgg agg cgt acg g) in the BspH1 and Xba1 sites of pICH5184. Plasmid pICH5170 (FIG. 11) was made by cloning an Xho1 Xba1 fragment (Al1/2/3 Orfs) of pICH2821 in pICBV16 (Icon Genetics Binary vector, Kan selection). Al1/2/3 Orfs are under control of the 35S promoter in pICH5170. A PCR product amplified from pICH4300 with primers crpr8 (gc tct aga gac acg tgg agg cgt acg g) and crpr9 (cgg tca tga ttc tca agc aca gta tgg cat att tgt aaa tat gcg agt gtc) was cloned as a BspHI Xba1 fragment in pICH4300. The resulting plasmid, pICH5203 (FIG. 11), is similar to pICH4300 but lack the Al1/2/3 Orfs. PICH4699 is similar to pICH4300 but the GFP coding sequence was replaced by a DNA sequence containing LoxA-Gus coding sequence-nos terminator-LoxM in antisense orientation.

Experiment pICH5203, pICH4699 and pICH5170 were transformed in *Agrobacterium* strain GV3101. *Nicotiana benthamiana* leaves were infiltrated as described above. pICH5203 was infiltrated alone, with pICH4699 or with pICH5170, and pICH4300 was infiltrated as a positive control. Genomic DNA was extracted from infiltrated areas 4 days later and was analyzed by Southern blotting with a common region probe. No replication was detected when pICH5203 was infiltrated alone (Lane 1-3, FIG. 11). The pICH5203 replicon amplified at high level (FIG. 11, lane 4-6, fragment b) in tissues coinfiltrated with pICH4699 (which replicates constitutively; amplified fragment (a) is shown on FIG. 11). It also replicated efficiently when it was coinfiltrated with pICH5170 which does not replicate (FIG. 11, lane 7-9), but at a lower level (approximately 5 times lower) than when pICH4300 was infiltrated alone (lane 10-12).

Example 12

In this example, recombination relies on the *Streptomyces* Phage PhiC31 integrase system and recombination takes place between AttP and AttB sites. Site targeted transformation is performed using *agrobacterium* transformation but could also be performed by other means of delivery.

Plasmid Description pICH6272 (FIG. 12) consists of: the 34S promoter-AttB site-Gus coding sequence-Ocs terminator-AttB site (in inverse orientation)-GFP coding sequence-Nos terminator, cloned in pICBV10 (Icon Genetics Binary vector with Nos promoter-NptII coding sequence-Nos terminator for selection). The 34S promoter was cloned from pICP1159 (Chloramphenicol plasmid containing the 34S promoter-multicloning site-Mannopine synthase terminator) as a Xba Bgl2 fragment. The Gus coding sequence-Ocs terminator sequence block comes as a Sac1 Pst1 fragment from pIC01. The GFP coding sequence-nos terminator comes from a pIC011-derived clone missing the Pst1 site. The AttB recombination site (ccgcggtgcgggtgccag ggcgtgcccttgggctc-cccgggcgcgtactccac) was synthesized from oligonucleotides ordered from InVitrogen.

pICH7555 (FIG. 12) consists of: the *arabidopsis* actin 2 promoter-PhiC31 integrase-Nos terminator-BGMV common region-AttP site-Bar coding sequence-Ocs terminator-35S promoter-AttP site in inverse orientation-BGMV common region, cloned in pICBV10. The common region comes from pIC1694, the Bar-Ocs terminator from pIC012, the 35S promoter from pIC01 and the Actin 2-PhiC31 integrase-Nos terminator block from pICP1010. The AttP recombination site (gtagtgccccaactggggtaacctttgagttctctcagttgggggcgta) was synthesized from oligonucleotides ordered from InVitrogen.

Experiment

Plasmid pICH6272 was stably transformed in *Nicotiana tabacum* by *Agrobacterium* transformation. Transgenic plants were checked for Gus expression by staining leaf tissue with X-Gluc. Two transformants expressing Gus were chosen to be used for site-targeted transformation. Recombination at the AttP sites on the replicons (derived from pICH7555) with the AttB sites at the target site (derived from pICH6272) should place the promoterless BAR gene (from the replicon) under control of the 34S promoter, thereby conferring PPT resistance to transformed cells. Leaf discs of both transformants were inoculated with *Agrobacteria* carrying plasmid pICH7555 or by a mixture of *Agrobacterium* cultures containing pICH7555 and pICH5170. In the presence of PhiC31 integrase, site-specific recombination of the two AttP sites on the replicon can take place at either one of the two AttB sites at the target locus. When the first AttP site of construct pICH7555 or of the pICH7555-derived replicon recombines with the first AttB site at the target locus, the promotorless Bar gene from pICH7555 or from the replicon is placed under control of the 34S promoter at the target site. Selection for transformants was made on PPT-containing media. More transformants were obtained when the gene to be targeted replicated transiently (transient expression of both pICH7555 and pICH5170) than when it did not replicate (pICH7555 alone). Transformants were analyzed by PCR and Southern blotting to confirm that they were site-targeted transformants.

Example 13

In this example, the target site and the gene to be targeted (present on a proreplicon) are first transformed in separate plants. Delivery of the gene to be targeted is achieved by hybridization.

Plasmid Description:

pICH6313 (FIG. 12) is derived from plasmid pICH6272. A Bgl2 SpeI fragment was subcloned from pICH6303 (Al1/2/3 Orfs linked to an Internal Ribosome Entry Site in binary vector) into the Xba1 BamHI sites of pICH6272. The resulting plasmid contains the Gus and Al1/2/3 genes under control of the 34S promoter.

pICH6040 (FIG. 12) consists of: the 35S promoter-AttB site-Bar coding sequence-Ocs terminator AttP site-GFP coding sequence-Nos terminator in pUC118. The 35S promoter sequence comes from pIC01, the Bar-Ocs terminator from pIC012 and the GFP-Nos terminator from pIC011. pICH6040 was designed as a test construct to check PhiC31 expression in transgenic plants: upon expression of PhiC31 integrase, intramolecular recombination of AttB with AttP leads to fusion of the GFP coding sequence to the 35S promoter, and to GFP expression.

Experiment pICH7555, pICH6313 and pICH6272 were stably transformed into *Nicotiana tabacum* using *agrobacterium* transformation. pICH6313 transformants that expressed Gus were selected to be used in crosses with pICH7555 transformants. These transformants are also expected to express the BGMV replicase as it is linked to Gus by an IRES. pICH7555 transformants were checked for the presence of the proreplicon by PCR, and for activity of the PhiC31 integrase by bombardment of leaf tissue with test construct pICH6040. pICH6313 transformants were crossed as female with pICH7555 transformants. In F1 plants, expression of the Al1/2/3 genes from pICH6313 results in formation of replicons from the pICH7555 transgene. Recombination of replicon molecules with the target site results in fusion of the BAR gene to the 34S promoter. At the same time, replacement of the Gus coding sequence-IRES-Al1/2/3 Orfs by the Bar coding sequence-Ocs terminator-35S promoter results in termination of replication of the replicon. In control crosses (no replication) pICH6272 transformants were crossed as female to pICH7555 transformants. F1 plants from both types of crosses were grown without selection, and Basta selection was applied on F2 seedlings. More Basta resistant plants were obtained from crosses with pICH6313 than in crosses with pICH6272. Basta resistant plants were checked by PCR and Southern blot analysis to confirm that they resulted from site-targeted recombination events.

Example 14

In this example we use an RNA virus provector system as an assay to detect successful site-targeted DNA recombination events. Recombination events at LoxP sites on separate fragments of a provector system lead to DNA molecules that are transcribed into functional viral transcripts capable of amplification. Using this assay, we show that replication of a DNA sequence increases the rate of site-specific recombination with a non-replicating target sequence.

Plasmid Description pICH4371 consists of a 5' provector based on the TVCV RNA virus. pICH4371 contains the *arabidopsis* actin 2 promoter—the TVCV polymerase—a truncated version of the movement protein—a LoxP site-Nos terminator, in binary vector. pICH4461 consists of the 3' end provector. It contains a LoxP site-GFP coding sequence-viral 3' NTR-Nos terminator, in binary vector. pICH7311 was made by cloning a EcoRI-PstI fragment from pICH4461 (containing the 3' provector fragment) into pICH6970 (LoxA-Bar coding sequence-LoxM between 2 BGMV common regions in Binary vector) digested with EcoRI-PstI. pICH7311 consists of LoxP-GFP coding sequence-TVCV 3' NTR-Nos terminator between two BGMV common regions in binary vector (FIG. 13). pICH1754 consists of: *Arabidopsis* actin 2 promoter-LoxP-cre coding sequence-LoxM-Ocs terminator cloned in pICBV10. pIC1754 is used here to provide cre recombinase.

Experiment:

pICH4371, pICH7311, pICH5170 and pICH1754 were transformed into *Agrobacterium* strain GV3101. pICH4371 was coinfiltrated in *N. benthamiana* leaves with pICH7311, pICH1754, with or without pICH5170 (BGMV replicase). Infiltration with pICH5170 resulted in more GFP sectors than without pICH5170 (FIG. 13) showing that amplification of 3'-end provector results in an increase of site-specific recombination events. As a negative control, pICH7311 was infiltrated with or without pICH5170. No GFP expression could be detected in either case indicating that GFP is not expressed from the 3' provector clone alone. Also, pICH4371 was coinfiltrated with pICH4461 and pICH1754. The same number of recombination events was observed as when pICH4371 was coinfiltrated with pICH7311 and pICH1754 (not shown).

Example 15

In this example we show that replication of a DNA sequence increases the rate of homologous recombination with a non-replicating homologous sequence. Recombination events are detected by mutating a non-functional RNA proreplicon to a functional one, leading to amplification and to GFP-expressing leaf cell sectors.

Plasmid Description

Plasmid pICH7477 (FIG. 14) was made by ligating three fragments from pICH4351; a KpnI SphI-blunt fragment, a SphI-blunt Xho1 fragment and a Xho1 Kpn1 fragment. The resulting clone, pICH7477, contains a frameshift in the TVCV RNA dependent RNA polymerase (Rdrp) Orf at the Sph1 site, and is therefore a non-functional proreplicon clone. A non-mutant fragment from the TVCV Rdrp Orf was PCR-amplified from pICH4351 with primers rdrppr3 (ttt ccatgg att acc ctg tta tcc cta aag gca tct cgt cgc gtt tac) and rdrppr4 (ttt ctgcag gaa atg aaa ggc cgc gaa aca ag) and cloned as a Nco1 Pst1 fragment in pICH7423 (pICH7423 is a derivative of pICH1694 in which a Hind3 Nco1 from the coat protein promoter region was removed). The resulting clone, pICH7480 (FIG. 14), contains a non-mutated fragment of TVCV flanked on one side by a I-SceI restriction site, in a geminiviral proreplicon. The Nco1 Pst1 fragment from pICH7480 was subcloned in Nco1 and Pst1 sites of pICH6970. The resulting clone, pICH7499 (FIG. 13), is similar to pICH7480 but cannot replicate autonomously due to the lack of replicase. It can however replicate when the replicase is provided in trans.

Experiment:

Plasmid pICH4351 is a proreplicon carrying GFP that is based on the RNA virus TVCV. In pICH7477, replicons cannot be produced due to a frameshift in the ORF of TVCV. *Nicotiana benthamiana* plants were infiltrated with *agrobacterium* containing plasmid pICH7480. As a nonreplicating control, pICH7499 was agroinfiltrated in a second plant. One day later, both plants were infiltrated with pICH7477 and pICH7500 (35S promoter-I-SceI endonuclease-Nos terminator). Expression of pICH7500 leads to I-SceI restriction endonuclease and cleavage of geminiviral replicons at the I-SceI restriction site. Homologous recombination of the linearized fragments with the mutated part of the TVCV Orf leads to restoration of functional TVCV proreplicons. More GFP expressing sectors were formed with pICH7480 than with pICH7499.

In an variation of this experiment, the replicase for the geminiviral replicons is expressed in trans transiently. *Nicotiana benthamiana* plants were infiltrated with pICH7480 alone or with pICH7480 and pICH5170. One day later, all plants were infiltrated with pICH7477 and pICH7500. More GFP sectors were obtained in plants inoculated with pICH5170 than in plants inoculated with pICH7480 alone.

In another experiment, pICH7477 was stably transformed in *N. benthamiana*. Transformants were infiltrated with pICH7480 or pICH7499. One day later, I-SceI restriction endonuclease was delivered by infiltrating the same areas with pICH7500. More GFP sectors were obtained in plants infiltrated with pICH7480 than in plants infiltrated with pICH7499.

In another experiment, transgenic plants for pICH7477 were infiltrated with pICH7499 alone or with pICH5170. One day later Restriction endonuclease was delivered by infiltrating the same areas with pICH7500. More GFP sectors were obtained in plants infiltrated with pICH5170 than in plants infiltrated with pICH7499 alone.

The invention claimed is:

1. A process of causing a targeted integration of DNA of interest into a plant cell nuclear genome, comprising:
   (i) providing plant cells with an amplification vector, or a precursor thereof, capable of replication in plant cells, said vector comprising:
      (a) DNA sequence(s) encoding a geminiviral origin of replication and functional in plant cells,
      (b) DNA sequence(s) necessary for site-specific and/or homologous recombination between the vector and a host nuclear DNA, and
      (c) optionally, further DNA of interest;
   (ii) providing said plant cells with a replicase gene of the replicase involved in replicating the amplification vector on a non-replicating vector, whereby the replication of said amplification vector in said plant cells is transient;
   (iii) optionally providing conditions that facilitate vector amplification and/or cell to cell movement and/or site-specific and/or homologous recombination; and
   (iv) selecting cells having undergone recombination at a predetermined site in the plant nuclear DNA.

2. A process of causing a targeted integration of DNA of interest into a plant cell nuclear genome, comprising the following steps:
   (i) transfecting or transforming a plant cell with a first DNA comprising a sequence which, when integrated in the plant cell genome, provides a target site for site-specific and/or homologous recombination;
   (ii) selecting a cell which contains said target site for site-specific and/or homologous recombination in its nuclear genome;
   (iii) transfecting or transforming said selected cell with a second DNA comprising a region for recombination with said target site and a first sequence of interest;
   (iv) optionally providing enzymes for recombination; and
   (v) selecting cells which contain the sequence of interest from the second DNA integrated at the target site,
   whereby at least one of said first or said second DNA is delivered by an amplification vector, or a precursor thereof, capable of replication in a plant cell and comprising (a) DNA sequence(s) encoding a geminiviral origin of replication functional in the plant cell, and wherein the replicase gene of the replicase involved in replicating the amplification vector is provided to said plant cell on a non-replicating vector whereby the replication of said amplification vector in said plant cell is transient.

3. The process according to claim 1 or 2, wherein said amplification vector comprises DNA sequence(s) necessary for homologous recombination.

4. The process according to claim 1 or 2, wherein said providing a plant cell with an amplification vector, or a precursor thereof, or said transfecting or transforming is done by *Agrobacterium*-mediated delivery.

5. The process according to claim 1 or 2, wherein said providing a plant cell with an amplification vector, or a precursor thereof, or said transfecting or transforming is done by direct viral transfection.

6. The process according to claim 1 or 2, wherein said providing a plant cell with an amplification vector, or a precursor thereof, or said transfecting or transforming is done by non-biological delivery.

7. The process according to claim 1 or 2, wherein said providing a plant cell with an amplification vector or said transfecting or transforming is done by conversion of a vector or a pro-vector DNA that was pre-integrated into a plant nuclear DNA to form an autonomously replicating plasmid.

8. The process according to claim 1 or 2, wherein said amplification vector is released from a precursor thereof which has two origins of replication.

9. The process according to claim 1 or 2, wherein said amplification vector is a DNA virus-derived vector.

10. The process according to claim 1 or 2, wherein said amplification vector is a DNA copy or a replication intermediate of an RNA virus-derived vector.

11. The process according to claim 1 or 2, wherein said amplification vector is of retrotransposon origin.

12. The process according to claim 1 or 2, wherein the amplification vector has additionally viral functions selected from the group consisting of: functions for reverse transcription, host infectivity, cell-to-cell and/or systemic movement, integration into a host chromosome, viral particle assembly, control of silencing by host, and control of host physiology.

13. The process according to claim 1 or 2, wherein said homologous or site-specific recombination is one-sided.

14. The process according to claim 1 or 2, wherein said homologous or site-specific recombination is two-sided.

15. The process according to claim 1 or 2, wherein said site-specific recombination is promoted or facilitated by recombination enzymes selected from the group consisting of: site specific recombinases, restriction enzymes, integrases, and resolvases.

16. The process according to claim 1 or 2, wherein said homologous recombination is promoted or facilitated by recombination enzymes selected from the group consisting of: RecA-like proteins, rare-cutting endonuclease of HO type, and I-SceI endonuclease.

17. The process according to claim 1 or 2, wherein said amplification vector is assembled in a process of recombination.

18. The process according to claim 2, wherein said first DNA contains a selectable marker for the selection of step (ii).

19. The process according to claim 2, wherein said first DNA comprises additionally a second sequence of interest.

20. The process according to claim 2, wherein the recombination of said first and said second DNA establishes a functional sequence.

21. The process according to claim 2, wherein said first and said second DNA each additionally contains a fragment of a selection marker, which makes a selection marker as a result of said recombination.

22. The process according to claim 2, wherein said second DNA is delivered by an amplification vector or a precursor thereof.

23. The process according to claim 2, wherein the function of a sequence introduced into the plant in steps (i) and (ii) is destroyed in steps (III) to (v).

24. The process according to claim 1 or 2, wherein expression of genes involved in non-homologous recombination is inhibited or suppressed.

25. The process according to claim 1 or 2, wherein the end result of recombination is a site-directed mutation.

26. The process according to claim 1 or 2, wherein said geminivirus is bean golden mosaic virus (BGMV).

* * * * *

SEQUENCE LISTING

```
<160> NUMBER OF SEQ ID NOS: 43

<210> SEQ ID NO 1
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 1
aactgcagtc tagactggcc gtcgttttac aac                                33

<210> SEQ ID NO 2
<211> LENGTH: 37
<212> TYPE: DNA
<213> ORGANISM: Artificial sequence
<220> FEATURE:
<223> OTHER INFORMATION: Synthetic oligonucleotide primer
```

```
<400> SEQUENCE: 2
aactgcagaa caattgctcg aggcgtaatc atggtca                                37

<210> SEQ ID NO 3
<211> LENGTH: 40
<212> TYPE: DNA
<213> ORGANISM: Artificial sequence
<220> FEATURE:
<223> OTHER INFORMATION: Synthetic oligonucleotide primer

<400> SEQUENCE: 3
gggaattcac tagtaaagat ctgccgtcga cttggaattg                             40

<210> SEQ ID NO 4
<211> LENGTH: 28
<212> TYPE: DNA
<213> ORGANISM: Artificial sequence
<220> FEATURE:
<223> OTHER INFORMATION: Synthetic oligonucleotide primer

<400> SEQUENCE: 4
caatgcatca tggcgcatca cgcttagg                                          28

<210> SEQ ID NO 5
<211> LENGTH: 33
<212> TYPE: DNA
<213> ORGANISM: Artificial sequence
<220> FEATURE:
<223> OTHER INFORMATION: Synthetic oligonculeotide primer

<400> SEQUENCE: 5
aagctgcagg tctatttcta tgattcgata acc                                    33

<210> SEQ ID NO 6
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 6
gaagatctgc aagaggaggt cagca                                             25

<210> SEQ ID NO 7
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 7
cggcatgcat gcatttggag gatttgctaa ctg                                    33

<210> SEQ ID NO 8
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 8
cggatgcatt caattatgta gagtcacaca g                                      31

<210> SEQ ID NO 9
<211> LENGTH: 28
<212> TYPE: DNA
```

<210> SEQ ID NO 9
<211> LENGTH: 28
<212> TYPE: DNA
<213> ORGANISM: Artificial sequence
<220> FEATURE:
<223> OTHER INFORMATION: Synthetic oligonucleotide primer

<400> SEQUENCE: 9
cgctcgaggc cgtcgacttg gaattgtc     28

<210> SEQ ID NO 10
<211> LENGTH: 51
<212> TYPE: DNA
<213> ORGANISM: Artificial sequence
<220> FEATURE:
<223> OTHER INFORMATION: Synthetic oligonucleotide primer

<400> SEQUENCE: 10
cccatgcatc tagagttaac ggccggccca aatatctaac gttctcacat g     51

<210> SEQ ID NO 11
<211> LENGTH: 39
<212> TYPE: DNA
<213> ORGANISM: Artificial sequence
<220> FEATURE:
<223> OTHER INFORMATION: Synthetic oligonucleotide primer

<400> SEQUENCE: 11
gttctagatg ttaacggcgc gccggcgtaa tcatggtca     39

<210> SEQ ID NO 12
<211> LENGTH: 42
<212> TYPE: DNA
<213> ORGANISM: Artificial sequence
<220> FEATURE:
<223> OTHER INFORMATION: Synthetic oligonucleotide primer

<400> SEQUENCE: 12
aaccatggag aattcggccg gccctggccg tcgttttaca ac     42

<210> SEQ ID NO 13
<211> LENGTH: 65
<212> TYPE: DNA
<213> ORGANISM: Artificial sequence
<220> FEATURE:
<223> OTHER INFORMATION: Synthetic oligonucleotide primer

<400> SEQUENCE: 13
cgggatcctg agctctataa cttcgtataa tgtatgctat acgaagttgt tctagatgtt     60
aacgg     65

<210> SEQ ID NO 14
<211> LENGTH: 71
<212> TYPE: DNA
<213> ORGANISM: Artificial sequence
<220> FEATURE:
<223> OTHER INFORMATION: Synthetic oligonucleotide primer

<400> SEQUENCE: 14
cgggatccct gcagataact tcgtataatc tatactatac gaagttagaa aacaaccat     60 ggagaattcg g     71

<210> SEQ ID NO 15
<211> LENGTH: 34
<212> TYPE: DNA
<213> ORGANISM: Artificial sequence
<220> FEATURE:
<223> OTHER INFORMATION: Synthetic oligonucleotide primer -continued

```
<400> SEQUENCE: 15
acaacttcgt atagcataca ttatacgaag ttat                              34

<210> SEQ ID NO 16
<211> LENGTH: 34
<212> TYPE: DNA
<213> ORGANISM: Artificial sequence
<220> FEATURE:
<223> OTHER INFORMATION: Synthetic oligonucleotide primer

<400> SEQUENCE: 16
ataacttcgt ataatctata ctatacgaag ttag                              34

<210> SEQ ID NO 17
<211> LENGTH: 43
<212> TYPE: DNA
<213> ORGANISM: Artificial sequence
<220> FEATURE:
<223> OTHER INFORMATION: Synthetic oligonucleotide primer

<400> SEQUENCE: 17
tcgagataac ttcgtatagc atacattata cgaagttata gct                    43

<210> SEQ ID NO 18
<211> LENGTH: 35
<212> TYPE: DNA
<213> ORGANISM: Artificial sequence
<220> FEATURE:
<223> OTHER INFORMATION: Synthetic oligonucleotide primer

<400> SEQUENCE: 18
ataacttcgt ataatgtatg ctatacgaag ttatc                             35

<210> SEQ ID NO 19
<211> LENGTH: 39
<212> TYPE: DNA
<213> ORGANISM: Artificial sequence
<220> FEATURE:
<223> OTHER INFORMATION: Synthetic oligonucleotide primer

<400> SEQUENCE: 19
gatcataact tcgtataatc tatactatac gaagttatt                         39

<210> SEQ ID NO 20
<211> LENGTH: 39
<212> TYPE: DNA
<213> ORGANISM: Artificial sequence
<220> FEATURE:
<223> OTHER INFORMATION: Synthetic oligonucleotide primer

<400> SEQUENCE: 20
ctagaataac ttcgtatagt atagattata cgaagttat                         39

<210> SEQ ID NO 21
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 21
catgccatgg ccaatttact gacct                                        25

<210> SEQ ID NO 22
<211> LENGTH: 28
<212> TYPE: DNA
```

```
<213> ORGANISM: Artificial sequence
<220> FEATURE:
<223> OTHER INFORMATION: Synthetic oligonucletoide primer

<400> SEQUENCE: 22
tgctctagac taatcgccat cttccagc                                           28

<210> SEQ ID NO 23
<211> LENGTH: 34
<212> TYPE: DNA
<213> ORGANISM: Artificial sequence
<220> FEATURE:
<223> OTHER INFORMATION: Synthetic oligonucleotide primer

<400> SEQUENCE: 23
tctctcgagt tacaaatatg ccaccacctc aaag                                    34

<210> SEQ ID NO 24
<211> LENGTH: 34
<212> TYPE: DNA
<213> ORGANISM: Artificial sequence
<220> FEATURE:
<223> OTHER INFORMATION: Synthetic oligonucleotide primer

<400> SEQUENCE: 24
gctctagagg atctatttct atgattcgat aacc                                    34

<210> SEQ ID NO 25
<211> LENGTH: 30
<212> TYPE: DNA
<213> ORGANISM: Artificial sequence
<220> FEATURE:
<223> OTHER INFORMATION: Synthetic oligonucleotide primer

<400> SEQUENCE: 25
gcctcgagct taaatggatt ctcagttagc                                         30

<210> SEQ ID NO 26
<211> LENGTH: 31
<212> TYPE: DNA
<213> ORGANISM: Artificial sequence
<220> FEATURE:
<223> OTHER INFORMATION: Synthetic oligonucleotide primer

<400> SEQUENCE: 26
cgggatcctt atttcaaaga ctttggttga g                                       31

<210> SEQ ID NO 27
<211> LENGTH: 33
<212> TYPE: DNA
<213> ORGANISM: Artificial sequence
<220> FEATURE:
<223> OTHER INFORMATION: Synthetic oligonucleotide primer

<400> SEQUENCE: 27
cgatgcatca cacgaattaa taatgtatgc gtc                                     33

<210> SEQ ID NO 28
<211> LENGTH: 34
<212> TYPE: DNA
<213> ORGANISM: Artificial sequence
<220> FEATURE:
<223> OTHER INFORMATION: Synthetic oligonuucleotide primer

<400> SEQUENCE: 28
cgggatcctt atccaacata atcaagatca aatg                                    34
```

```
<210> SEQ ID NO 29
<211> LENGTH: 64
<212> TYPE: DNA
<213> ORGANISM: Artificial sequence
<220> FEATURE:
<223> OTHER INFORMATION: Synthetic oligonucleotide primer

<400> SEQUENCE: 29
ggcatcgata taacttcgta tagcatacat tatacgaagt tatacaatgg gtcagtccct      60
tatg                                                                  64

<210> SEQ ID NO 30
<211> LENGTH: 61
<212> TYPE: DNA
<213> ORGANISM: Artificial sequence
<220> FEATURE:
<223> OTHER INFORMATION: Synthetic oligonulceotide primer

<400> SEQUENCE: 30
gcccatggat aacttgctat aatgtatgct atacgaagtt atgtcaaggt ttgacctgca      60
c                                                                     61

<210> SEQ ID NO 31
<211> LENGTH: 30
<212> TYPE: DNA
<213> ORGANISM: Artificial sequence
<220> FEATURE:
<223> OTHER INFORMATION: Synthetic oligonucleotide primer
<220> FEATURE:
<221> NAME/KEY: misc_feature
<222> LOCATION: (16)..(16)
<223> OTHER INFORMATION: n is a, c, g, or t

<400> SEQUENCE: 31
cgggatccca ggtggngcwt cmatggagat                                       30

<210> SEQ ID NO 32
<211> LENGTH: 28
<212> TYPE: DNA
<213> ORGANISM: Artificial sequence
<220> FEATURE:
<223> OTHER INFORMATION: Synthetic oligonucleotide primer

<400> SEQUENCE: 32
cggagctcgc atacacagth ccrtgcat                                         28

<210> SEQ ID NO 33
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 33
cgacagcgtc gccctcgttg ccatc                                            25

<210> SEQ ID NO 34
<211> LENGTH: 25
<212> TYPE: DNA
<213> ORGANISM: Artificial sequence
<220> FEATURE:
<223> OTHER INFORMATION: Synthetic oligonucleotide primer

<400> SEQUENCE: 34
gatggcaacg agggcgacgc tgtcg                                            25
```

<210> SEQ ID NO 35
<211> LENGTH: 36
<212> TYPE: DNA
<213> ORGANISM: Artificial sequence
<220> FEATURE:
<223> OTHER INFORMATION: Synthetic oligonucleotide primer

<400> SEQUENCE: 35
cgcaattgct cgagctttga ggtggtggca tatttg                                    36

<210> SEQ ID NO 36
<211> LENGTH: 22
<212> TYPE: DNA
<213> ORGANISM: Artificial sequence
<220> FEATURE:
<223> OTHER INFORMATION: Synthetic oligoncucleotide primer

<400> SEQUENCE: 36
cgctgaactt gtggccgttc ac                                                   22

<210> SEQ ID NO 37
<211> LENGTH: 51
<212> TYPE: DNA
<213> ORGANISM: Artificial sequence
<220> FEATURE:
<223> OTHER INFORMATION: Synthetic oligonucletoide primer

<400> SEQUENCE: 37
cggtcatgat tctcaagcac agtatggcat atttgtaaat atgcgagtgt c                   51

<210> SEQ ID NO 38
<211> LENGTH: 27
<212> TYPE: DNA
<213> ORGANISM: Artificial sequence
<220> FEATURE:
<223> OTHER INFORMATION: Synthetic oligonucleotide primer

<400> SEQUENCE: 38
gctctagaga cacgtggagg cgtacgg                                              27

<210> SEQ ID NO 39
<211> LENGTH: 51
<212> TYPE: DNA
<213> ORGANISM: Artificial sequence
<220> FEATURE:
<223> OTHER INFORMATION: Synthetic olignonucleotide primer

<400> SEQUENCE: 39
cggtcatgat tctcaagcac agtatggcat atttgtaaat atgcgagtgt c                   51

<210> SEQ ID NO 40
<211> LENGTH: 53
<212> TYPE: DNA
<213> ORGANISM: Artificial sequence
<220> FEATURE:
<223> OTHER INFORMATION: Synthetic oligonucleotide primer

<400> SEQUENCE: 40
ccgcggtgcg ggtgccaggg cgtgcccttg ggctccccgg gcgcgtactc cac                 53

<210> SEQ ID NO 41
<211> LENGTH: 49
<212> TYPE: DNA
<213> ORGANISM: Artificial sequence
<220> FEATURE:
<223> OTHER INFORMATION: Synthetic oligonucleotide primer

```
<400> SEQUENCE: 41
gtagtgcccc aactggggta acctttgagt tctctcagtt gggggcgta              49

<210> SEQ ID NO 42
<211> LENGTH: 48
<212> TYPE: DNA
<213> ORGANISM: Artificial sequence
<220> FEATURE:
<223> OTHER INFORMATION: Synthetic oligonucleotide primer

<400> SEQUENCE: 42
tttccatgga ttaccctgtt atccctaaag gcatctcgtc gcgtttac              48

<210> SEQ ID NO 43
<211> LENGTH: 32
<212> TYPE: DNA
<213> ORGANISM: Artificial sequence
<220> FEATURE:
<223> OTHER INFORMATION: Synthetic oligonucleotide primer

<400> SEQUENCE: 43
tttctgcagg aaatgaaagg ccgcgaaaca ag                               32
```